(12) United States Patent
DeVries et al.

(10) Patent No.: US 10,315,002 B2
(45) Date of Patent: Jun. 11, 2019

(54) VENTILATOR WITH INTEGRATED OXYGEN PRODUCTION

(71) Applicant: Ventec Life Systems, Inc., Bothell, WA (US)

(72) Inventors: Douglas F. DeVries, Kenmore, WA (US); David M. Good, Bothell, WA (US); Shan E. Gaw, Seattle, WA (US); Joseph Cipollone, Mission Viejo, CA (US); Richard Branson, Beaufort, SC (US)

(73) Assignee: Ventec Life Systems, Inc., Bothell, WA (US)

( * ) Notice: Subject to any disclaimer, the term of this patent is extended or adjusted under 35 U.S.C. 154(b) by 807 days.

(21) Appl. No.: 14/667,480

(22) Filed: Mar. 24, 2015

(65) Prior Publication Data
US 2016/0279363 A1  Sep. 29, 2016

(51) Int. Cl.
*A61M 16/00* (2006.01)
*A61M 16/04* (2006.01)
(Continued)

(52) U.S. Cl.
CPC ...... *A61M 16/101* (2014.02); *A61M 16/0051* (2013.01); *A61M 16/0069* (2014.02);
(Continued)

(58) Field of Classification Search
CPC .......... A61M 16/0003; A61M 16/0057; A61M 16/0063; A61M 16/0066; A61M 16/021;
(Continued)

(56) References Cited

U.S. PATENT DOCUMENTS

| 4,280,399 A | 7/1981 | Cunning |
| 4,331,455 A | 5/1982 | Sato |

(Continued)

FOREIGN PATENT DOCUMENTS

| EP | 0937478 B1 | 8/2003 | |
| WO | WO 9908738 A1 * | 2/1999 | ............ A61M 16/00 |
| WO | 2013033589 A1 | 3/2013 | |

OTHER PUBLICATIONS

US 8,012,240 B2, 09/2011, Sprinkle (withdrawn)

(Continued)

*Primary Examiner* — Jan Christopher L Merene
*Assistant Examiner* — Joseph D. Boecker
(74) *Attorney, Agent, or Firm* — Perkins Coie LLP

(57) ABSTRACT

A method of providing a breath to a human patient. The patient has a patient connection connected, by a patient circuit, to a ventilator having a first ventilator connection and a different second ventilator connection. Each of the first and second ventilator connections are in fluid communication with the patient circuit. The method includes identifying, with the ventilator, initiation of an inspiratory phase of the breath, delivering a bolus of oxygen to the first ventilator connection before or during the inspiratory phase, and delivering breathing gases comprising air to the second ventilator connection during the inspiratory phase. The ventilator isolates the bolus of oxygen delivered to the first ventilator connection from the breathing gases delivered to the second ventilator connection.

10 Claims, 35 Drawing Sheets

(51) Int. Cl.
  *A61M 16/06* (2006.01)
  *A61M 16/20* (2006.01)
  *A61M 16/10* (2006.01)
  *A61M 16/08* (2006.01)
  *B01D 53/053* (2006.01)
  *B01D 53/047* (2006.01)

(52) U.S. Cl.
  CPC ...... *A61M 16/024* (2017.08); *A61M 16/0858* (2014.02); *A61M 16/201* (2014.02); *A61M 16/202* (2014.02); *A61M 16/107* (2014.02); *A61M 16/1055* (2013.01); *A61M 16/20* (2013.01); *A61M 2016/0027* (2013.01); *A61M 2016/0036* (2013.01); *A61M 2016/0039* (2013.01); *A61M 2016/1025* (2013.01); *A61M 2202/0208* (2013.01); *A61M 2205/0272* (2013.01); *A61M 2205/3334* (2013.01); *A61M 2205/3358* (2013.01); *A61M 2205/42* (2013.01); *A61M 2205/52* (2013.01); *B01D 53/0476* (2013.01); *B01D 53/053* (2013.01); *B01D 2256/12* (2013.01); *B01D 2257/102* (2013.01); *B01D 2259/401* (2013.01); *B01D 2259/40009* (2013.01); *B01D 2259/4533* (2013.01)

(58) Field of Classification Search
  CPC .............. A61M 16/022; A61M 16/024; A61M 16/0883; A61M 16/10; A61M 16/101; A61M 16/12; A61M 16/122; A61M 16/125; A61M 16/127; A61M 16/202; A61M 16/204; A61M 2016/0015; A61M 2016/0018; A61M 2016/0027; A61M 2016/003; A61M 2016/0033; A61M 2016/0039; A61M 2016/102; A61M 2016/1025; A61M 2202/0208; A61M 2205/3331; A61M 2205/3334; A61M 2205/3344; A61M 2205/50; A61M 2205/502; A61M 2039/082; A61M 16/00
  See application file for complete search history.

(56) References Cited

U.S. PATENT DOCUMENTS

| | | |
|---|---|---|
| 4,357,936 A | 11/1982 | Ellestad et al. |
| 4,367,767 A | 1/1983 | Hurd |
| 4,386,945 A | 6/1983 | Gardner |
| 4,401,116 A | 8/1983 | Fry et al. |
| 4,417,573 A | 11/1983 | De Vries |
| 4,425,914 A | 1/1984 | Ray et al. |
| 4,449,990 A | 5/1984 | Tedford, Jr. |
| 4,450,838 A | 5/1984 | Miodownik |
| 4,459,982 A | 7/1984 | Fry |
| 4,502,873 A | 3/1985 | Mottram et al. |
| 4,516,424 A | 5/1985 | Rowland |
| 4,527,557 A | 7/1985 | DeVries et al. |
| 4,545,790 A | 10/1985 | Miller et al. |
| 4,561,287 A | 12/1985 | Rowland |
| 4,576,616 A | 3/1986 | Mottram et al. |
| 4,602,653 A | 7/1986 | Ruiz-Vela et al. |
| 4,621,632 A | 11/1986 | Bartels et al. |
| 4,627,860 A | 12/1986 | Rowland |
| 4,648,395 A | 3/1987 | Sato et al. |
| 4,648,888 A | 3/1987 | Rowland |
| 4,681,099 A | 7/1987 | Sato et al. |
| 4,702,240 A | 10/1987 | Chaoui |
| 4,794,922 A | 1/1989 | DeVries |
| 4,813,979 A | 3/1989 | Miller et al. |
| 4,869,733 A | 9/1989 | Stanford |
| 4,880,443 A | 11/1989 | Miller et al. |
| 4,905,685 A | 3/1990 | Olsson et al. |
| 4,936,297 A | 6/1990 | Greiff et al. |
| 4,971,609 A | 11/1990 | Pawlos |
| 4,983,190 A | 1/1991 | Verrando et al. |
| 4,993,269 A | 2/1991 | Guillaume et al. |
| 5,002,591 A | 3/1991 | Stanford |
| 5,014,694 A | 5/1991 | DeVries |
| 5,021,137 A | 6/1991 | Joshi et al. |
| 5,034,023 A | 7/1991 | Thompson |
| 5,071,453 A | 12/1991 | Hradek et al. |
| 5,072,729 A | 12/1991 | DeVries |
| 5,101,656 A | 4/1992 | Miller |
| 5,107,831 A | 4/1992 | Halpern et al. |
| 5,127,400 A | 7/1992 | DeVries et al. |
| 5,129,924 A | 7/1992 | Schultz |
| 5,134,329 A | 7/1992 | Lang |
| 5,166,563 A | 11/1992 | Bassine |
| 5,169,506 A | 12/1992 | Michaels |
| 5,186,793 A | 2/1993 | Michaels |
| 5,265,594 A | 11/1993 | Olsson et al. |
| 5,273,031 A | 12/1993 | Olsson et al. |
| 5,275,642 A | 1/1994 | Bassine |
| 5,296,110 A | 3/1994 | Tabatabaie-Raissi |
| 5,331,995 A | 7/1994 | Westfall et al. |
| 5,335,426 A | 8/1994 | Settlemyer et al. |
| 5,354,361 A | 10/1994 | Coffield |
| 5,370,112 A | 12/1994 | Perkins |
| 5,378,345 A | 1/1995 | Taylor et al. |
| 5,397,443 A | 3/1995 | Michaels |
| 5,400,777 A | 3/1995 | Olsson et al. |
| 5,469,372 A | 11/1995 | McBrearty et al. |
| 5,474,062 A | 12/1995 | DeVires et al. |
| 5,474,595 A | 12/1995 | McCombs |
| 5,494,028 A | 2/1996 | DeVries et al. |
| 5,497,767 A | 3/1996 | Olsson et al. |
| 5,501,212 A | 3/1996 | Psaros |
| 5,540,220 A | 7/1996 | Gropper et al. |
| 5,540,233 A | 7/1996 | Larsson et al. |
| 5,575,283 A | 11/1996 | Sjoestrand |
| 5,578,115 A | 11/1996 | Cole |
| 5,694,924 A | 12/1997 | Cewers |
| 5,694,926 A | 12/1997 | DeVries et al. |
| 5,701,883 A | 12/1997 | Hete et al. |
| 5,706,801 A | 1/1998 | Remes et al. |
| 5,720,277 A | 2/1998 | Olsson et al. |
| 5,740,796 A | 4/1998 | Skog |
| 5,743,253 A | 4/1998 | Castor et al. |
| 5,746,806 A | 5/1998 | Aylsworth et al. |
| 5,765,557 A | 6/1998 | Warters |
| 5,765,558 A | 6/1998 | Psaros et al. |
| 5,766,310 A | 6/1998 | Cramer |
| 5,810,324 A | 9/1998 | Eriksson et al. |
| 5,827,358 A | 10/1998 | Kulish et al. |
| 5,845,633 A | 12/1998 | Psaros |
| 5,849,219 A | 12/1998 | De Laat et al. |
| 5,858,062 A | 1/1999 | McCulloh et al. |
| 5,858,063 A | 1/1999 | Cao et al. |
| 5,862,802 A | 1/1999 | Bird |
| 5,868,133 A | 2/1999 | DeVries et al. |
| 5,871,564 A | 2/1999 | McCombs |
| 5,875,777 A | 3/1999 | Eriksson |
| 5,878,744 A | 3/1999 | Pfeiffer |
| 5,881,722 A | 3/1999 | DeVries et al. |
| 5,893,944 A | 4/1999 | Dong |
| 5,896,857 A | 4/1999 | Hely et al. |
| 5,906,672 A | 5/1999 | Michaels et al. |
| 5,917,135 A | 6/1999 | Michaels et al. |
| 5,931,162 A | 8/1999 | Christian |
| 5,937,853 A | 8/1999 | Strom |
| 5,948,142 A | 9/1999 | Holmes et al. |
| 5,957,130 A | 9/1999 | Krahbichler et al. |
| 5,968,236 A | 10/1999 | Bassine |
| 5,988,165 A | 11/1999 | Richey, II et al. |
| 5,997,617 A | 12/1999 | Czabala et al. |
| 6,010,555 A | 1/2000 | Smolarek et al. |
| 6,035,851 A | 3/2000 | Wallen |
| 6,062,218 A | 5/2000 | Krahbichler et al. |
| 6,068,680 A | 5/2000 | Kulish et al. |
| 6,073,630 A | 6/2000 | Adahan |
| 6,095,139 A | 8/2000 | Psaros |
| 6,102,038 A | 8/2000 | DeVries |

(56) References Cited

U.S. PATENT DOCUMENTS

| | | | |
|---|---|---|---|
| 6,112,744 A | 9/2000 | Hognelid | |
| 6,113,673 A | 9/2000 | Loutfy et al. | |
| 6,123,074 A | 9/2000 | Hete et al. | |
| 6,152,132 A * | 11/2000 | Psaros | A61M 16/00 128/200.24 |
| 6,152,134 A | 11/2000 | Webber et al. | |
| 6,152,135 A | 11/2000 | DeVries et al. | |
| 6,155,252 A | 12/2000 | Warters | |
| 6,156,100 A | 12/2000 | Conrad et al. | |
| 6,158,430 A | 12/2000 | Pfeiffer et al. | |
| 6,162,283 A | 12/2000 | Conrad et al. | |
| 6,176,897 B1 | 1/2001 | Keefer | |
| 6,189,532 B1 | 2/2001 | Hely et al. | |
| 6,190,441 B1 | 2/2001 | Czabala et al. | |
| 6,192,885 B1 | 2/2001 | Jalde | |
| 6,217,635 B1 | 4/2001 | Conrad et al. | |
| 6,234,170 B1 | 5/2001 | Bergkvist | |
| 6,253,767 B1 | 7/2001 | Mantz | |
| 6,263,873 B1 | 7/2001 | Hedenberg | |
| 6,269,811 B1 * | 8/2001 | Duff | A61M 16/12 128/204.18 |
| 6,298,848 B1 | 10/2001 | Skog | |
| 6,302,107 B1 | 10/2001 | Richey, II et al. | |
| 6,344,069 B2 | 2/2002 | Smolarek et al. | |
| 6,346,139 B1 | 2/2002 | Czabala | |
| 6,348,082 B1 | 2/2002 | Murdoch et al. | |
| 6,360,740 B1 | 3/2002 | Ward et al. | |
| 6,386,235 B1 | 5/2002 | McCulloh et al. | |
| 6,393,802 B1 | 5/2002 | Bowser et al. | |
| 6,394,089 B1 | 5/2002 | Cantrill et al. | |
| 6,395,065 B1 | 5/2002 | Murdoch et al. | |
| 6,412,483 B1 | 7/2002 | Jones et al. | |
| 6,446,630 B1 | 9/2002 | Todd, Jr. | |
| 6,471,744 B1 | 10/2002 | Hill | |
| 6,478,850 B1 | 11/2002 | Warren | |
| 6,478,857 B2 | 11/2002 | Czabala | |
| 6,497,755 B2 | 12/2002 | Murdoch et al. | |
| 6,514,318 B2 | 2/2003 | Keefer | |
| 6,514,319 B2 | 2/2003 | Keefer et al. | |
| 6,516,798 B1 | 2/2003 | Davies | |
| 6,520,176 B1 | 2/2003 | Dubois et al. | |
| 6,524,370 B2 | 2/2003 | Maheshwary et al. | |
| 6,526,970 B2 | 3/2003 | DeVries et al. | |
| 6,532,956 B2 | 3/2003 | Hill | |
| 6,547,851 B2 | 4/2003 | Warren | |
| 6,551,384 B1 | 4/2003 | Ackley et al. | |
| 6,553,992 B1 | 4/2003 | Berthon-Jones et al. | |
| 6,558,451 B2 | 5/2003 | McCombs et al. | |
| 6,564,798 B1 | 5/2003 | Jalde | |
| 6,565,635 B2 | 5/2003 | Keefer et al. | |
| 6,595,213 B2 | 7/2003 | Bennarsten | |
| 6,601,583 B2 | 8/2003 | Pessala et al. | |
| 6,622,726 B1 | 9/2003 | Du | |
| 6,626,175 B2 | 9/2003 | Jafari et al. | |
| 6,629,525 B2 | 10/2003 | Hill et al. | |
| 6,640,807 B2 | 11/2003 | Bennarsten | |
| 6,641,644 B2 | 11/2003 | Jagger et al. | |
| 6,641,645 B1 | 11/2003 | Lee et al. | |
| 6,644,312 B2 | 11/2003 | Berthon-Jones et al. | |
| 6,651,652 B1 | 11/2003 | Wård | |
| 6,651,658 B1 | 11/2003 | Hill et al. | |
| 6,651,692 B2 | 11/2003 | Meckes et al. | |
| 6,660,065 B2 | 12/2003 | Byrd et al. | |
| 6,679,258 B1 | 1/2004 | Strom | |
| 6,691,702 B2 | 2/2004 | Appel et al. | |
| 6,694,978 B1 | 2/2004 | Bennarsten | |
| 6,702,880 B2 | 3/2004 | Roberts et al. | |
| 6,712,876 B2 | 3/2004 | Cao et al. | |
| 6,712,877 B2 | 3/2004 | Cao et al. | |
| 6,739,334 B2 | 5/2004 | Valeij | |
| 6,740,146 B2 | 5/2004 | Simonds | |
| 6,755,193 B2 | 6/2004 | Berthon-Jones et al. | |
| 6,758,216 B1 | 7/2004 | Berthon-Jones et al. | |
| 6,761,166 B2 | 7/2004 | Ahlmen et al. | |
| 6,764,534 B2 | 7/2004 | McCombs et al. | |
| 6,782,888 B1 | 8/2004 | Friberg et al. | |
| 6,793,719 B2 | 9/2004 | Kim et al. | |
| 6,805,122 B2 | 10/2004 | Richey, II et al. | |
| 6,811,590 B2 | 11/2004 | Lee et al. | |
| 6,837,244 B2 | 1/2005 | Yagi et al. | |
| 6,845,773 B2 | 1/2005 | Berthon-Jones et al. | |
| 6,860,858 B2 | 3/2005 | Green et al. | |
| 6,863,068 B2 | 3/2005 | Jamison et al. | |
| 6,866,700 B2 | 3/2005 | Amann | |
| 6,877,511 B2 | 4/2005 | DeVries et al. | |
| 6,889,726 B2 | 5/2005 | Richey, II et al. | |
| 6,896,721 B1 | 5/2005 | Lynn | |
| 6,908,503 B2 | 6/2005 | McCombs et al. | |
| 6,910,480 B1 | 6/2005 | Berthon-Jones | |
| 6,923,180 B2 | 8/2005 | Richey, II et al. | |
| 6,935,460 B2 | 8/2005 | McCombs et al. | |
| 6,949,133 B2 | 9/2005 | McCombs et al. | |
| 6,997,881 B2 | 2/2006 | Green et al. | |
| 7,000,610 B2 | 2/2006 | Bennarsten et al. | |
| 7,032,592 B2 | 4/2006 | Castor et al. | |
| 7,040,318 B2 | 5/2006 | Dascher et al. | |
| 7,055,522 B2 | 6/2006 | Berthon-Jones | |
| 7,066,985 B2 | 6/2006 | Deane et al. | |
| 7,077,133 B2 | 7/2006 | Yagi et al. | |
| 7,081,745 B2 | 7/2006 | Haveri | |
| 7,089,937 B2 | 8/2006 | Berthon-Jones et al. | |
| 7,094,275 B2 | 8/2006 | Keefer et al. | |
| 7,100,609 B2 | 9/2006 | Berthon-Jones et al. | |
| 7,105,038 B2 | 9/2006 | Lee et al. | |
| 7,121,276 B2 | 10/2006 | Jagger et al. | |
| 7,121,277 B2 | 10/2006 | Strom | |
| 7,135,059 B2 | 11/2006 | Deane et al. | |
| 7,156,903 B2 | 1/2007 | McCombs | |
| 7,171,963 B2 | 2/2007 | Jagger et al. | |
| 7,179,326 B2 | 2/2007 | Nakamura et al. | |
| 7,188,621 B2 | 3/2007 | DeVries et al. | |
| 7,213,468 B2 | 5/2007 | Fujimoto | |
| 7,219,666 B2 | 5/2007 | Friberg et al. | |
| 7,222,623 B2 | 5/2007 | DeVries et al. | |
| 7,250,073 B2 | 7/2007 | Keefer et al. | |
| 7,255,103 B2 | 8/2007 | Bassin | |
| 7,279,029 B2 | 10/2007 | Occhialini et al. | |
| 7,294,170 B2 | 11/2007 | Richey, II et al. | |
| 7,329,304 B2 | 2/2008 | Bliss et al. | |
| 7,347,207 B2 | 3/2008 | Ahlmen et al. | |
| 7,350,521 B2 | 4/2008 | Whitley et al. | |
| 7,367,337 B2 | 5/2008 | Berthon-Jones et al. | |
| 7,368,005 B2 | 5/2008 | Bliss et al. | |
| RE40,402 E | 6/2008 | Leonhardt et al. | |
| 7,402,193 B2 | 7/2008 | Bliss et al. | |
| 7,427,315 B2 | 9/2008 | Dolensky et al. | |
| 7,428,902 B2 | 9/2008 | Du et al. | |
| 7,429,289 B2 | 9/2008 | Dolensky et al. | |
| 7,431,032 B2 | 10/2008 | Jagger et al. | |
| 7,438,745 B2 | 10/2008 | Deane et al. | |
| 7,445,546 B2 | 11/2008 | Hondmann et al. | |
| 7,445,663 B1 | 11/2008 | Hunter et al. | |
| 7,455,717 B2 | 11/2008 | Sprinkle | |
| 7,473,299 B2 | 1/2009 | Occhialini et al. | |
| 7,491,261 B2 | 2/2009 | Warren et al. | |
| 7,497,215 B1 | 3/2009 | Nguyen et al. | |
| 7,510,601 B2 | 3/2009 | Whitley et al. | |
| 7,517,385 B2 | 4/2009 | Winter | |
| 7,524,365 B2 | 4/2009 | Lin | |
| 7,527,053 B2 | 5/2009 | DeVries et al. | |
| 7,533,872 B2 | 5/2009 | Lee et al. | |
| 7,550,031 B2 | 6/2009 | Hunter et al. | |
| 7,550,036 B2 | 6/2009 | Lee et al. | |
| 7,556,670 B2 | 7/2009 | Aylsworth et al. | |
| 7,559,326 B2 | 7/2009 | Smith et al. | |
| 7,585,351 B2 | 9/2009 | Deane et al. | |
| 7,590,551 B2 | 9/2009 | Auer | |
| 7,604,004 B2 | 10/2009 | Jagger et al. | |
| 7,604,005 B2 | 10/2009 | Jagger et al. | |
| 7,628,151 B2 | 12/2009 | Bassin | |
| 7,637,989 B2 | 12/2009 | Bong | |
| 7,655,059 B2 | 2/2010 | Wang et al. | |
| 7,655,063 B2 | 2/2010 | Wang et al. | |
| 7,682,428 B2 | 3/2010 | Nawata et al. | |

(56) References Cited

U.S. PATENT DOCUMENTS

| | | |
|---|---|---|
| 7,682,429 B2 | 3/2010 | Dolensky et al. |
| 7,686,870 B1 | 3/2010 | Deane et al. |
| 7,704,304 B2 | 4/2010 | Warren et al. |
| 7,708,802 B1 | 5/2010 | Deane et al. |
| 7,708,818 B2 | 5/2010 | Clark |
| 7,717,981 B2 | 5/2010 | LaBuda et al. |
| 7,722,700 B2 | 5/2010 | Sprinkle |
| 7,727,160 B2 | 6/2010 | Green et al. |
| 7,730,887 B2 | 6/2010 | Deane et al. |
| 7,753,996 B1 | 7/2010 | Deane et al. |
| 7,758,672 B2 | 7/2010 | Lee et al. |
| 7,763,103 B2 | 7/2010 | Dolensky et al. |
| 7,766,010 B2 | 8/2010 | Jagger et al. |
| 7,771,511 B2 | 8/2010 | Dolensky |
| 7,780,768 B2 | 8/2010 | Taylor et al. |
| 7,780,769 B2 | 8/2010 | Dolensky et al. |
| 7,794,522 B2 | 9/2010 | Bliss et al. |
| 7,828,878 B2 | 11/2010 | Zhong et al. |
| 7,837,761 B2 | 11/2010 | Bliss et al. |
| 7,841,343 B2 | 11/2010 | Deane et al. |
| 7,849,854 B2 | 12/2010 | DeVries et al. |
| 7,857,894 B2 | 12/2010 | Taylor et al. |
| 7,861,716 B2 | 1/2011 | Borrello |
| 7,866,315 B2 | 1/2011 | Jagger et al. |
| 7,874,290 B2 | 1/2011 | Chalvignac |
| 7,875,105 B2 | 1/2011 | Chambers et al. |
| 7,892,322 B2 | 2/2011 | Ono et al. |
| 7,909,034 B2 | 3/2011 | Sinderby et al. |
| 7,914,459 B2 | 3/2011 | Green et al. |
| 7,918,925 B2 | 4/2011 | Dolensky et al. |
| 7,922,789 B1 | 4/2011 | Deane et al. |
| 7,934,499 B2 | 5/2011 | Berthon-Jones |
| 7,954,493 B2 | 6/2011 | Nawata |
| 8,006,692 B2 | 8/2011 | Smith et al. |
| 8,016,916 B2 | 9/2011 | Ono et al. |
| 8,016,918 B2 | 9/2011 | LaBuda et al. |
| 8,016,925 B2 | 9/2011 | McCombs et al. |
| 8,020,553 B2 | 9/2011 | Jagger et al. |
| 8,051,852 B2 | 11/2011 | Bassin |
| 8,062,003 B2 | 11/2011 | Goertzen et al. |
| 8,070,853 B2 | 12/2011 | Sprinkle |
| 8,070,864 B2 | 12/2011 | Uchiyama et al. |
| 8,070,922 B2 | 12/2011 | Nelson et al. |
| 8,075,676 B2 | 12/2011 | Thompson et al. |
| 8,100,125 B2 | 1/2012 | Duquette et al. |
| 8,118,024 B2 | 2/2012 | DeVries et al. |
| 8,122,885 B2 | 2/2012 | Berthon-Jones et al. |
| 8,123,497 B2 | 2/2012 | Richey, II et al. |
| 8,142,544 B2 | 3/2012 | Taylor et al. |
| 8,146,596 B2 | 4/2012 | Smith et al. |
| 8,147,597 B2 | 4/2012 | Dolensky et al. |
| 8,156,937 B2 | 4/2012 | DeVries et al. |
| 8,167,988 B2 | 5/2012 | Dolensky et al. |
| 8,192,526 B2 | 6/2012 | Zhong et al. |
| 8,210,205 B2 | 7/2012 | Michaels |
| 8,225,789 B2 | 7/2012 | Berthon-Jones |
| 8,226,745 B2 | 7/2012 | Siew-Wah et al. |
| 8,236,095 B1 | 8/2012 | Bassine |
| 8,256,419 B2 | 9/2012 | Sinderby et al. |
| 8,257,473 B2 | 9/2012 | McCombs et al. |
| 8,280,498 B2 | 10/2012 | Jalde |
| 8,282,717 B2 | 10/2012 | Chambers et al. |
| 8,297,279 B2 | 10/2012 | DeVries et al. |
| 8,337,599 B2 | 12/2012 | Kiritake |
| 8,343,259 B2 | 1/2013 | Knaebel |
| 8,349,053 B2 | 1/2013 | Lee et al. |
| 8,361,204 B1 | 1/2013 | Bassine |
| 8,366,815 B2 | 2/2013 | Taylor et al. |
| 8,371,298 B2 | 2/2013 | Hallback et al. |
| 8,375,944 B2 | 2/2013 | Kwok |
| 8,377,180 B2 | 2/2013 | Maeda et al. |
| 8,377,181 B2 | 2/2013 | Taylor et al. |
| 8,388,548 B2 | 3/2013 | Green et al. |
| 8,388,745 B1 | 3/2013 | Pelletier et al. |
| 8,400,290 B2 | 3/2013 | Baker, Jr. |
| 8,418,691 B2 | 4/2013 | Jafari et al. |
| 8,418,692 B2 | 4/2013 | Sanchez |
| 8,424,520 B2 | 4/2013 | Thiessen |
| 8,424,521 B2 | 4/2013 | Jafari et al. |
| 8,428,672 B2 | 4/2013 | Sherman et al. |
| 8,434,480 B2 | 5/2013 | Jafari et al. |
| 8,434,482 B2 | 5/2013 | Borrello |
| 8,434,488 B2 | 5/2013 | Li et al. |
| 8,435,013 B2 | 5/2013 | Kondou et al. |
| 8,440,004 B2 | 5/2013 | Taylor et al. |
| 8,443,294 B2 | 5/2013 | Skidmore et al. |
| 8,448,640 B2 | 5/2013 | Bassin |
| 8,448,641 B2 | 5/2013 | Jafari et al. |
| 8,469,026 B2 | 6/2013 | Blomberg et al. |
| 8,522,780 B2 | 9/2013 | DeVries et al. |
| 8,627,819 B2 | 1/2014 | DeVries et al. |
| 8,683,997 B2 | 4/2014 | DeVries et al. |
| 8,844,530 B2 | 9/2014 | Birnkrant |
| 9,126,002 B2 | 9/2015 | DeVries et al. |
| 2002/0053286 A1 | 5/2002 | Czabala |
| 2002/0092420 A1 | 7/2002 | Jagger et al. |
| 2002/0121278 A1* | 9/2002 | Hete ............... A61M 16/04 128/204.18 |
| 2003/0010208 A1 | 1/2003 | Jagger et al. |
| 2003/0024766 A1 | 2/2003 | Briscoe |
| 2003/0051729 A1 | 3/2003 | Be et al. |
| 2003/0131848 A1 | 7/2003 | Stenzler |
| 2003/0196550 A1 | 10/2003 | Keefer et al. |
| 2003/0200865 A1 | 10/2003 | McCombs et al. |
| 2003/0230308 A1 | 12/2003 | Linden |
| 2004/0231913 A1 | 11/2004 | McCombs et al. |
| 2005/0045040 A1 | 3/2005 | McCombs |
| 2005/0072298 A1 | 4/2005 | Deane et al. |
| 2005/0072306 A1 | 4/2005 | Deane et al. |
| 2005/0072423 A1 | 4/2005 | Deane et al. |
| 2005/0072426 A1 | 4/2005 | Deane et al. |
| 2005/0103341 A1 | 5/2005 | Deane et al. |
| 2005/0112013 A1 | 5/2005 | DeVries et al. |
| 2005/0217481 A1 | 10/2005 | Dunne et al. |
| 2005/0257686 A1 | 11/2005 | Occhialini et al. |
| 2006/0011065 A1 | 1/2006 | Hastings |
| 2006/0064802 A1 | 3/2006 | Damrath et al. |
| 2006/0086251 A1 | 4/2006 | Sprinkle |
| 2006/0102181 A1 | 5/2006 | McCombs et al. |
| 2006/0117957 A1 | 6/2006 | McCombs et al. |
| 2006/0137522 A1 | 6/2006 | Nishimura et al. |
| 2006/0174871 A1 | 8/2006 | Jagger et al. |
| 2006/0174875 A1 | 8/2006 | Jagger et al. |
| 2006/0174877 A1 | 8/2006 | Jagger et al. |
| 2006/0230924 A1 | 10/2006 | Deane et al. |
| 2006/0230929 A1 | 10/2006 | Bliss et al. |
| 2006/0230931 A1 | 10/2006 | Bliss et al. |
| 2006/0230939 A1 | 10/2006 | Bliss et al. |
| 2006/0266357 A1 | 11/2006 | McCombs et al. |
| 2006/0283325 A1 | 12/2006 | Sugano |
| 2007/0031302 A1 | 2/2007 | Wittrup et al. |
| 2007/0056583 A1 | 3/2007 | Jagger et al. |
| 2007/0056584 A1 | 3/2007 | Jagger et al. |
| 2007/0084342 A1 | 4/2007 | Hunter et al. |
| 2007/0084349 A1 | 4/2007 | Calkins et al. |
| 2007/0101999 A1 | 5/2007 | Duquette et al. |
| 2007/0135757 A1* | 6/2007 | Acker ............... A61M 16/0666 604/26 |
| 2007/0144521 A1 | 6/2007 | DeVries et al. |
| 2007/0148016 A1 | 6/2007 | Crawford et al. |
| 2007/0169623 A1 | 7/2007 | Lee et al. |
| 2007/0199566 A1 | 8/2007 | Be'eri |
| 2007/0214955 A1 | 9/2007 | Aylsworth et al. |
| 2007/0227360 A1 | 10/2007 | Atlas et al. |
| 2007/0227540 A1 | 10/2007 | Ljungberg et al. |
| 2007/0272243 A1 | 11/2007 | Sherman et al. |
| 2007/0289446 A1 | 12/2007 | Occhialini et al. |
| 2008/0028933 A1 | 2/2008 | Ross et al. |
| 2008/0034975 A1 | 2/2008 | Chambers et al. |
| 2008/0053441 A1* | 3/2008 | Gottlib ............ A61M 16/0051 128/204.23 |
| 2008/0066616 A1 | 3/2008 | Sprinkle |
| 2008/0087170 A1 | 4/2008 | Deane et al. |
| 2008/0092892 A1 | 4/2008 | Boyle et al. |

(56) References Cited

U.S. PATENT DOCUMENTS

| | | | |
|---|---|---|---|
| 2008/0092893 A1 | 4/2008 | Boyle et al. | |
| 2008/0110338 A1 | 5/2008 | Taylor et al. | |
| 2008/0110461 A1 | 5/2008 | Mulqueeny et al. | |
| 2008/0185544 A1 | 8/2008 | Yeh | |
| 2008/0196580 A1 | 8/2008 | Bliss et al. | |
| 2008/0202337 A1 | 8/2008 | Taylor et al. | |
| 2008/0202508 A1 | 8/2008 | McClain et al. | |
| 2008/0251071 A1 | 10/2008 | Armitstead et al. | |
| 2008/0257145 A1 | 10/2008 | Sprinkle et al. | |
| 2008/0257349 A1 | 10/2008 | Hedner et al. | |
| 2008/0282880 A1 | 11/2008 | Bliss et al. | |
| 2008/0302363 A1 | 12/2008 | Kroupa | |
| 2008/0314385 A1 | 12/2008 | Brunner et al. | |
| 2008/0315441 A1 | 12/2008 | Lee et al. | |
| 2009/0007912 A1 | 1/2009 | Lindell et al. | |
| 2009/0025560 A1 | 1/2009 | Takemasa | |
| 2009/0025564 A1 | 1/2009 | Kuwabara | |
| 2009/0044698 A1 | 2/2009 | Meacham | |
| 2009/0065007 A1 | 3/2009 | Wilkinson et al. | |
| 2009/0065526 A1 | 3/2009 | Sprinkle | |
| 2009/0071333 A1 | 3/2009 | LaBuda et al. | |
| 2009/0078251 A1 | 3/2009 | Zucchi et al. | |
| 2009/0084381 A1 | 4/2009 | DeVries et al. | |
| 2009/0107500 A1 | 4/2009 | Edwards | |
| 2009/0133368 A1 | 5/2009 | Calkins et al. | |
| 2009/0133694 A1 | 5/2009 | Solci et al. | |
| 2009/0145428 A1 | 6/2009 | Sward et al. | |
| 2009/0167698 A1 | 7/2009 | Altas et al. | |
| 2009/0188502 A1 | 7/2009 | Tiedje | |
| 2009/0211448 A1 | 8/2009 | McClain | |
| 2009/0229459 A1 | 9/2009 | Warren et al. | |
| 2009/0250059 A1 | 10/2009 | Allum et al. | |
| 2009/0308396 A1 | 12/2009 | McClain | |
| 2010/0024819 A1 | 2/2010 | Tiedje | |
| 2010/0051030 A1 | 3/2010 | Richard et al. | |
| 2010/0052293 A1 | 3/2010 | Brooks et al. | |
| 2010/0078018 A1* | 4/2010 | Heinonen | A61M 16/01 128/202.22 |
| 2010/0095841 A1 | 4/2010 | Naheiri | |
| 2010/0116270 A1 | 5/2010 | Edwards et al. | |
| 2010/0126249 A1 | 5/2010 | Matsuzaki | |
| 2010/0229867 A1 | 9/2010 | Bertinetti et al. | |
| 2010/0275921 A1* | 11/2010 | Schindhelm | A61B 5/08 128/204.23 |
| 2010/0282084 A1 | 11/2010 | Taylor et al. | |
| 2010/0288279 A1 | 11/2010 | Seiver et al. | |
| 2010/0294127 A1 | 11/2010 | Dolensky | |
| 2011/0000489 A1 | 1/2011 | Laksov et al. | |
| 2011/0030684 A1 | 2/2011 | Wilkinson et al. | |
| 2011/0030685 A1 | 2/2011 | Wilkinson et al. | |
| 2011/0030686 A1 | 2/2011 | Wilkinson et al. | |
| 2011/0030687 A1 | 2/2011 | Wilkinson et al. | |
| 2011/0030689 A1 | 2/2011 | Wilkinson et al. | |
| 2011/0057651 A1 | 3/2011 | Duric et al. | |
| 2011/0067699 A1 | 3/2011 | Caruso et al. | |
| 2011/0073115 A1 | 3/2011 | Wood et al. | |
| 2011/0113964 A1 | 5/2011 | Chambers et al. | |
| 2011/0154986 A1 | 6/2011 | Lee et al. | |
| 2011/0192122 A1 | 8/2011 | Whitesel et al. | |
| 2011/0197881 A1 | 8/2011 | Truschel et al. | |
| 2011/0197883 A1 | 8/2011 | McDaniel et al. | |
| 2011/0197884 A1 | 8/2011 | Duff et al. | |
| 2011/0197887 A1 | 8/2011 | Truschel et al. | |
| 2011/0209706 A1 | 9/2011 | Truschel et al. | |
| 2011/0209707 A1 | 9/2011 | Terhark | |
| 2011/0220107 A1 | 9/2011 | Kimm et al. | |
| 2011/0232483 A1 | 9/2011 | Haberland et al. | |
| 2011/0232645 A1 | 9/2011 | Smith | |
| 2011/0247616 A1 | 10/2011 | Von Hollen et al. | |
| 2011/0247620 A1 | 10/2011 | Armstrong et al. | |
| 2011/0247621 A1 | 10/2011 | Richard et al. | |
| 2011/0247622 A1 | 10/2011 | Schneider et al. | |
| 2011/0259334 A1 | 10/2011 | Alfieri et al. | |
| 2011/0303223 A1 | 12/2011 | Kane et al. | |
| 2011/0315140 A1 | 12/2011 | Shuman | |
| 2012/0000462 A1 | 1/2012 | Edwards et al. | |
| 2012/0006199 A1 | 1/2012 | McCombs et al. | |
| 2012/0006326 A1* | 1/2012 | Ahmad | A61M 16/12 128/204.22 |
| 2012/0012109 A1 | 1/2012 | Chalvignac | |
| 2012/0017909 A1 | 1/2012 | Porges et al. | |
| 2012/0027628 A1 | 2/2012 | Ogawa | |
| 2012/0037159 A1 | 2/2012 | Mulqueeny et al. | |
| 2012/0055340 A1 | 3/2012 | Wilkinson et al. | |
| 2012/0055474 A1 | 3/2012 | Wilkinson | |
| 2012/0055475 A1 | 3/2012 | Wilkinson | |
| 2012/0055477 A1 | 3/2012 | Wilkinson | |
| 2012/0055480 A1 | 3/2012 | Wilkinson | |
| 2012/0055482 A1 | 3/2012 | Wilkinson | |
| 2012/0055483 A1 | 3/2012 | Wilkinson et al. | |
| 2012/0060840 A1 | 3/2012 | Refsland et al. | |
| 2012/0125336 A1 | 5/2012 | Berthon-Jones et al. | |
| 2012/0125337 A1 | 5/2012 | Asanoi | |
| 2012/0152248 A1 | 6/2012 | Richey, II et al. | |
| 2012/0167883 A1 | 7/2012 | Taylor et al. | |
| 2012/0167886 A1 | 7/2012 | Taylor et al. | |
| 2012/0167887 A1 | 7/2012 | Taylor et al. | |
| 2012/0167888 A1 | 7/2012 | Taylor et al. | |
| 2012/0177546 A1 | 7/2012 | Hilbig | |
| 2012/0192862 A1 | 8/2012 | Lewis et al. | |
| 2012/0192864 A1 | 8/2012 | Galbraith et al. | |
| 2012/0192867 A1 | 8/2012 | Lewis et al. | |
| 2012/0247329 A1 | 10/2012 | Hilbig | |
| 2012/0266883 A1 | 10/2012 | Taylor et al. | |
| 2012/0285543 A1 | 11/2012 | Michaels | |
| 2012/0291884 A1 | 11/2012 | Yamaura et al. | |
| 2012/0304867 A1 | 12/2012 | Watanabe et al. | |
| 2012/0308779 A1 | 12/2012 | Klee et al. | |
| 2012/0318145 A1 | 12/2012 | Hilbig et al. | |
| 2013/0008438 A1 | 1/2013 | Sugawara et al. | |
| 2013/0008444 A1 | 1/2013 | Chalvignac et al. | |
| 2013/0025591 A1 | 1/2013 | Clark et al. | |
| 2013/0031784 A1 | 2/2013 | Chambers et al. | |
| 2013/0087145 A1 | 4/2013 | Kobrich et al. | |
| 2013/0087146 A1 | 4/2013 | Callaghan et al. | |
| 2013/0092159 A1 | 4/2013 | Ulrichskotter et al. | |
| 2013/0098361 A1 | 4/2013 | Kobrich et al. | |
| 2013/0104898 A1 | 5/2013 | Berthon-Jones | |
| 2013/0125891 A1 | 5/2013 | Eddy | |
| 2013/0186400 A1 | 7/2013 | Jafari et al. | |
| 2013/0186401 A1 | 7/2013 | Jafari et al. | |
| 2013/0255689 A1 | 10/2013 | Kim et al. | |
| 2013/0276789 A1 | 10/2013 | Garde et al. | |
| 2014/0007878 A1* | 1/2014 | Armitstead | A61B 5/083 128/204.23 |
| 2014/0116441 A1 | 5/2014 | McDaniel | |
| 2015/0000660 A1 | 1/2015 | Martin | |
| 2015/0320962 A1* | 11/2015 | Bafile | A61M 16/0816 128/204.18 |
| 2016/0243330 A1* | 8/2016 | DeStefano | A61M 16/20 |
| 2016/0279362 A1* | 9/2016 | DeVries | A61M 16/101 |
| 2016/0279363 A1 | 9/2016 | DeVries et al. | |

OTHER PUBLICATIONS

Rodriquez et al., "Maximizing Oxygen Delivery During Mechanical Ventilation with a Portable Oxygen Concentrator," Journal of Trauma—Injury Infection & Critical Care, 69(1), Jul. 2010, pp. S87-S93.

Gustafson et al., "Pulse Dose Delivery of Oxygen in Mechanically Ventilated Pigs with Acute Lung Injury," The Journal of Trauma and Acute Care Surgery, 75(5), Nov. 2013, pp. 775-779.

Branson, D. Richard et al., "Maximizing Oxygen Delivery During Mechanical Ventilation With a Portable Oxygen Concentrator," The Journal of TRAUMA® Injury, Infection, and Critical Care, vol. 69, No. 1, July Supplement 2010, 7 pages.

\* cited by examiner

VENTILATOR WITH INTEGRATED OXYGEN PRODUCTION

BACKGROUND OF THE INVENTION

Field of the Invention

The present invention is directed generally to ventilators used to assist human patients with breathing.

Description of the Related Art

Respiration may be characterized as including both an inspiratory phase and an exhalation phase. During the inspiratory phase, inspiratory gases are drawn into the lungs, and during the exhalation phase, exhalation gases are expelled from the lungs.

Mechanical ventilators are used to assist with breathing. Conventional ventilators typically push inspiratory gases including oxygen into the patient's lungs. Many patients who use a ventilator also need other types of assistance related to treating and maintaining their airways and lungs. For example, some patients may use a nebulizer to deliver drugs to their lungs and/or airways. Further, some patients may need help clearing secretions from their lungs and/or airways. Such assistance is typically provided by a conventional suction device. Thus, in additional to a ventilator, many patients require multiple devices and traveling with such equipment can be particularly problematic.

Thus, a need exists for ventilators configured to be portable and/or provide additional functionality beyond delivering inspiratory gases into the patient's lungs. The present application provides these and other advantages as will be apparent from the following detailed description and accompanying figures.

SUMMARY OF THE INVENTION

An embodiment includes a method of providing a breath to a human patient. The human patient has a patient connection connected, by a patient circuit, to a ventilator device. The breath has an inspiratory phase with a beginning and an end. The method includes delivering a bolus of oxygen to the patient circuit at or before the beginning of the inspiratory phase of the breath, terminating the delivery of the bolus of oxygen before the end of the inspiratory phase of the breath, and delivering breathing gases including air to the patient circuit before the end of the inspiratory phase of the breath. The patient circuit delivers the bolus of oxygen and the breathing gases to the patient connection. Optionally, the method may further include waiting until after the delivery of the bolus of oxygen delivered for the breath has been terminated before delivering the breathing gases.

Optionally, the method may further include receiving a bolus volume value. In such embodiments, the bolus of oxygen delivered for the breath has a volume substantially equal to the bolus volume value.

Optionally, delivering the breathing gases to the patient circuit includes providing the breathing gases to the patient circuit at a first input location of the patient circuit, and delivering the bolus of oxygen to the patient circuit includes providing the bolus of oxygen to the patient circuit at a second input location of the patient circuit closer than the first input location to the patient connection.

Combined the bolus of oxygen and the breathing gases delivered for the breath have a total inspiratory volume. Optionally, the bolus of oxygen delivered for the breath has a volume that is less than about 75% of the total inspiratory volume. Optionally, the bolus of oxygen delivered for the breath has a volume that is between about 50% of the total inspiratory volume and about 75% of the total inspiratory volume.

Optionally, the method may further include receiving an oxygen flow equivalent value associated with an oxygen flow rate which if applied to the patient circuit continuously from the beginning of the inspiratory phase of the breath to an end of an expiratory phase of the breath would produce a first volume of oxygen. In such embodiments, the bolus of oxygen delivered for the breath has a second volume that is less than the first volume of oxygen.

Optionally, the method may further include detecting the beginning of the inspiratory phase of the breath has been initiated by the patient. In such embodiments, the method may further include initiating delivery of the bolus of oxygen to the patient circuit in response to having detected the beginning of the inspiratory phase of the breath has been initiated by the patient.

The method may be used with an oxygen source connected to a valve. In such embodiments, delivering the bolus of oxygen at or before the beginning of the inspiratory phase of the breath includes opening the valve to thereby allow a flow of oxygen from the oxygen source to the patient circuit. Further, terminating the delivery of the bolus of oxygen before the end of the inspiratory phase of the breath includes closing the valve to thereby discontinue the flow of oxygen from the oxygen source to the patient circuit.

The method may be used with an oxygen generator connected to the oxygen source. In such embodiments, the oxygen source is configured to store oxygen generated by the oxygen generator, the method further includes detecting a value including at least one of a concentration of the oxygen stored by the oxygen source and a pressure of the oxygen stored by the oxygen source, determining if the detected value is below a threshold value, operating the oxygen generator when the detected value is determined to be below the threshold value, and delivering oxygen generated by the oxygen generator to the oxygen source.

The method may be used with a user specified total tidal volume. In such embodiments, the breathing gases delivered for the breath have a first volume, the bolus of oxygen delivered for the breath has a second volume, and combined the first and second volumes are substantially equal to the user specified total tidal volume.

The method may be used with a user specified peak inspiratory pressure value. In such embodiments, a combined pressure of the breathing gases and the bolus of oxygen delivered for the breath does not exceed the user specified peak inspiratory pressure value.

The method may be used with a breathing gases delivery conduit and an oxygen delivery conduit. The breathing gases delivery conduit has a breathing gases output located at a first end portion of the patient circuit away from the patient connection. The oxygen delivery conduit has an oxygen output located at a second end portion of the patient circuit adjacent to the patient connection. Delivering the breathing gases to the patient circuit may include providing the breathing gases to the breathing gases output via the breathing gases delivery conduit. Further, delivering the bolus of oxygen to the patient circuit includes providing the bolus of oxygen to the oxygen output via oxygen delivery conduit, to thereby isolate the bolus of oxygen delivered for the breath from the breathing gases delivered for the breath along at least a majority portion of the patient circuit prior to the patient connection.

Optionally, the patient circuit includes a breathing gases delivery conduit and an oxygen delivery conduit. In such embodiments, delivering the breathing gases to the patient circuit includes providing the breathing gases to the breathing gases delivery conduit, which delivers the breathing gases to the patient connection. Further, delivering the bolus of oxygen to the patient circuit includes providing the bolus of oxygen to the oxygen delivery conduit, which delivers the bolus of oxygen to the patient connection, thereby isolating the bolus of oxygen delivered for the breath from the breathing gases delivered for the breath along at least a portion of the patient circuit prior to the patient connection. Optionally, the bolus of oxygen exits the oxygen delivery conduit and enters the breathing gases delivery conduit at a location adjacent to the patient connection. Optionally, the bolus of oxygen exits the oxygen delivery conduit and enters the breathing gases delivery conduit at a location within about two centimeters of the patient connection.

The method may be used with a compressor operable to compress breathing gases. In such embodiments, delivering breathing gases to the patient circuit includes delivering at least a portion of the breathing gases compressed by the compressor.

An embodiment includes a ventilator device for use with an oxygen source and a patient circuit. The patient circuit is configured to receive breathing gases and oxygen to provide a breath to a human patient having a patient connection couplable to the patient circuit. The breath has an inspiratory phase with a beginning and an end. The ventilator device includes a compressor configured to deliver breathing gases to the patient circuit, and a control system configured to (a) allow the oxygen to flow from the oxygen source to the patient circuit at or before a beginning of an inspiratory phase of a breath, (b) prevent the oxygen from flowing from the oxygen source to the patient circuit before an end of the inspiratory phase of the breath, and (c) cause the compressor to deliver the breathing gases to the patient circuit before the end of the inspiratory phase of the breath.

Optionally, the ventilator device may include an input configured to receive a user specified total tidal volume. In such embodiments, the breathing gases delivered to the patient circuit for the breath have a first volume, the oxygen allowed to flow to the patient circuit for the breath has a second volume, and combined the first and second volumes are substantially equal to the user specified total tidal volume.

Optionally, the ventilator device may include an input configured to receive a user specified peak inspiratory pressure value. In such embodiments, a combined pressure of the breathing gases delivered to the patient circuit and the oxygen allowed to flow to the patient circuit for the breath does not exceed the user specified peak inspiratory pressure value.

Another embodiment includes a ventilator device for use with a patient circuit. The patient circuit is configured to receive breathing gases and oxygen to provide a breath to a human patient having a patient connection couplable to the patient circuit. The breath has an inspiratory phase with a beginning and an end. The ventilator device includes a compressor configured to deliver breathing gases to the patient circuit, a patient oxygen outlet couplable to the patient circuit, an oxygen source configured to deliver oxygen to the patient circuit, and a control system configured to (a) allow the oxygen to flow from the oxygen source to the patient circuit at or before a beginning of an inspiratory phase of a breath, (b) prevent the oxygen from flowing from the oxygen source to the patient circuit before an end of the inspiratory phase of the breath, and (c) cause the compressor to deliver the breathing gases to the patient circuit before the end of the inspiratory phase of the breath.

Optionally, the ventilator device may include an input configured to receive a user specified total tidal volume. In such embodiments, the breathing gases delivered to the patient circuit for the breath have a first volume, the oxygen allowed to flow to the patient circuit for the breath has a second volume, and combined the first and second volumes are substantially equal to the user specified total tidal volume.

Optionally, the ventilator device may include an input configured to receive a user specified peak inspiratory pressure value. In such embodiments, a combined pressure of the breathing gases delivered to the patient circuit and the oxygen allowed to flow to the patient circuit for the breath does not exceed the user specified peak inspiratory pressure value.

An embodiment includes a ventilation system for use with a human patient having a patient connection couplable to a patient circuit. The system includes a control system, an oxygen source configured to deliver oxygen to a patient oxygen outlet couplable to the patient circuit, and a compressor configured to deliver breathing gases to a ventilator connection couplable to the patient circuit. The ventilator connection is different from the patient oxygen outlet. The control system is configured to identify an inspiratory phase of a breath, and instruct the oxygen source to deliver the oxygen to the patient oxygen outlet before or during the inspiratory phase. The oxygen source is configured to deliver the oxygen to the patient oxygen outlet in response to the instruction to deliver the oxygen to the patient oxygen outlet. The control system is further configured to instruct the compressor to deliver the breathing gases to the ventilator connection during the inspiratory phase. The compressor is configured to deliver the breathing gases to the ventilator connection in response to the instruction to deliver the breathing gases to the ventilator connection.

Optionally, the compressor and the ventilator connection may be components of a ventilator, and the oxygen source may be external to the ventilator.

Optionally, the oxygen source is an internal oxygen source of a ventilator. The internal oxygen source has an oxygen inlet in fluid communication with the internal oxygen source. In such embodiments, the ventilation system may include an external oxygen source in fluid communication with the oxygen inlet to deliver oxygen from the external oxygen source to the internal oxygen source.

Optionally, the ventilation system also includes an oxygen generator in fluid communication with the oxygen source, the oxygen generator delivering oxygen to the oxygen source. The compressor, the oxygen source, and the oxygen generator may each be components of a ventilator. Alternatively, the compressor and the oxygen source are each components of a ventilator, and the oxygen generator is external to the ventilator.

Optionally, the ventilation system also includes a user interface having an input configured to receive a user specified total tidal volume. The user interface is configured to provide the user specified total tidal volume to the control system. The control system is configured to determine a first volume and a second volume. In such embodiments, the breathing gases delivered for the breath have the first volume, the oxygen delivered for the breath has the second volume, and combined the first and second volumes are substantially equal to the user specified total tidal volume.

Optionally, the ventilation system also includes a user interface having an input configured to receive a user specified peak inspiratory pressure value. In such embodiments, the user interface is configured to provide the user specified peak inspiratory pressure value to the control system, and a combined pressure of the breathing gases and the oxygen delivered for the breath does not exceed the user specified peak inspiratory pressure value.

BRIEF DESCRIPTION OF THE SEVERAL VIEWS OF THE DRAWING(S)

Like reference numerals have been used in the figures to identify like components.

DETAILED DESCRIPTION OF THE INVENTION

Figure 1:
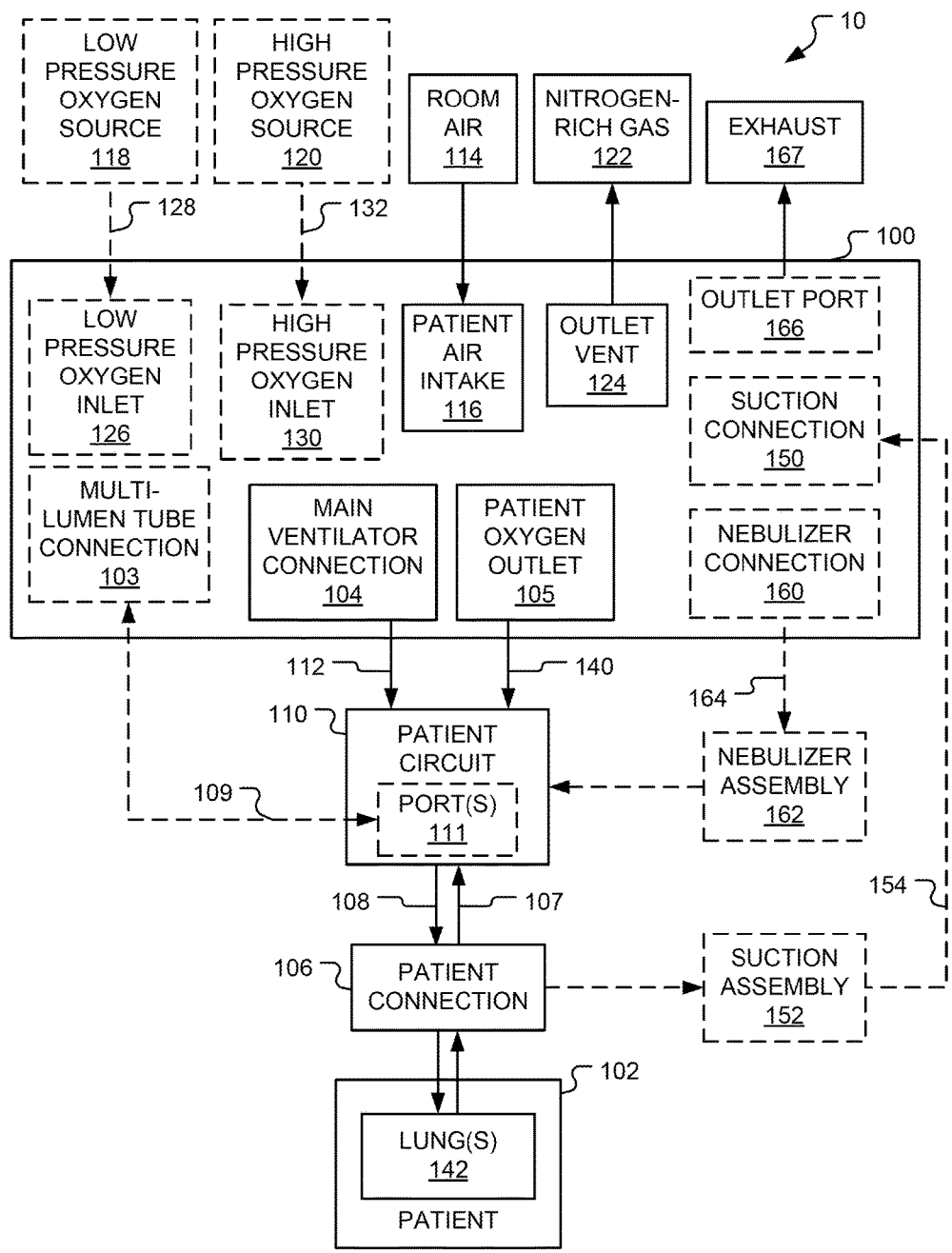
FIG. 1 is a block diagram illustrating an exemplary system that includes a ventilator for use by a human patient.

FIG. 1 is a block diagram illustrating an exemplary system 10 that includes a ventilator 100 for use by a patient 102. The ventilator 100 may be configured to provide both traditional volume controlled ventilation and pressure controlled ventilation. The ventilator 100 has an optional multi-lumen tube connection 103, a main ventilator connection 104, and an patient oxygen outlet 105. The patient 102 has a patient connection 106 (e.g., a tracheal tube, a nasal mask, a mouthpiece, and the like) that is connectable to the main ventilator connection 104 and/or the patient oxygen outlet 105 by a patient circuit 110.

As will be described below, the patient circuit 110 may be implemented as an active patient circuit or a passive patient circuit. Optionally, when the patient circuit 110 is implemented as an active patient circuit, the patient circuit 110 may include one or more ports 111 configured to be connected to the optional multi-lumen tube connection 103. The port(s) 111 allow one or more pressure signals 109 to flow between the optional multi-lumen tube connection 103 and the patient circuit 110. As is apparent to those of ordinary skill in the art, a pressure signal may be characterized as gas(es) obtained from a fluid (and/or gas) source for which a pressure is to be measured. The gas(es) obtained are at the same pressure as the fluid (and/or gas) source.

The main ventilator connection 104 is configured to provide gases 112 that include room air 114 optionally mixed with oxygen. While identified as being "room air," those of ordinary skill in the art appreciate that the room air 114 may include air obtained from any source external to the ventilator 100. The air 114 is received by the ventilator 100 via a patient air intake 116. The oxygen that is optionally mixed with the air 114 may be generated internally by the ventilator 100 and/or received from an optional low pressure oxygen source 118 (e.g., an oxygen concentrator), and/or an optional high pressure oxygen source 120. When the oxygen is generated internally, the ventilator 100 may output exhaust gases (e.g., nitrogen-rich gas 122) via an outlet vent 124. Optionally, the ventilator 100 may include a low pressure oxygen inlet 126 configured to be coupled to the optional low pressure oxygen source 118 and receive optional low pressure oxygen 128 therefrom. The ventilator 100 may include an optional high pressure oxygen inlet 130 configured to be coupled to the optional high pressure oxygen source 120 and receive optional high pressure oxygen 132 therefrom.

The patient oxygen outlet 105 is configured to provide doses or pulses of oxygen 140 to the patient connection 106 (via the patient circuit 110) that are synchronized with the patient's breathing. Unlike the gases 112 provided by the main ventilator connection 104, the pulses of oxygen 140 do not include the air 114.

The gases 112 and/or the pulses of oxygen 140 delivered to the patient circuit 110 are conducted thereby as inspiratory gases 108 to the patient connection 106, which at least in part conducts those gases into the patient's lung(s) 142. Whenever the patient exhales during the exhalation phase, exhaled gases 107 enter the patient circuit 110 via the patient connection 106. Thus, the patient circuit 110 may contain one or more of the following gases: the gases 112 provided by the ventilator 100, the pulses of oxygen 140, and the exhaled gases 107. For ease of illustration, the gases inside the patient circuit 110 will be referred to hereafter as "patient gases."

Optionally, the ventilator 100 includes a suction connection 150 configured to be coupled to an optional suction assembly 152. The ventilator 100 may provide suction 154 to the optional suction assembly 152 via the optional suction connection 150. The suction assembly 152 may be configured to be connected to the patient connection 106 and/or a suction catheter 812 (see FIG. 16) positionable inside the patient connection 106.

Referring to FIG. 1, optionally, the ventilator 100 includes a nebulizer connection 160 configured to be coupled to an optional nebulizer assembly 162. The ventilator 100 may provide gases 164 (e.g., the air 114) to the optional nebulizer assembly 162 via the optional nebulizer connection 160. The optional nebulizer assembly 162 may be configured to be connected to the patient circuit 110. However, this is not a requirement.

Optionally, the ventilator 100 may include an outlet port 166 through which exhaust 167 may exit from the ventilator 100.

The ventilator 100 may be configured to be portable and powered by an internal battery (not shown) and/or an external power source (not shown) such as a conventional wall outlet.

Passive Patient Circuits

Figure 2A:
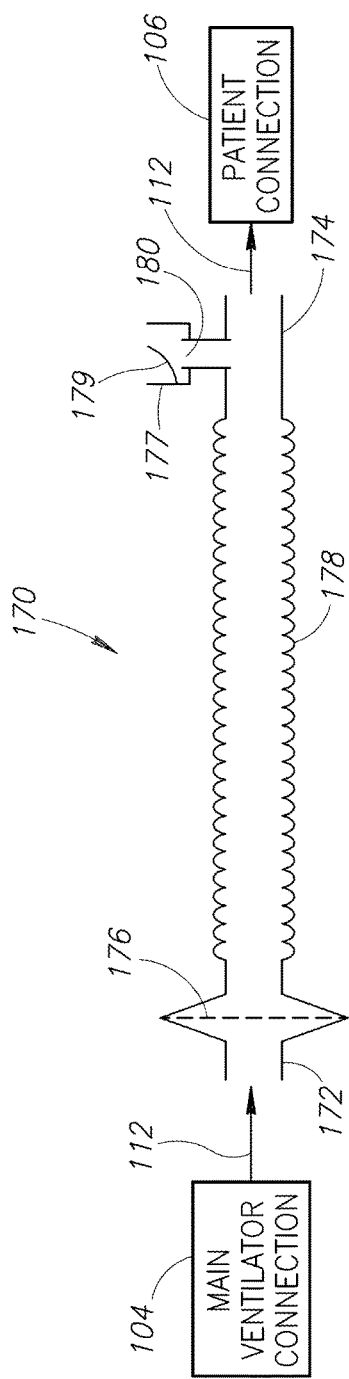
FIG. 2A is an illustration of a first embodiment of a passive patient circuit for use with the ventilator of FIG. 1.

FIG. 2A is an illustration of a first embodiment of a passive patient circuit 170 that may be used to implement the patient circuit 110. Referring to FIG. 2A, the passive patient circuit 170 has a first end portion 172 opposite a second end portion 174. The first end portion 172 is configured to be connected or coupled (e.g., directly or using a hose, flow line, conduit, or tube) to the main ventilator connection 104. The second end portion 174 is configured to be connected or coupled to the patient connection 106 (e.g., directly or using a hose, flow line, conduit, or tube). The passive patient circuit 170 conducts the gases 112 (that include the air 114 optionally mixed with oxygen) from the main ventilator connection 104 into the patient connection 106.

In the embodiment illustrated, the passive patient circuit 170 includes an optional bacterial filter 176, a leak valve 177, and a flexible tube segment 178. The optional bacterial filter 176 may be positioned between the first end portion 172 and the flexible tube segment 178. The gases 112 may flow through the optional bacterial filter 176 and on to the patient connection 106. When present, the bacterial filter 176 helps prevent bacteria (e.g., received from the patient connection 106) from entering the ventilator 100 (via the main ventilator connection 104).

The leak valve 177 is coupled to the flexible tube segment 178 near the second end portion 174. The leak valve 177 is configured to allow gases to flow out of the passive patient circuit 170 and into the environment outside the passive patient circuit 170. The leak valve 177 may be implemented as a conventional fixed leak valve configured to allow at most a threshold amount of pressure inside the passive patient circuit 170 during both the inspiratory and exhalation phases.

The leak valve 177 may be implemented as a positive pressure valve that allows a portion of the patient gases to flow out of the passive patient circuit 170 and into the environment outside the passive patient circuit 170 whenever the pressure inside the passive patient circuit 170 is above the threshold amount (e.g., environmental pressure). The leak valve 177 includes a flexible member or flap 179 that covers and seals an outlet opening 180 when the pressure inside the passive patient circuit 170 is below the threshold amount. Thus, the leak valve 177 is closed when the pressure inside the passive patient circuit 170 is below the threshold amount.

On the other hand, the flap 179 is configured to be pushed outwardly and away from the outlet opening 180 when the pressure inside the passive patient circuit 170 exceeds the threshold amount (e.g., environmental pressure). Thus, the leak valve 177 is open when the pressure inside the passive patient circuit 170 is above the threshold amount. Under normal operating circumstances, the leak valve 177 is open during both the inspiratory and exhalation phases. This means a portion of the patient gases inside the passive patient circuit 170 flow out of the passive patient circuit 170 through the outlet opening 180 and into the environment outside the passive patient circuit 170 during both the inspiratory and exhalation phases.

Figure 2B:
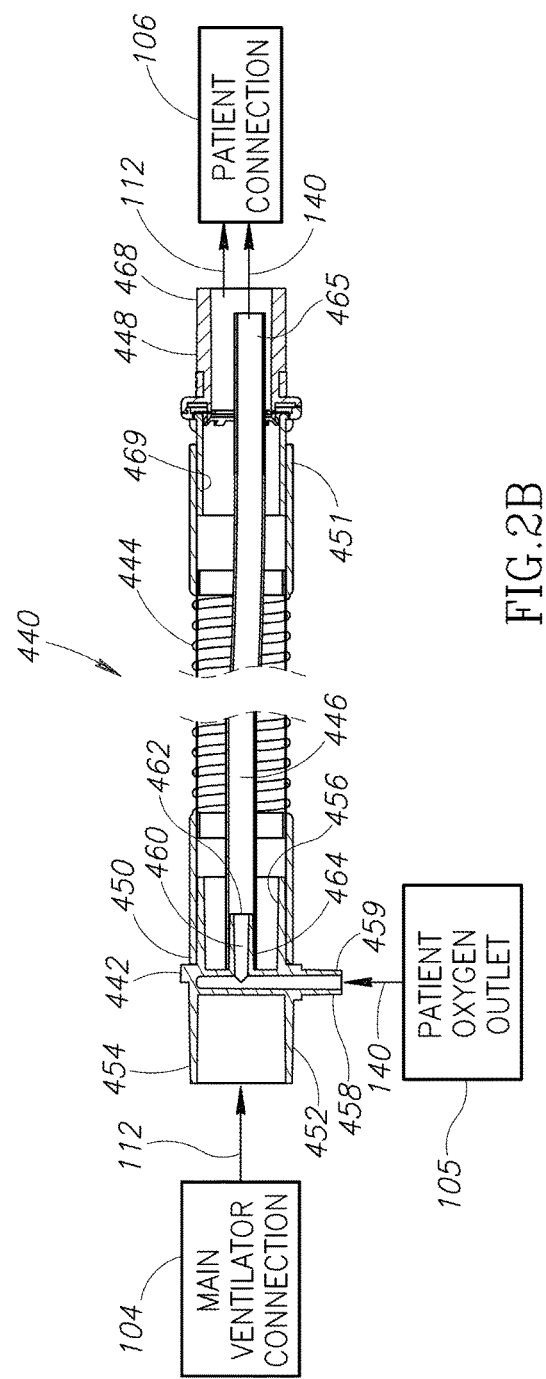
FIG. 2B is a cross-sectional view of a second embodiment of a passive patient circuit for use with the ventilator of FIG. 1.

FIG. 2B is an illustration of a second embodiment of a passive patient circuit 440 that may be used to implement the patient circuit 110. The passive patient circuit 440 includes a connector 442, a flexible tube segment 444, an open-ended oxygen pulse delivery tube 446, and a valve assembly 448. The flexible tube segment 444 may be implemented using a conventional corrugated or expanding ventilation hose or tubing (e.g., circuit tubing). The flexible tube segment 444 has a first end portion 450 opposite a second end portion 451. The first end portion 450 is configured to be connected or coupled to the connector 442. The second end portion 451 is configured to be connected or coupled to the valve assembly 448.

The connector 442 has a generally tube-shaped connector housing 452 with a first end portion 454 configured to be connected to the main ventilator connection 104 (e.g., directly or using a hose, flow line, conduit, or tube) and to receive the gases 112 (that include the air 114 optionally mixed with oxygen) from the main ventilator connection 104. Optionally, the bacterial filter 176 (see FIG. 2A) may be positioned between the connector 442 and the main ventilator connection 104. In such embodiments, the gases 112 flow through the bacterial filter 176 on their way to the connector 442. The bacterial filter 176 helps prevent bacteria (e.g., received from the patient connection 106) from entering the ventilator 100 (via the main ventilator connection 104).

The connector housing 452 has a second end portion 456 configured to be coupled to the first end portion 450 of the flexible tube segment 444 and to provide the gases 112 received by the first end portion 454 to the flexible tube segment 444. The flexible tube segment 444 conducts the gases 112 to the valve assembly 448.

The connector 442 includes a hollow tube section 458 that extends outwardly from the connector housing 452. In the embodiment illustrated, the tube section 458 is substantially transverse to the connector housing 452. However, this is not a requirement. The tube section 458 has an open free end portion 459 configured to be connected to the patient oxygen outlet 105 (e.g., directly or using a hose, flow line, conduit, or tube) and to receive the pulses of oxygen 140 therefrom. Inside the connector housing 452, the tube section 458 is connected to the oxygen pulse delivery tube 446 and provides the pulses of oxygen 140 thereto. In the embodiment illustrated, the tube section 458 is connected to or includes a branch tube 460 that extends longitudinally inside the connector housing 452. The branch tube 460 has an open free end 462 configured to be coupled to the oxygen pulse delivery tube 446 and provide the pulses of oxygen 140 thereto. While the tube section 458 extends into the connector housing 452, the tube section 458 only partially obstructs the flow of the gases 112 through the connector housing 452. In other words, the gases 112 pass by or alongside the tube section 458 and the branch tube 460, if present.

In the embodiment illustrated, the oxygen pulse delivery tube 446 extends through the flexible tube segment 444 and at least part way into the valve assembly 448. Thus, the oxygen pulse delivery tube 446 isolates the pulses of oxygen 140 from the gases in the flexible tube segment 444 along a majority portion of the passive patient circuit 440. The oxygen pulse delivery tube 446 has a first end portion 464 configured to be coupled to the branch tube 460. The oxygen pulse delivery tube 446 has a second end portion 465 that terminates at or near the patient connection 106. By way of a non-limiting example, the second end portion 465 may terminate within about two centimeters of the patient connection 106. The oxygen pulse delivery tube 446 conducts the pulses of oxygen 140 from the branch tube 460 to the patient connection 106. At the same time, the passive patient circuit 440 conducts the gases 112 (that include the air 114 optionally mixed with oxygen) from the main ventilator connection 104 into the patient connection 106.

In alternate embodiments, the oxygen pulse delivery tube 446 may be connected to the patient oxygen outlet 105 (e.g., directly or using a hose, flow line, conduit, or tube) to receive the pulses of oxygen 140 from the patient oxygen outlet 105. In such embodiments, the oxygen pulse delivery tube 446 may extend along the outside of the flexible tube segment 444. The second end portion 465 of the oxygen pulse delivery tube 446 may be connected to a portion of the passive patient circuit 440 at or near the patient connection 106 to provide the pulses of oxygen 140 from the branch tube 460 to the patient connection 106.

Figure 2C:
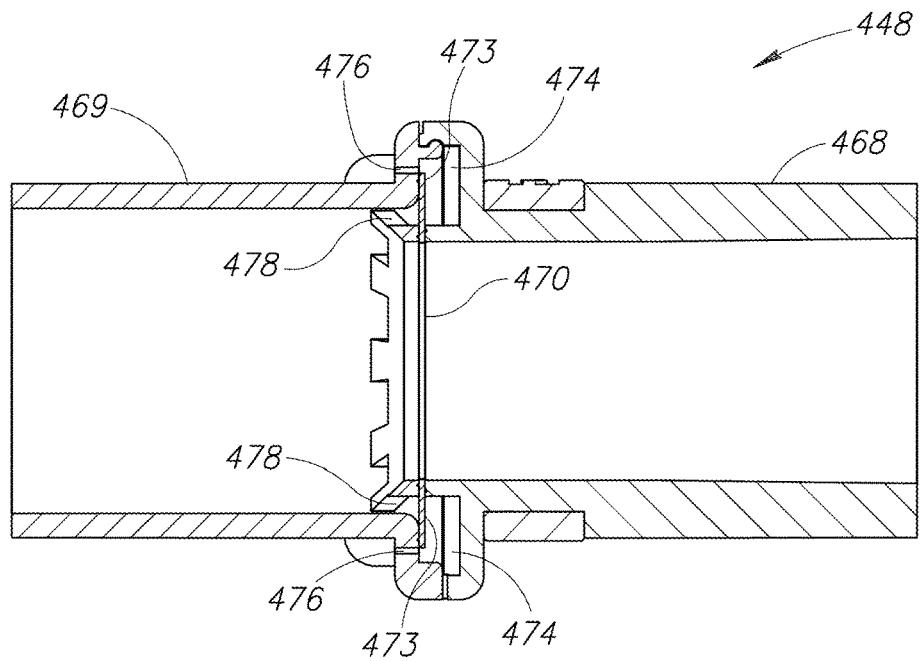
FIG. 2C is an enlarged cross-sectional view of a valve assembly of the passive patient circuit of FIG. 2B illustrated in a closed configuration.
Figure 2D:
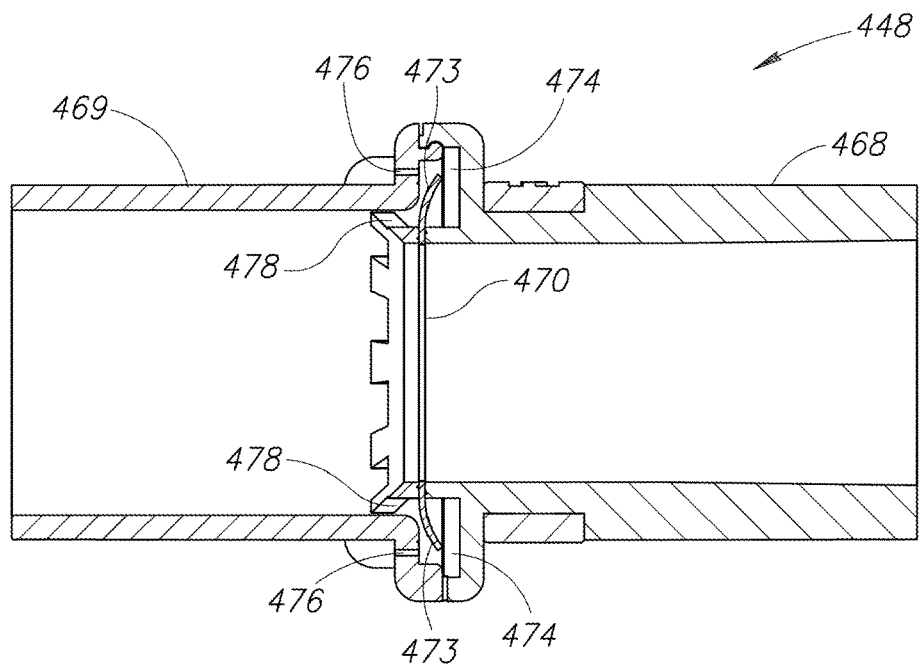
FIG. 2D is an enlarged cross-sectional view of the valve assembly of the passive patient circuit of FIG. 2B illustrated in an open configuration.
Figure 2E:
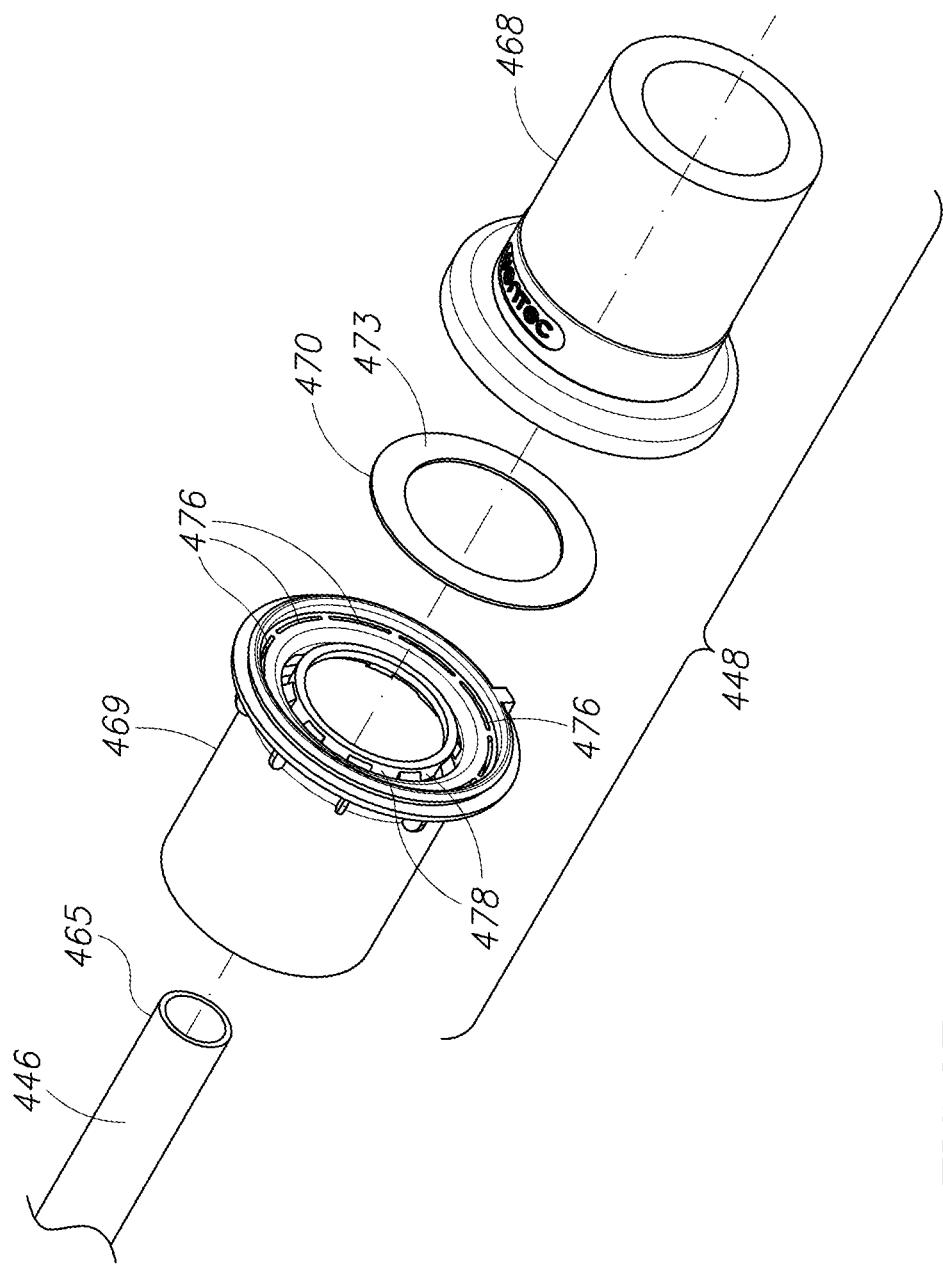
FIG. 2E is an exploded view of a valve assembly of the passive patient circuit of FIG. 2B.

FIGS. 2C-2E illustrate exemplary components of the valve assembly 448. In the embodiment illustrated, the valve assembly 448 includes a first valve housing 468, a second valve housing 469, and a flexible ring-shaped leaf 470.

The first valve housing 468 is configured to be coupled to the patient connection 106 (see FIG. 2A) and the second valve housing 469 is configured to be coupled to the second end portion 451 of the flexible tube segment 444. The first and second valve housings 468 and 469 are configured to be coupled together with the ring-shaped leaf 470 positioned therebetween. A peripheral portion 473 of the leaf 470 is positioned within a ring-shaped chamber 474 defined by the first and second valve housings 468 and 469. One or more openings 476 are formed in the second valve housing 469 and connect the chamber 474 with the environment outside the passive patient circuit 440 (see FIG. 2A). Additionally, one or more openings 478 are formed in the second valve housing 469 and connect the patient gases inside the passive patient circuit 440 (see FIG. 2A) with the chamber 474.

Like the flap 179 (see FIG. 2A), the peripheral portion 473 of the leaf 470 is configured to transition or deflect from a closed position (see FIG. 2C) and an open position (see FIG. 2D) when the pressure inside the passive patient circuit 440 (see FIG. 2A) exceeds the threshold amount (e.g., environmental pressure). When the peripheral portion 473 of the leaf 470 is in the closed position depicted in FIG. 2C, the leaf 470 blocks off the one or more openings 478 and isolates the chamber 474 from the environment inside the passive patient circuit 440 (see FIG. 2A). On the other hand, when the peripheral portion 473 of the leaf 470 is in the open position depicted in FIG. 2D, the leaf 470 no longer blocks off the one or more openings 478 and allows the chamber 474 to communicate with the patient gases inside and outside the passive patient circuit 440 (see FIG. 2A). Thus, gases may exit the interior of the passive patient circuit 440 (see FIG. 2A) through the opening(s) 478, the chamber 474, and the opening(s) 476.

During the inspiratory phase, the ventilator 100 adjusts the pressure inside the passive patient circuit 440 to achieve a preset inspiratory pressure, which places or maintains the leaf 470 in the open position. Some of the patient gases flow to the patient 102 (see FIG. 1), and some of the patient gases flow out through the openings 476.

During the exhalation phase, the ventilator 100 adjusts the pressure inside the passive patient circuit 440 to achieve a baseline or positive end-expiratory pressure ("PEEP"), which places or maintains the leaf 470 in the open position. Some of the exhaled gases 107 (see FIG. 1) from the patient 102 flow out through the openings 476, and some of the exhaled gases 107 flow into the passive patient circuit 440 (e.g., into the flexible tube segment 444).

The breath 102 may pause between the end of the exhalation phase and the beginning of the inspiratory phase. This pause may be characterized as a dead time that occurs between the phases. During a pause, the ventilator 100 adjusts the pressure inside the passive patient circuit 440 to PEEP, which places or maintains the leaf 470 in the open position, and causes the flow of the gases 112 from the ventilator 100 to flow out of the passive patient circuit 440 through the openings 476. Also, during this time, at least a portion of the exhaled gases 107 that flowed into the passive patient circuit 440 during the exhalation phase is "purged" out through the openings 476 by the forward moving flow of the gases 112 from the ventilator 100.

The combined areas of the openings 476 may be characterized as providing a fixed orifice. Thus, the valve assembly 448 may be characterized as being a one-way valve with a fixed orifice. If the combined areas of the openings 476 is too large, most of the inspiratory flow will leak out through the openings 476, leaving little for the patient 102. Conversely, if the combined areas of the openings 476 is too small, the exhaled gases 107 will not be fully purged from the passive patient circuit 440 during the exhalation phase and the pause between the inspiratory and exhalation phases. By way of a non-limiting example, the valve assembly 448 may be configured to leak about 20-50 liters per minute ("LPM") when the pressure inside the passive patient circuit 440 is about 10 centimeters of water ("cmH20").

Active Patient Circuit

Figure 3A:
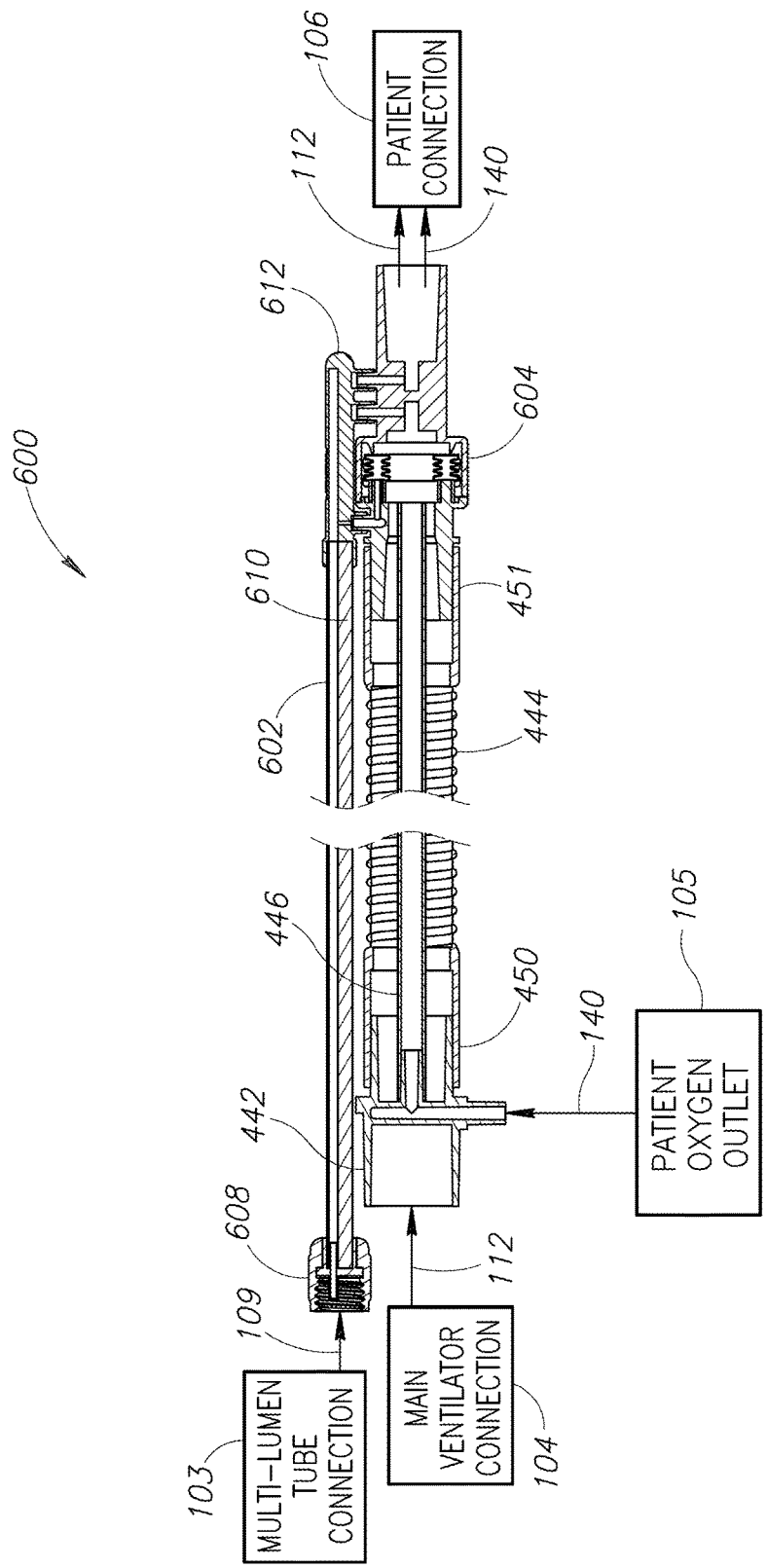
FIG. 3A is a cross-sectional view of an embodiment of an active patient circuit for use with the ventilator of FIG. 1.

FIG. 3A depicts an active patient circuit 600 that may be used to implement the patient circuit 110 (see FIG. 1). Referring to FIG. 3A, the active patient circuit 600 includes the connector 442, the flexible tube segment 444, the oxygen pulse delivery tube 446, a multi-lumen tube assembly 602, and an active exhalation valve assembly 604.

Like in the passive patient circuit 440 (see FIG. 2B), the connector 442 is coupled to both the first end portion 450 of the flexible tube segment 444 and the oxygen pulse delivery tube 446. The connector 442 receives the gases 112 and provides them to the flexible tube segment 444. Further, the connector 442 receives the pulses of oxygen 140 and provides them to the oxygen pulse delivery tube 446. The pulses of oxygen 140 exit the oxygen pulse delivery tube 446 at or near the patient connection 106. By way of a non-limiting example, the pulses of oxygen 140 may exit the oxygen pulse delivery tube 446 within about 10 centimeters of the patient connection 106. In the embodiment illustrated, the pulses of oxygen 140 exit the oxygen pulse delivery tube 446 at or near the active exhalation valve assembly 604.

Optionally, the bacterial filter 176 (see FIG. 2A) may be positioned between the connector 442 and the main ventilator connection 104. In such embodiments, the gases 112 flow through the bacterial filter 176 on their way to the connector 442. When present, the bacterial filter 176 helps prevent bacteria (e.g., received from the patient connection 106) from entering the ventilator 100 (via the main ventilator connection 104).

The second end portion 451 of the flexible tube segment 444 is configured to be coupled to the active exhalation valve assembly 604. As mentioned above with respect to FIG. 1, the patient circuit 110 may include one or more ports 111 configured to allow the one or more pressure signals 109 to flow between the optional multi-lumen tube connection 103 and the patient circuit 110. Referring to FIG. 3C, in the embodiment illustrated, the ports 111 (see FIG. 1) include ports 111A-111C spaced apart from one another longitudinally. The ports 111A-111C are each formed in the active exhalation valve assembly 604. The port 111C is referred to hereafter as the pilot port 111C.

Figure 3B:
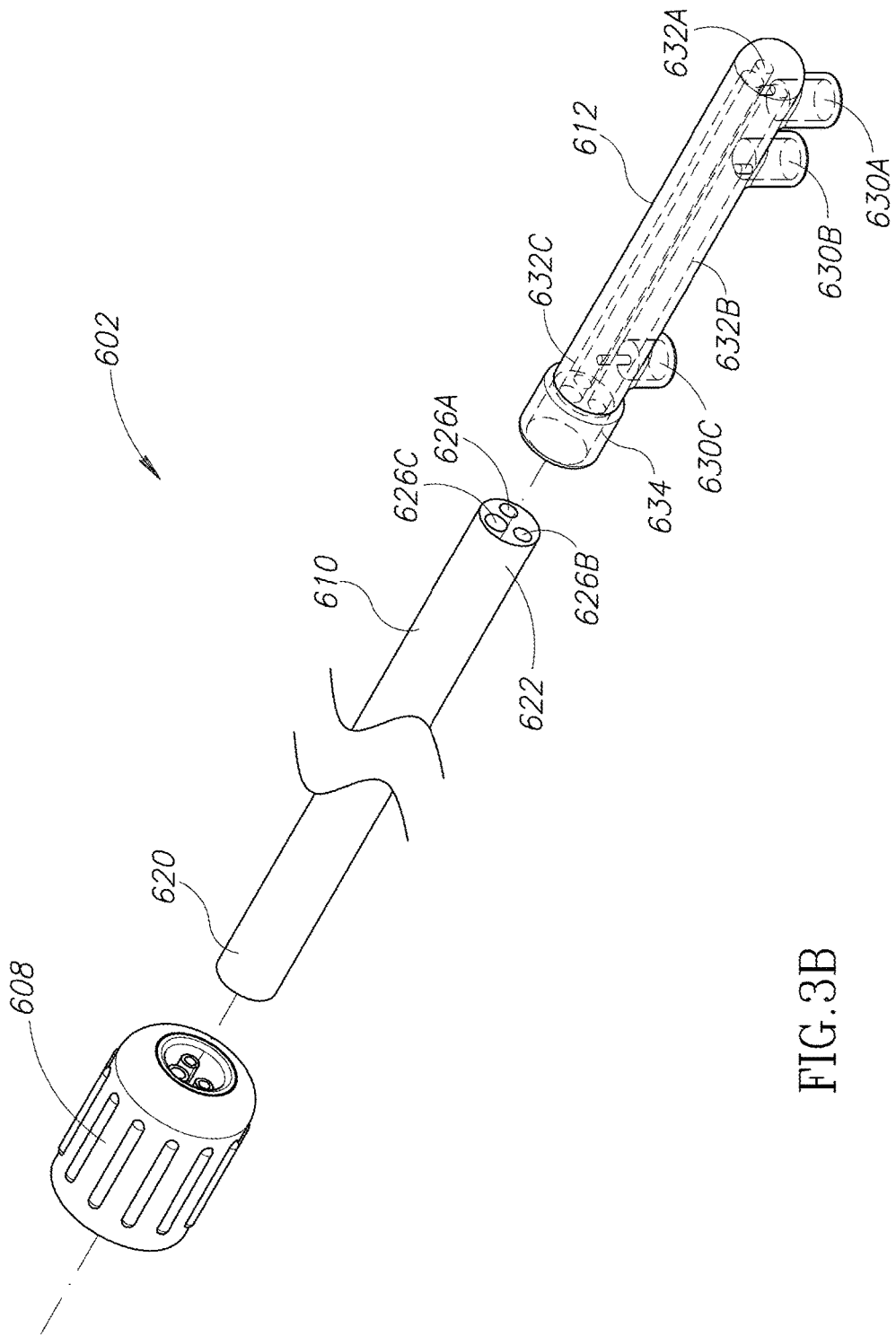
FIG. 3B is an exploded view of a multi-lumen tube assembly of the active patient circuit of FIG. 3A.
Figure 3C:
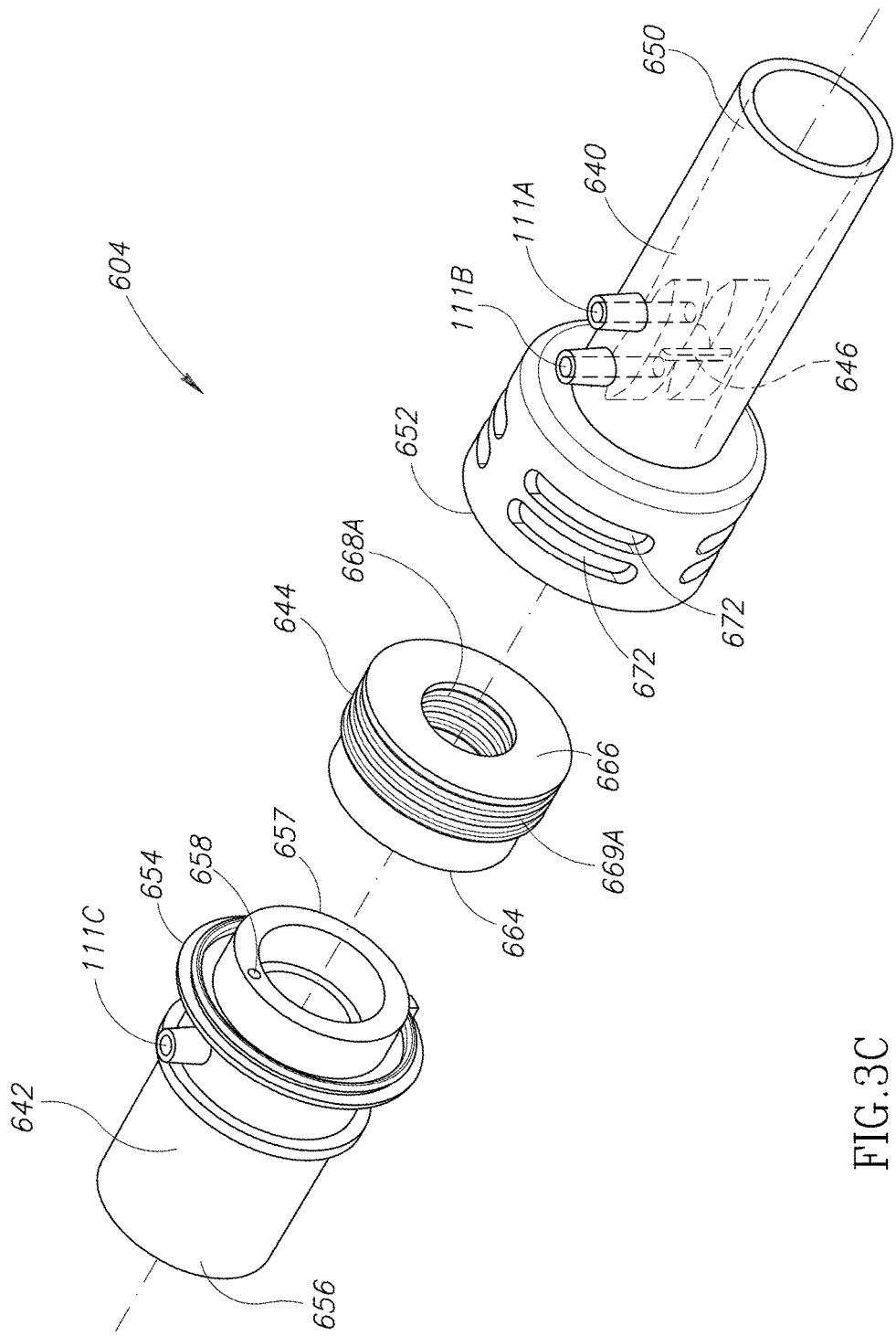
FIG. 3C is an exploded view of an active exhalation valve assembly of the active patient circuit of FIG. 3A.

FIG. 3B is exploded perspective view of the multi-lumen tube assembly 602. Referring to FIG. 3B, the multi-lumen tube assembly 602 includes a coupler 608, an elongated tube segment 610, and a connector member 612. The coupler 608 is configured to couple a first end portion 620 of the tube segment 610 to the optional multi-lumen tube connection 103 (see FIG. 3A). The tube segment 610 has a second end portion 622 opposite the first end portion 620. The second end portion 622 is connected to the connector member 612. Three separate and continuous open-ended channels 626A-626C extend longitudinally through the tube segment 610.

The connector member 612 has three connectors 630A-630C configured to connected to the ports 111A-111C (see FIG. 3C), respectively. The connectors 630A and 630B receive pressure signals 109A and 109B (see FIG. 5A), respectively, from the ports 111A and 111B, respectively. The connector 630C conducts a pressure signal 109C (see FIG. 5A) to and from the pilot port 111C.

Continuous channels 632A-632C extend from the connectors 630A-630C, respectively, to an end portion 634 of the connector member 612. When the connector member 612 is connected to the tube segment 610, the continuous channels 626A-626C of the tube segment 610 are aligned and communicate with the continuous channels 632A-632C, respectively. Thus, the multi-lumen tube assembly 602 may be used to conduct the separate pressure signals 109A and 109B, respectively, from the ports 111A and 111B, respectively, to the optional multi-lumen tube connection 103. Further, the multi-lumen tube assembly 602 may be used to conduct the pressure signal 109C to the pilot port 111C from the optional multi-lumen tube connection 103 and vice versa.

Referring to FIG. 3C, the active exhalation valve assembly 604 includes a first valve housing member 640, a double bellows member 644, and a second valve housing member 642. The ports 111A and 111B are formed in the first valve housing member 640 and extend laterally outwardly therefrom. The pilot port 111C is formed in the second valve housing member 642 and extends laterally outwardly therefrom.

Figure 3D:
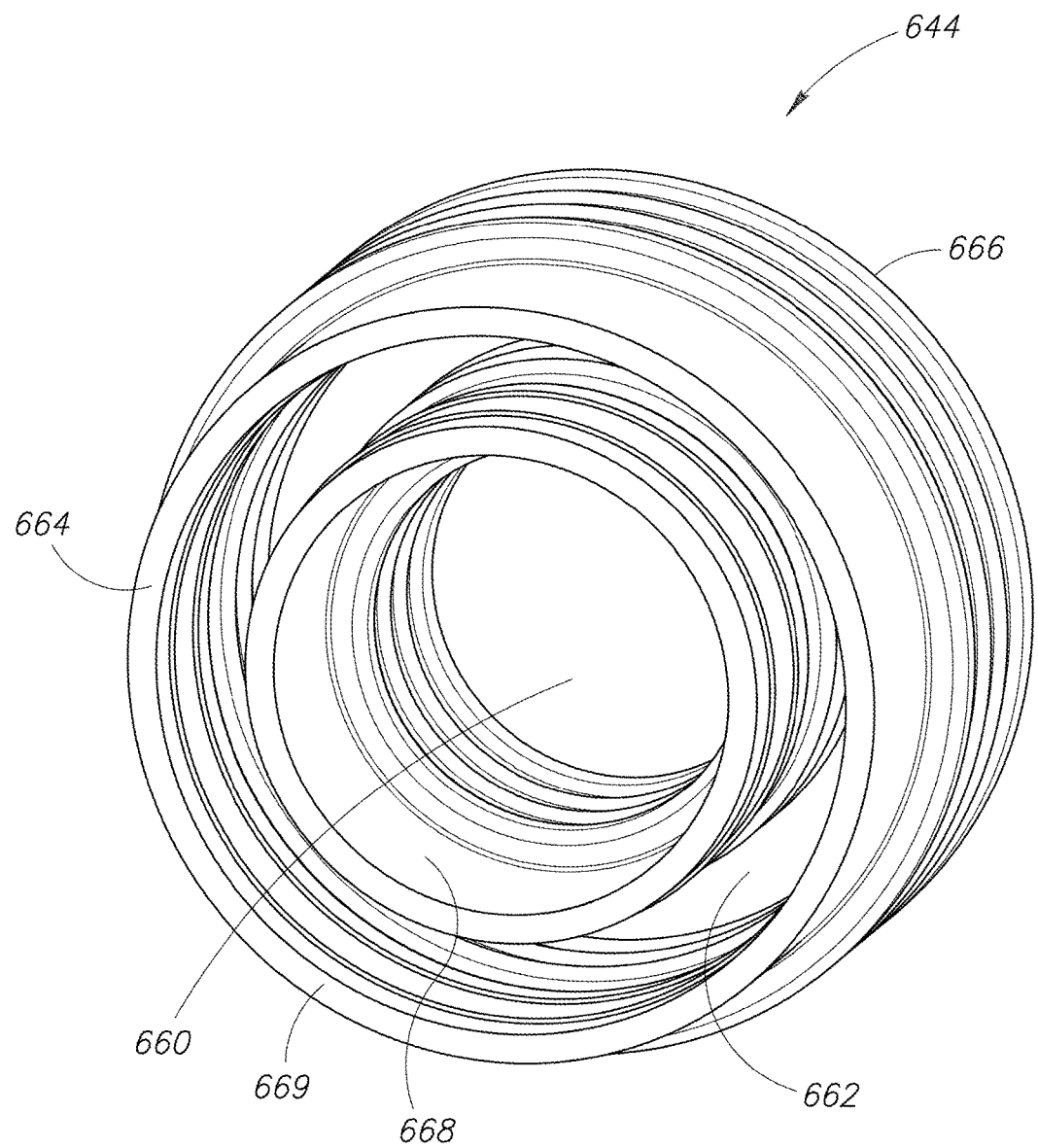
FIG. 3D is an enlarged perspective view of a double bellows member of the active exhalation valve assembly of FIG. 3C.
Figure 3E:
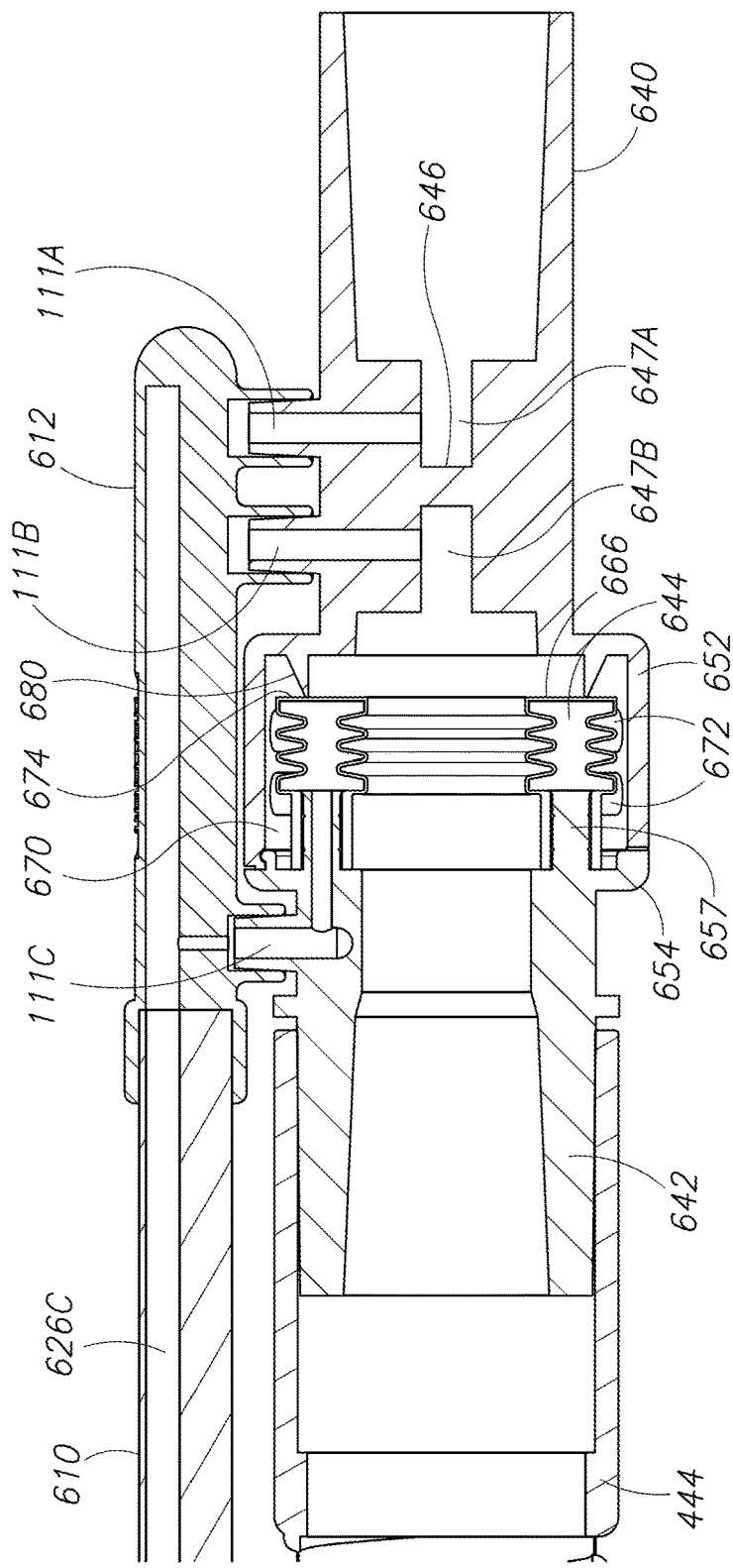
FIG. 3E is an enlarged cross-sectional view of the active patient circuit of FIG. 3A illustrated with the double bellows member of the active exhalation valve assembly in a closed position.
Figure 3F:
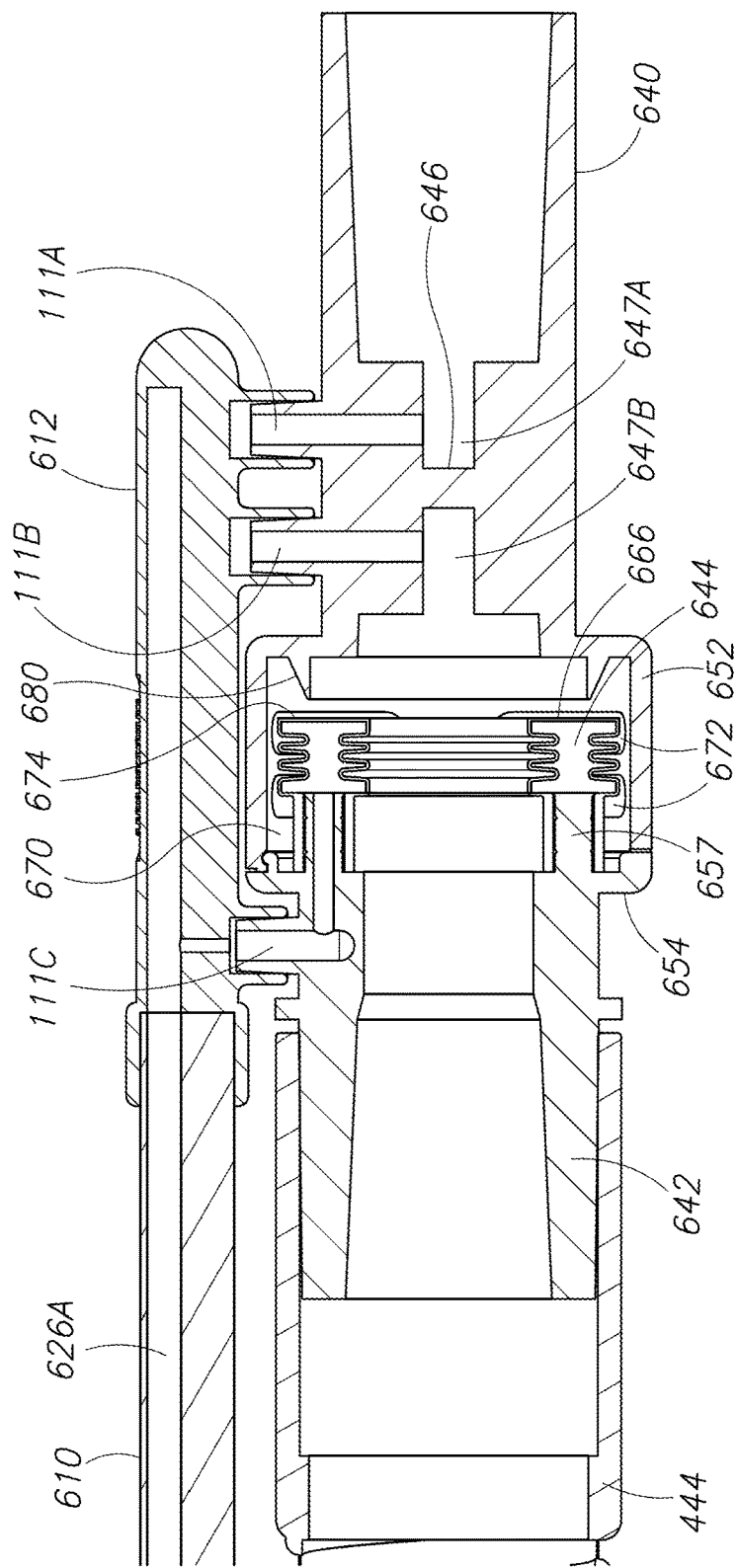
FIG. 3F is a first enlarged cross-sectional view of the active patient circuit of FIG. 3A illustrated with the double bellows member of the active exhalation valve assembly in an open position.

FIGS. 3E and 3F are enlarged longitudinal cross sectional views that each show a portion of the active patient circuit 600 that includes the active exhalation valve assembly 604. The oxygen pulse delivery tube 446 has been omitted from FIGS. 3E and 3F. In the embodiment illustrated, the first valve housing member 640 includes an internal obstruction 646 positioned between the ports 111A and 111B and configured to partially restrict flow through the first valve housing member 640. Further, as shown in FIGS. 3E and 3F, the interior of the first valve housing member 640 includes a first narrowed portion 647A that is adjacent to the obstruction 646 and the port 111A, and a second narrowed portion 647B that is adjacent to the obstruction 646 and the port 111B. Thus, the first and second narrowed portions 647A and 647B are positioned opposite one another longitudinally with respect to the obstruction 646 with the first narrowed portion 647A being nearer to the patient connection 106 (see FIG. 3A) than the second narrowed portion 647B. The ports 111A and 111B open into the first and second narrowed portions 647A and 647B, respectively.

Figure 3G:
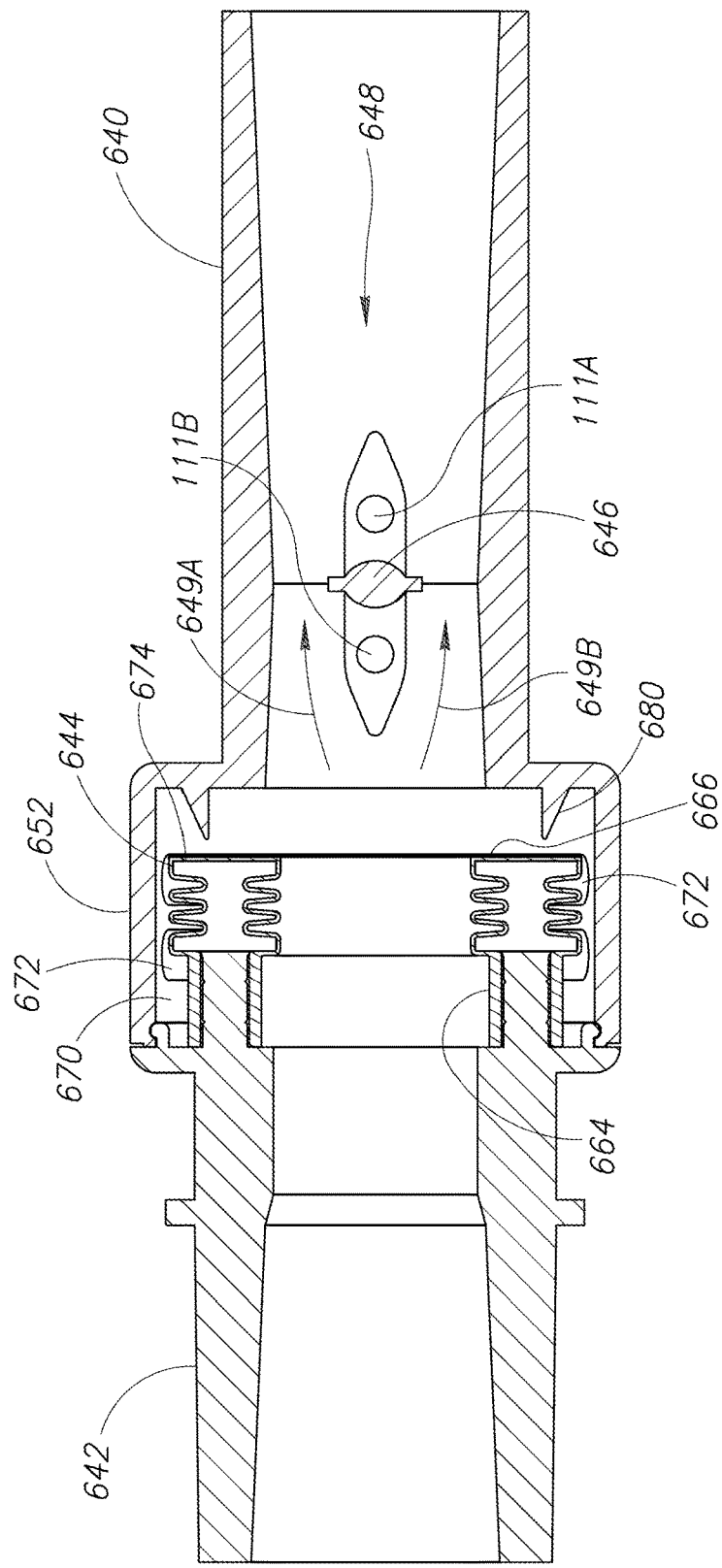
FIG. 3G is a second enlarged cross-sectional view of the active patient circuit of FIG. 3A illustrated with the double bellows member of the active exhalation valve assembly in the open position.

Referring to FIG. 3G, together the obstruction 646, the first and second narrowed portions 647A and 647B, and the ports 111A and 111B define an airway flow transducer 648 (e.g., a fixed orifice differential pressure type flow meter) inside the interior of the first valve housing member 640. During the inspiration phase, the gases 112 may flow around the obstruction 646 along flow paths identified by curved arrows 649A and 649B. During the exhalation phase, the exhaled gases 107 may flow around the obstruction 646 along flow paths opposite those identified by the curved arrows 649A and 649B.

Referring to FIG. 3C, the first valve housing member 640 has a first end portion 650 configured to be coupled to the patient connection 106 (see FIG. 3A) and a second end portion 652 configured to be coupled to the second valve housing member 642. The second valve housing member 642 has a first end portion 654 configured to be coupled to the second end portion 652 of the first valve housing member 640, and a second end portion 656 configured to be coupled to the second end portion 451 of the flexible tube segment 444. The first end portion 654 of the second valve housing member 642 has a generally cylindrical shaped bellows connector portion 657. An opening 658 of the pilot port 111C is formed in the bellows connector portion 657 of the second valve housing member 642.

Referring to FIG. 3D, the double bellows member 644 has a generally ring-like outer shape with a centrally located through-channel 660. The double bellows member 644 has a hollow interior 662 with a ring-shaped open end 664 opposite a ring-shaped closed end 666 (see FIG. 3C). In the embodiment illustrated, the double bellows member 644 has concertinaed inner and outer sidewalls 668 and 669. The inner sidewall 668 extends between the open end 664 and the closed end 666 along the centrally located through-channel 660. The outer sidewall 669 extends between the open end 664 and the closed end 666 and is spaced radially outwardly from the inner sidewall 668. The hollow interior 662 is defined between the inner and outer sidewalls 668 and 669. Each of the inner and outer sidewalls 668 and 669 have bellows portions 668A and 669A (see FIG. 3C), respectively, which each have an undulating longitudinal cross-sectional shape. In alternate embodiments, the inner and outer sidewalls 668 and 669 may include different numbers of convolutions that define a single convolute or more than two convolutes.

The open end 664 is configured to fit over the bellows connector portion 657 of the second valve housing member 642 like a sleeve. When the bellows connector portion 657 of the second valve housing member 642 is received inside the open end 664 of the double bellows member 644, the bellows portions 668A and 669A (see FIG. 3C) of the inner and outer sidewalls 668 and 669, respectively, are positioned adjacent to the bellows connector portion 657 of the second valve housing member 642. Thus, the opening 658 of the pilot port 111C is in communication with a portion of the hollow interior 662 positioned between the bellows portions 668A and 669A (see FIG. 3C) of the inner and outer sidewalls 668 and 669, respectively.

Referring to FIG. 3C, when the bellows connector portion 657 of the second valve housing member 642 is received inside the open end 664 of the double bellows member 644, the opening 658 of the pilot port 111C may provide the pressure signal 109C to the interior of the double bellows member 644.

Referring to FIGS. 3E and 3F, as mentioned above, the second end portion 652 of the first valve housing member 640 is configured to be coupled to the first end portion 654 of the second valve housing member 642. When so coupled together, a ring-shaped chamber 670 is defined between the second end portion 652 of the first valve housing member 640 and the first end portion 654 of the second valve housing member 642. One or more openings 672 (see FIG. 3C) are formed in the first valve housing member 640 and connect the chamber 670 with the environment outside the active patient circuit 600 (see FIG. 3A). The bellows portion 668A and 669A (see FIG. 3C) of the outer sidewall 669 and a peripheral portion 674 of the closed end 666 is positioned within the chamber 670.

The double bellows member 644 is constructed from a flexible material (e.g., silicone rubber and the like). The bellows portions 668A and 669A (see FIG. 3C) of the inner and outer sidewalls 668 and 669, respectively, are configured to compress to transition the closed end 666 from a closed position (see FIG. 3E) to an open position (see FIG. 3F). When the bellows portions 668A and 669A (see FIG. 3C) are not compressed, the closed end 666 is in the closed position depicted in FIG. 3E. In this configuration, the closed end 666 of the double bellows member 644 abuts a ring-shaped seat 680 formed in the first valve housing member 640 and defining a portion of the chamber 670. This seals the chamber 670 from the interior of the active patient circuit 600. On the other hand, when the bellows portions 668A and 669A (see FIG. 3C) are compressed toward the second valve housing member 642, the closed end 666 is in the open position depicted in FIG. 3F. In this configuration, the closed end 666 is spaced away from the seat 680. This opens the chamber 670 by connecting the chamber 670 with the inside of the active patient circuit 600. Thus, when the closed end 666 of the double bellows member 644 is in the open position, patient gases inside the active patient circuit 600 may exit therefrom through the chamber 670 and the opening(s) 672 (see FIG. 3C).

The closed end 666 of the double bellows member 644 is selectively moved between the open and closed positions by controlling the pressure inside the double bellows member 644 using the pilot port 111C. For example, the closed end 666 of the double bellows member 644 may be placed in the closed position (see FIG. 3E) during the inspiratory phase, and in the open position during the expiratory phase. In such embodiments, at the start of the inspiratory phase, the pilot port 111C provides a flow of gases (as the pressure signal 109C) having the same pressure as the gases 112 (provided to the active patient circuit 600) to the hollow interior 662 of the double bellows member 644. An area of the double bellows member 644 exposed to a pressure provided by the patient 102 (see FIG. 1) via the patient connection 106 is less than an area exposed to the pressure of the pressure signal 109C, so that even if the two pressures are equal, the closed end 666 of the double bellows member 644 will move to or remain in the closed position against the seat 680. At the end of the inspiratory phase, the pilot port 111C provides a flow of gases (as the pressure signal 109C) having a pilot pressure to the hollow interior 662 of the double bellows member 644. The pilot pressure is less than the pressure provided by the patient 102 (see FIG. 1) via the patient connection 106 and causes the closed end 666 of the double bellows member 644 to move to or remain in the open position (see FIG. 3F) spaced apart from the seat 680. Thus, the pressure inside the hollow interior 662 of the double bellows member 644 may be alternated between a closed pressure that is the same pressure as the gases 112 (provided to the active patient circuit 600), and an open pressure that is equal to the pilot pressure. If desired, the pressure inside the hollow interior 662 of the double bellows member 644 may be adjusted by allowing the flow of gases (in the pressure signal 109C) to flow from the hollow interior 662 to the pilot port 111C.

Ventilator

Figure 4:
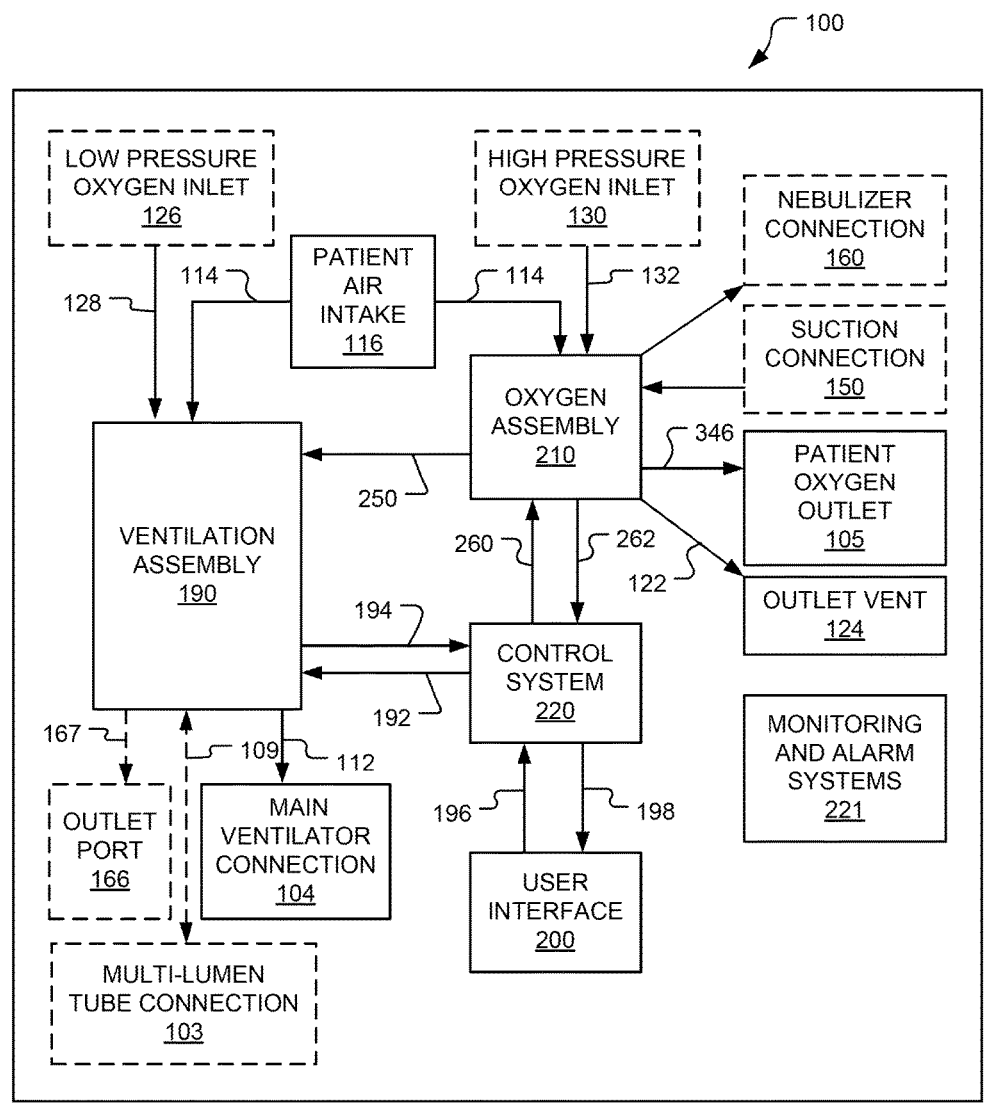
FIG. 4 is block diagram illustrating some exemplary components of the ventilator of FIG. 1.

FIG. 4 is a block diagram illustrating some exemplary components of the ventilator 100. Referring to FIG. 4, in addition to the components discussed with respect to FIG. 1, the ventilator 100 includes a ventilation assembly 190, a user interface 200, an oxygen assembly 210, a control system 220, and conventional monitoring and alarm systems 221. Because those of ordinary skill in the art are familiar with conventional monitoring and alarm systems 221, they will not be described in detail herein.

The control system 220 receives input information 196 (e.g., settings, parameter values, and the like) from the user interface 200, and provides output information 198 (e.g., performance information, status information, and the like) to the user interface 200. The user interface 200 is configured to receive input from a user (e.g., a caregiver, a clinician, and the like associated with the patient 102 depicted in FIG. 1) and provide that input to the control system 220 in the input information 196. The user interface 200 is also configured to display the output information 198 to the user.

As mentioned above, referring to FIG. 1, the patient circuit 110 may include the optional port(s) 111 configured to allow one or more pressure signals 109 to flow between the optional multi-lumen tube connection 103 and the patient circuit 110. Referring to FIG. 3, the optional multi-lumen tube connection 103 is configured to provide the pressure signal(s) 109 to the ventilation assembly 190.

As will be explained below, the ventilation assembly 190 may receive one or more control signals 192 from the control system 220, and the ventilation assembly 190 may provide one or more data signals 194 to the control system 220. Similarly, the oxygen assembly 210 may receive one or more control signals 260 from the control system 220, and the oxygen assembly 210 may provide one or more data signals 262 to the control system 220. The control signals 192 and 260 and the data signals 194 and 262 may be used by the control system 220 to monitor and/or control internal operations of the ventilator 100.

Ventilation Assembly

Figure 5A:
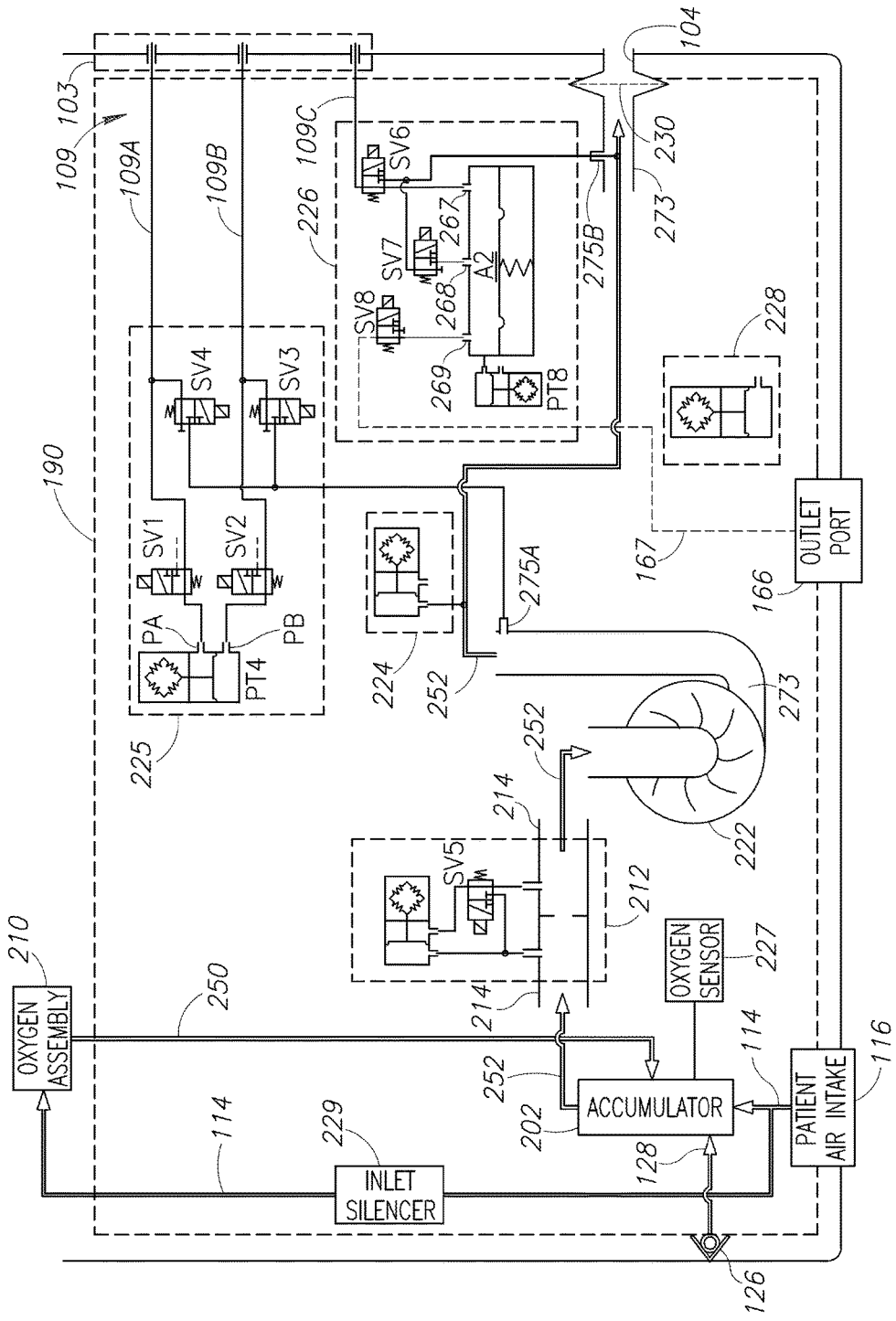
FIG. 5A is a schematic diagram illustrating some exemplary components of a ventilator assembly of the ventilator of FIG. 1.
Figure 5B:
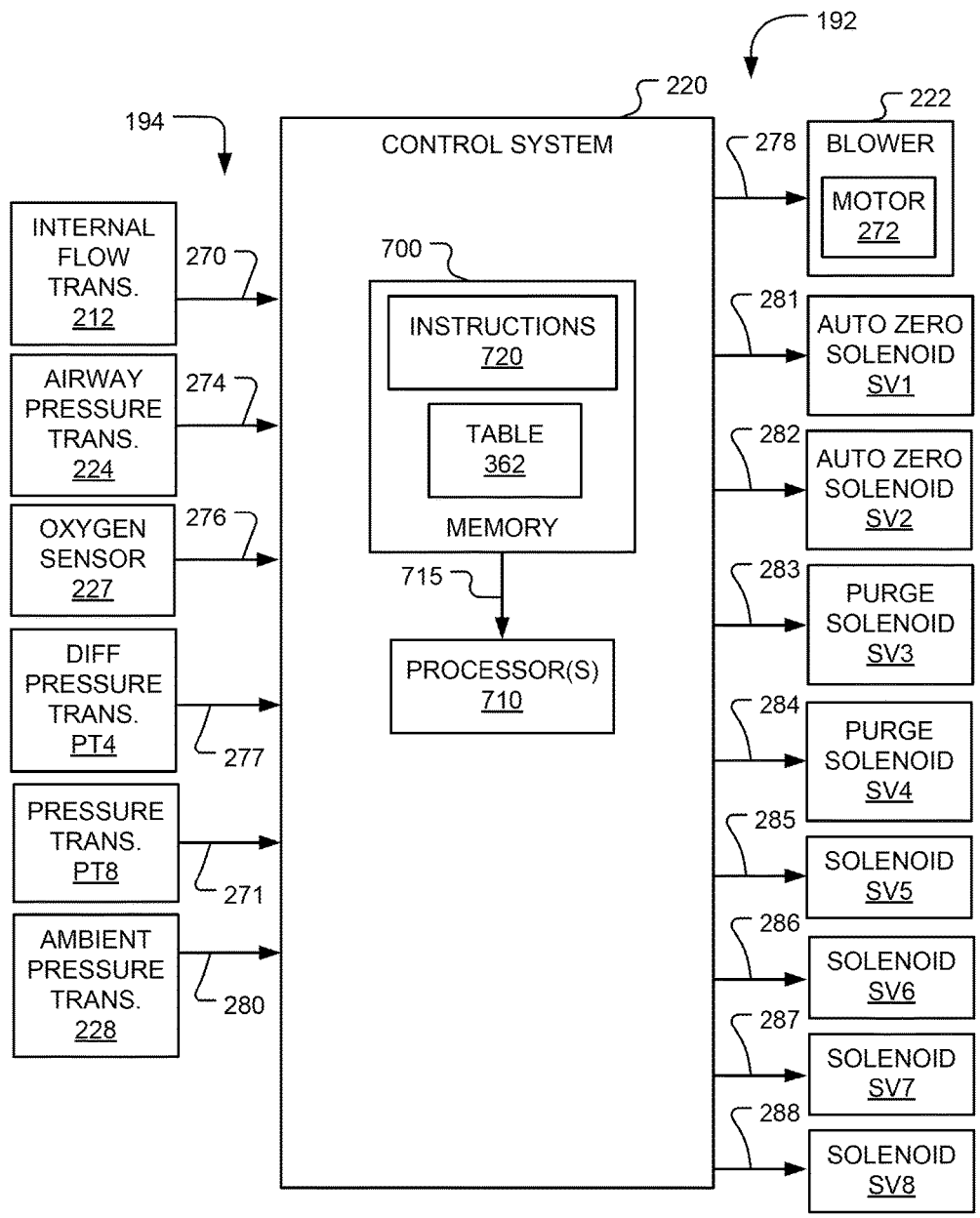
FIG. 5B is block diagram illustrating exemplary components of a control system of the ventilator, control signals sent by the control system to exemplary components of the ventilation assembly, and the data signals received by the control system from exemplary components of the ventilation assembly.

FIG. 5A is a schematic diagram illustrating some exemplary components of the ventilation assembly 190. FIG. 5B is a block diagram illustrating exemplary components of the control system 220, the control signal(s) 192 sent by the control system 220 to exemplary components of the ventilation assembly 190, and the data signals 194 received by the control system 220 from exemplary components of the ventilation assembly 190.

Referring to FIG. 5A, the ventilation assembly 190 includes an accumulator 202, an internal flow transducer 212, a blower 222, an airway pressure transducer 224, an airway flow transducer module 225, an exhalation control assembly 226, an oxygen sensor 227, an ambient pressure transducer 228, an inlet silencer 229, and an internal bacteria filter 230. At the beginning of the inspiratory phase, the air 114 may be drawn into the ventilator 100 (see FIGS. 1 and 4) through the patient air intake 116, which may be configured to filter dust and/or other types of particles from the air. At least a portion of the air 114 flows into the accumulator 202 where the air 114 may optionally be mixed with oxygen 250 received from the oxygen assembly 210, the low pressure oxygen 128 (received from the low-pressure external oxygen source 118 depicted in FIG. 1), combinations and/or sub-combinations thereof, and the like. As illustrated in FIG. 4, the high pressure oxygen 132 (received from the high-pressure external oxygen source 120 depicted in FIG. 1) flows into the oxygen assembly 210 and may be delivered to the accumulator 202 (see FIG. 5A) as the oxygen 250.

Referring to FIG. 5A, the accumulator 202 may also serve as a muffler for the patient air intake 116.

Figure 7A:
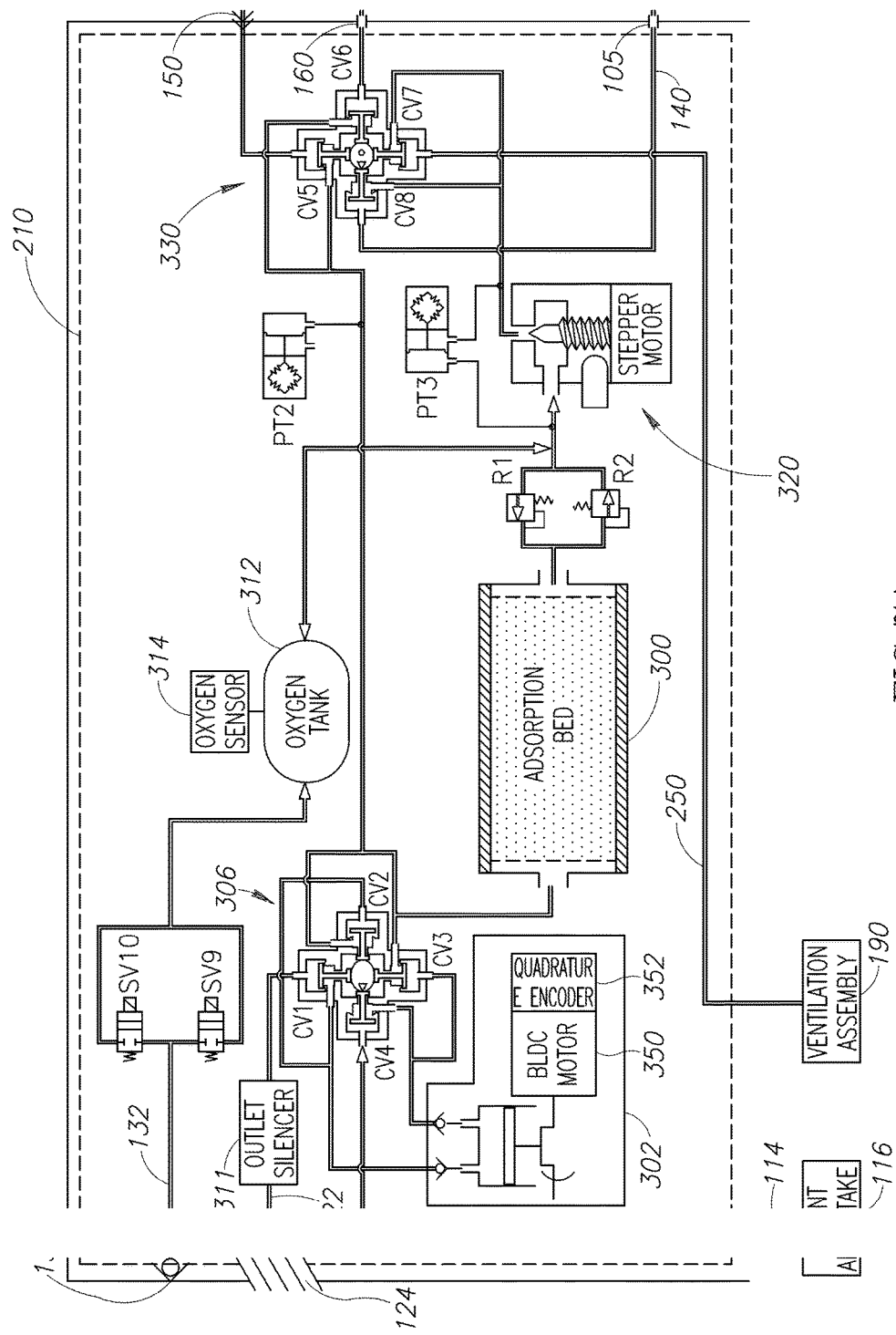
FIG. 7A is a schematic diagram illustrating some exemplary components of an oxygen assembly of the ventilator of FIG. 1.

The inlet silencer 229 helps muffle sounds created by the oxygen assembly 210 (e.g., by a compressor 302 illustrated in FIG. 7A).

The oxygen sensor 227 is connected to the accumulator 202 and measures an oxygen concentration value of the gas(es) inside the accumulator 202. This value approximates the oxygen concentration value of a gas 252 that exits the accumulator 202. Referring to FIG. 5B, the oxygen sensor 227 provides an oxygen concentration signal 276 encoding the oxygen concentration value to the control system 220. The control system 220 processes the oxygen concentration signal 276 to obtain a measure of how much oxygen is in the gas 252 (e.g., expressed as a percentage). Referring to FIG. 4, the output information 198 sent by the control system 220 to the user interface 200 may include the measure of how much oxygen is in the gas 252. The user interface 200 may display this measure to the user (e.g., the patient 102 depicted in FIG. 1).

Referring to FIG. 5A, optionally, the accumulator 202 includes or is connected to the low-pressure oxygen inlet 126. When the low-pressure oxygen 128 is supplied by the low-pressure external oxygen source 118 (see FIG. 1), the control system 220 may not control the resulting oxygen concentration flowing to the patient 102. In other words, the low-pressure oxygen 128 may simply flow into the accumulator 202, be mixed with the air 114, and pushed into the patient circuit 110 (see FIG. 1) by the blower 222. When this occurs, the ventilator 100 does not control the oxygen concentration delivered to the patient 102 in the inspiratory gases 108 (see FIG. 1), but does control the delivery of the inspiratory gases 108 during the inspiratory phase of each breath.

The gas 252 exiting the accumulator 202 includes the air 114 and optionally one or more of the oxygen 250 and the oxygen 128. The gas 252 may be conducted via a conduit or flow line 214 to the internal flow transducer 212. For ease of illustration, a portion of the flow line 214 between the accumulator 202 and the internal flow transducer 212 has been omitted from FIG. 5A. The gas 252 flows through the internal flow transducer 212, which measures a flow rate of the gas 252 and provides a flow signal 270 (see FIG. 5B) encoding the flow rate to the control system 220 (see FIG. 5B). The flow signal 270 may be implemented as an analog electric signal. Referring to FIG. 5B, the control system 220 uses the flow signal 270 to control the blower 222. By way of a non-limiting example and as shown in FIG. 5A, the internal flow transducer 212 may be implemented using a flow transducer having a fixed orifice differential pressure configuration.

The internal flow transducer 212 may be used to detect when the patient 102 (see FIG. 1) has initiated a breath. In particular, the internal flow transducer 212 may be used in this manner when the patient circuit 110 (see FIG. 1) is implemented as a passive patient circuit (e.g., the passive patient circuit 170, the passive patient circuit 440, and the like). The flow of gases through the flow line 214 is not determined entirely by the blower 222. Instead, the patient's breathing efforts may cause a change in the flow rate through the flow line 214. Thus, the control system 220 may identify that the patient 102 has initiated a breath by identifying a change in the flow rate (encoded in the flow signal 270) through the flow line 214.

The internal flow transducer 212 may include or be connected to an auto zero solenoid valve SV5 configured to be selectively activated and deactivated by a control signal 285 (see FIG. 5B) sent by the control system 220. The internal flow transducer 212 may drift over time, causing flow rate measuring errors. To compensate for this error, occasionally (e.g., periodically) the control system 220 energizes (or activates) the auto zero solenoid valve SV5 (using the control signal 285) and determines an offset value for the internal flow transducer 212. After determining the offset value, the control system 220 uses the offset value to compensate future readings (based on the flow signal 270) accordingly.

Referring to FIG. 5A, after the internal flow transducer 212, the gas 252 flows into the blower 222. The gas 252 may be conducted into the blower 222 via the flow line 214. For ease of illustration a portion of the flow line 214 between the internal flow transducer 212 and the blower 222 has been omitted from FIG. 5A. Referring to FIG. 5B, the blower 222 may be implemented as a radial blower driven by a motor 272. By way of a non-limiting example, the motor 272 may be implemented as a brushless direct current motor. By way of additional non-limiting examples, the blower 222 may be implemented as a compressor, a pump, and the like. The motor 272 has an operating speed that is controlled by the control system 220. By way of a non-limiting example, the control system 220 may continuously control the operating speed of the motor 272.

Referring to FIG. 5A, the gas 252 flows out of the blower 222 and into a conduit or flow line 273. The flow line 273 may include one or more ports (e.g., a blower port 275A and a port 275B) configured to provide access to the flow of the gas 252 in the flow line 273. The flow line 273 conducts the flow of the gas 252 from the blower 222 to the internal bacteria filter 230. For ease of illustration a portion of the flow line 273 between the ports 275A and 275B has been omitted from FIG. 5A.

Referring to FIG. 5A, the airway pressure transducer 224 measures airway pressure of the gas 252 flowing out of the blower 222 and toward the main ventilator connection 104. Referring to FIG. 5B, the airway pressure transducer 224 provides an electrical pressure signal 274 encoding these pressure values to the control system 220. The electrical pressure signal 274 is used to control patient pressure during the inspiratory and exhalation phases. The electrical pressure signal 274 is also used by the monitoring and alarm systems 221 (see FIG. 4). Optionally, the ventilator 100 (see FIGS. 1 and 4) may include one or more redundant airway pressure transducers (not shown) like the airway pressure transducer 224 to provide a failsafe backup for the airway pressure transducer 224.

The airway pressure transducer 224 may be used by the control system 220 to detect a pressure change and in response to detecting a pressure change, instruct the blower 222 to increase or decrease its speed to adjust the pressure inside the flow line 273. Thus, the control system 220 may use the electrical pressure signal 274 to deliver pressure ventilation and/or help ensure the pressure inside the flow line 273 does not exceed an user supplied peak inspiratory pressure value (e.g., entered via the pressure control input 237 depicted in FIG. 6).

Referring to FIG. 5A, the airway flow transducer module 225 includes a differential pressure transducer PT4, auto zero solenoid valves SV1 and SV2, and purge solenoid valves SV3 and SV4. Referring to FIG. 5B, the control system 220 may selectively activate or deactivate the solenoid valves SV1-SV4 using control signals 281-284, respectively.

Referring to FIG. 1, as mentioned above, the patient circuit 110 may include the one or more optional ports 111. FIG. 5A illustrates an implementation of the ventilation assembly 190 configured for use with the patient circuit 110 implemented as an active patient circuit (e.g., the active patient circuit 600 depicted in FIG. 3A, and the like). In alternate embodiments configured for use with the patient circuit 110 implemented as a passive patient circuit (e.g., the passive patient circuit 170 depicted in FIG. 2A, the passive patient circuit 440 depicted in FIG. 2B, and the like), the ports 275A and 275B, the airway flow transducer module 225, and the exhalation control assembly 226 may be omitted from the ventilation assembly 190.

The airway flow transducer module 225, and the exhalation control assembly 226 illustrated in FIG. 5A are configured for use with an active patient circuit (e.g., the active patient circuit 600 depicted in FIG. 3A) that includes the airway flow transducer 648 (see FIG. 3G). Referring to FIG. 5A, the first and second ports 111A and 111B (see FIG. 3C) send first and second pressure signals 109A and 109B, respectively, (e.g., via separate lines or channels) to the differential pressure transducer PT4. The differential pressure transducer PT4 has input ports PA and PB configured to receive the first and second pressure signals 109A and 109B, respectively. The differential pressure transducer PT4 determines a differential pressure based on the first and second pressure signals 109A and 109B, converts the differential pressure to a signal 277 (see FIG. 5B), and (as illustrated in FIG. 5B) transmits the signal 277 to the control system 220 for further processing thereby. By way of a non-limiting example, the signal 277 may be an analog signal.

The signal 277 may be used to detect when the patient 102 (see FIG. 1) has initiated a breath. The flow of gases through the active patient circuit 600 (see FIG. 3A) is not determined entirely by the blower 222. Instead, the patient's breathing efforts may cause a change in the flow rate through the active patient circuit 600. Thus, the control system 220 may identify that the patient 102 has initiated a breath by identifying a change in the flow rate (encoded in the signal 277) through the active patient circuit 600.

The auto zero solenoid valves SV1 and SV2 are connected to the input ports PA and PB, respectively, of the differential pressure transducer PT4. Further, each of the auto zero solenoid valves SV1 and SV2 is connected to ambient pressure. The differential pressure transducer PT4 can drift over time causing flow measuring errors. To compensate for this error, occasionally (e.g., periodically)

the control system 220 energizes (or activates) the auto zero solenoid valves SV1 and SV2 (using the control signals 281 and 282, respectively) and determines an offset value for the differential pressure transducer PT4. Then, the control system 220 deactivates the auto zero solenoid valves SV1 and SV2 (using the control signals 281 and 282, respectively). After determining the offset value, the control system 220 uses the offset value to compensate future readings (based on the signal 277) accordingly.

The purge solenoid valves SV3 and SV4 are connected to the blower port 275A. Referring to FIG. 5B, the control system 220 occasionally (e.g., periodically) energizes (or activates) the purge solenoid valves SV3 and SV4 (using the control signals 283 and 284, respectively), which allows dry gas from the line 273 (see FIG. 5A) to flow through the lines, ports, and/or channels (e.g., the optional multi-lumen tube connection 103, the channels 626A and 626B, the channels 632A and 632B, the ports 111A and 111B, and the like) conducting the pressure signals 109A and 109B to purge those structures of any moisture that may have condensed from the humid patient breathing gas.

The exhalation control assembly 226 includes an accumulator A2, a pressure transducer PT8, and solenoid valves SV6-SV8. The accumulator A2 has three ports 267-269 and an internal pressure (referred as the "pilot pressure"). The pressure transducer PT8 is connected to the accumulator A2, measures the internal pressure inside the accumulator A2, and transmits this value to the control system 220 in an electrical pressure signal 271 (see FIG. 5B).

Referring to FIG. 5B, the solenoid valves SV6-SV8 are configured to be selectively activated and deactivated by control signals 286-288, respectively, sent by the control system 220 to the solenoid valves SV6-SV8, respectively. Turning to FIG. 5A, the solenoid valve SV6 is connected to the first port 267 of the accumulator A2, the port 275B, and the pilot port 111C (see FIG. 3C) of the active patient circuit 600 (see FIG. 3A). The solenoid valve SV7 is connected to the second port 268 of the accumulator A2 and the port 275B. The solenoid valve SV8 is connected between the third port 269 of the accumulator A2 and the outlet port 166.

The exhalation control assembly 226 provides the pilot pressure (from the accumulator A2) to the pilot port 111C (see FIG. 3C) of the active patient circuit 600 (see FIG. 3A), which as described above, controls the active exhalation valve assembly 604. At the start of the inspiratory phase, the control system 220 activates the solenoid valve SV6 (using the control signal 286), which connects the pressure of the gases 252 (via the port 275B) to the pilot port 111C. This closes the active exhalation valve assembly 604. At the end of the inspiratory phase, the control system 220 deactivates the solenoid valve SV6 (using the control signal 286), which connects the internal pressure of the accumulator A2 (or the pilot pressure) to the active exhalation valve assembly 604, which opens the active exhalation valve assembly 604.

The control system 220 uses the solenoid valves SV7 and SV8 to control the pilot pressure inside the accumulator A2 using feedback provided by the pressure transducer PT8 (via the electrical pressure signal 271 depicted in FIG. 5B) to set a pilot pressure for the exhalation phase that will achieve the desired PEEP. For example, the control system 220 may lower the pilot pressure inside the accumulator A2 by activating the solenoid valve SV8 (using the control signal 288) to vent some of the gases inside the accumulator A2 via the outlet port 166 as the exhaust 167. Conversely, the control system 220 may increase the pilot pressure by activating the solenoid valve SV7 (using the control signal 287) to add some of the gases 252 (obtained via the port 275B) to the inside of the accumulator A2.

Referring to FIG. 5B, the control system 220 uses the electrical pressure signal 274 (received from the airway pressure transducer 224) to help control the blower 222. The control system 220 sends a control signal 278 to the motor 272, which directs the blower 222 to provide a desired flow rate and/or a desired amount of pressure to the patient 102. As mentioned above, the flow signal 270 is used to help control the flow rate of the gas 252 during the inspiratory and exhalation phases. Similarly, the electrical pressure signal 274 is used to control the patient pressure during the inspiratory and exhalation phases.

As explained above, the ventilator 100 adjusts the pressure inside the patient circuit 110 (e.g., the passive patient circuit 440 illustrated in FIG. 2B) to achieve the preset inspiratory pressure during the inspiratory phase, the baseline pressure or PEEP during the exhalation phase, and PEEP during the pause between the inspiratory and exhalation phases. These adjustments are made by the control system 220, which monitors the electrical pressure signal 274, and uses the control signal 278 to increase or decrease the speed of the motor 272 to achieve the desired pressure inside the patient circuit 110.

The ambient pressure transducer 228 measures an atmospheric pressure value. The ambient pressure transducer 228 provides an ambient electrical pressure signal 280 encoding the atmospheric pressure value to the control system 220. The control system 220 uses the ambient electrical pressure signal 280 to correct the flow rate values (received via the flow signal 270), and/or the exhaled tidal volume value (calculated by the control system 220) to desired standard conditions.

Referring to FIG. 5A, as mentioned above, the flow line 273 conducts the flow of the gas 252 from the blower 222 to the internal bacteria filter 230. After the gas 252 passes through the internal bacteria filter 230, they exit the internal bacteria filter 230 as the gases 112 and enter the patient circuit 110 (see FIG. 1) via the main ventilator connection 104. The internal bacteria filter 230 helps prevent bacteria in the patient circuit 110 from contaminating the ventilator 100.

User Interface

Figure 6:
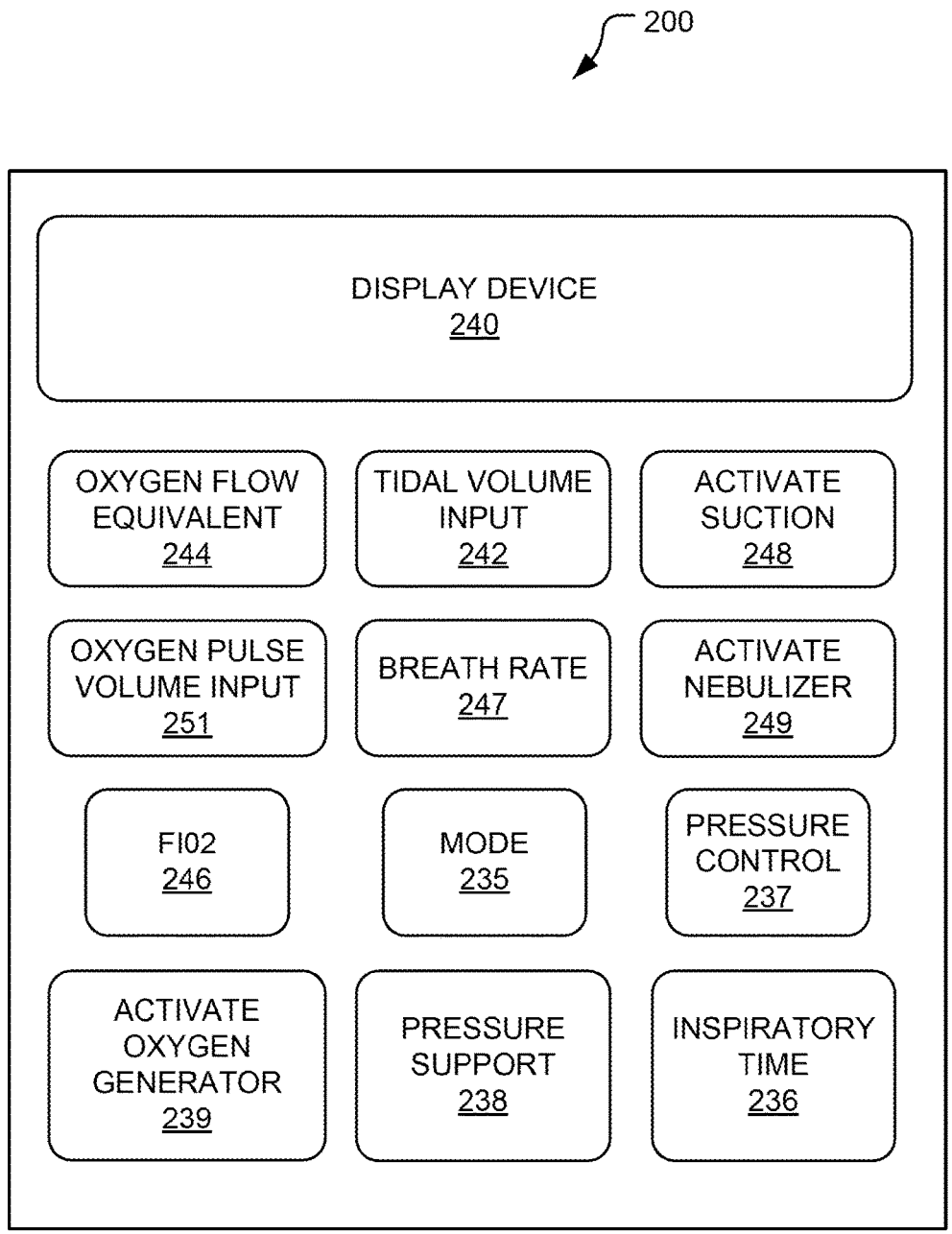
FIG. 6 is block diagram illustrating some exemplary components of a user interface of the ventilator of FIG. 1.

FIG. 6 is a block diagram illustrating some exemplary components of the user interface 200. As mentioned above, FIG. 4 illustrates the output information 198 sent by the control system 220 to exemplary components of the user interface 200, and the input information 196 received by the control system 220 from exemplary components of the user interface 200.

Referring to FIG. 6, the user interface 200 is configured to receive operating parameter values from a user (e.g., a clinician) and to display information to the user. For example, the user interface 200 may include a display device 240 (e.g., a liquid crystal display), a mode input 235, an inspiratory time input 236, a pressure control input 237, a pressure support input 238, an activate oxygen generator input 239 for activating oxygen generation (described below), a tidal volume input 242, an oxygen flow equivalent 244, a fraction of inspired oxygen ("FIO2") input 246, a breath rate input 247, an oxygen pulse volume input 251, an activate suction input 248 for activing the suction assembly 152 (see FIG. 1), and an activate nebulizer input 249 for activing the nebulizer assembly 162 (see FIG. 1).

The beginning of the inspiratory phase is referred to as "initiation." The mode input 235 is configured to receive an indication as to whether the ventilator 100 determines when each breath is initiated or the patient 102 determines when each breath is initiated. The breath rate input 247 is configured to receive a rate (e.g., breaths per minute) at which breaths are to be delivered. If the user has indicated (using the mode input 235) that the ventilator 100 determines when each breath is initiated, the ventilator 100 will deliver breaths in accordance with the rate received by the breath rate input 247 (e.g., at regularly timed intervals). On the other hand, If the user has indicated (using the mode input 235) that the patient 102 initiates each breath, the ventilator 100 will automatically deliver breaths as needed to ensure the patient 102 receives breaths at least as frequently as indicated by the rate received by the breath rate input 247.

The ventilator 100 may identify the end of the inspiratory phase using time or a rate of flow of the gases 112 to the patient 102. In the latter case, the patient 102 determines when the inspiratory phase ends. The inspiratory time input 236 is configured to receive a value indicating a duration $T_i$ from the initiation of each breath to the end of the inspiratory phase. The ventilator 100 may use the value (indicating the duration $T_i$) to identify the end of the inspiratory phase. The pressure support input 238 receives an indication that the user would like to use the rate of flow of the gases 112 to the patient 102 (instead of the value indicating the duration $T_i$) to end the inspiratory phase. For example, the ventilator 100 may end the inspiratory phase of a breath when the flow rate of the gases 112 is only about 25% of a peak flow rate that occurred during the breath.

The ventilator 100 is configured to deliver the gases 112 alone, or a combination of the gases 112 and the pulses of oxygen 140. As mentioned above, the ventilator 100 may be configured to provide both traditional volume controlled ventilation and pressure controlled ventilation. To use pressure control, the user may use the pressure control input 237 to enter a peak inspiratory pressure value. The ventilator 100 uses the peak inspiratory pressure value to configure the gases 112 alone, or the combination of the gases 112 and the pulses of oxygen 140 such that the pressure during the inspiratory phases is at most the peak inspiratory pressure value.

The FIO2 input 246 is configured to receive an oxygen concentration value. The ventilator 100 uses the oxygen concentration value to configure the gases 112 to have an oxygen concentration equal to or approximating the oxygen concentration value.

The oxygen pulse volume input 251 is configured to receive an oxygen pulse volume value (e.g., expressed in milliliters, or a value within a predefined range, such as from 1 to 10, and the like). The ventilator 100 uses the oxygen pulse volume value to configure each of the pulses of oxygen 140 to have a volume equal to or approximating the oxygen pulse volume value.

Figure 15A:
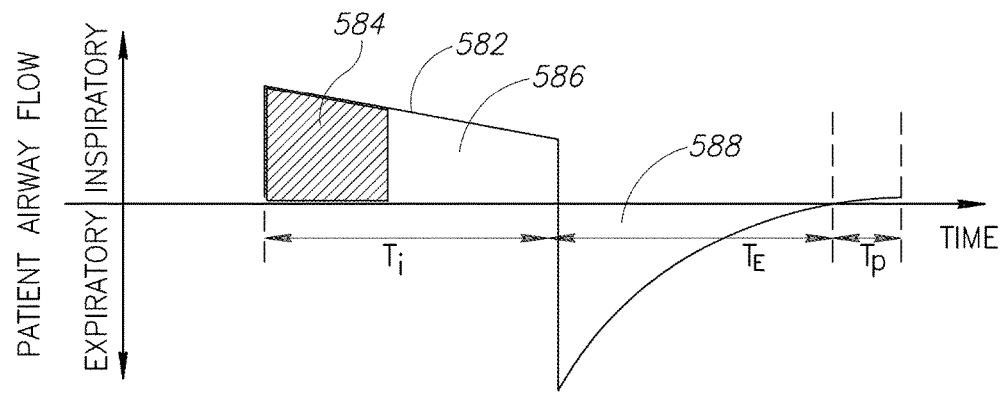
FIG. 15A is a graph showing patient airway flow using the ventilator of FIG. 1 during both inspiratory and expiratory phases.

The tidal volume input 242 is configured to receive a desired total tidal volume value. Referring to FIG. 15A, the ventilator 100 uses the desired total tidal volume value to output a volume of the gases 112 (illustrated by area 586 and described below) and one of the pulses of oxygen 140 (illustrated by area 584 and described below) during each breath. For each breath delivered, the total tidal volume delivered is the combined volumes of gases 112 and the pulse of oxygen 140 delivered during the breath.

The oxygen flow equivalent 244 is configured to receive a desired oxygen delivery rate (expressed in liters per minute) that identifies a rate at which a hypothetical continuous oxygen flow may be bled into a conventional ventilator or the patient circuit 110 (see FIG. 1) from an external source (e.g., a stand-alone oxygen concentrator). The ventilator 100 uses this value to configure each of the pulses of oxygen 140 (see FIG. 1) to deliver an amount of oxygen that would provide equivalent oxygenation to the patient 102 (see FIG. 1) as the hypothetical continuous oxygen flow.

Oxygen Assembly

Figure 7B:
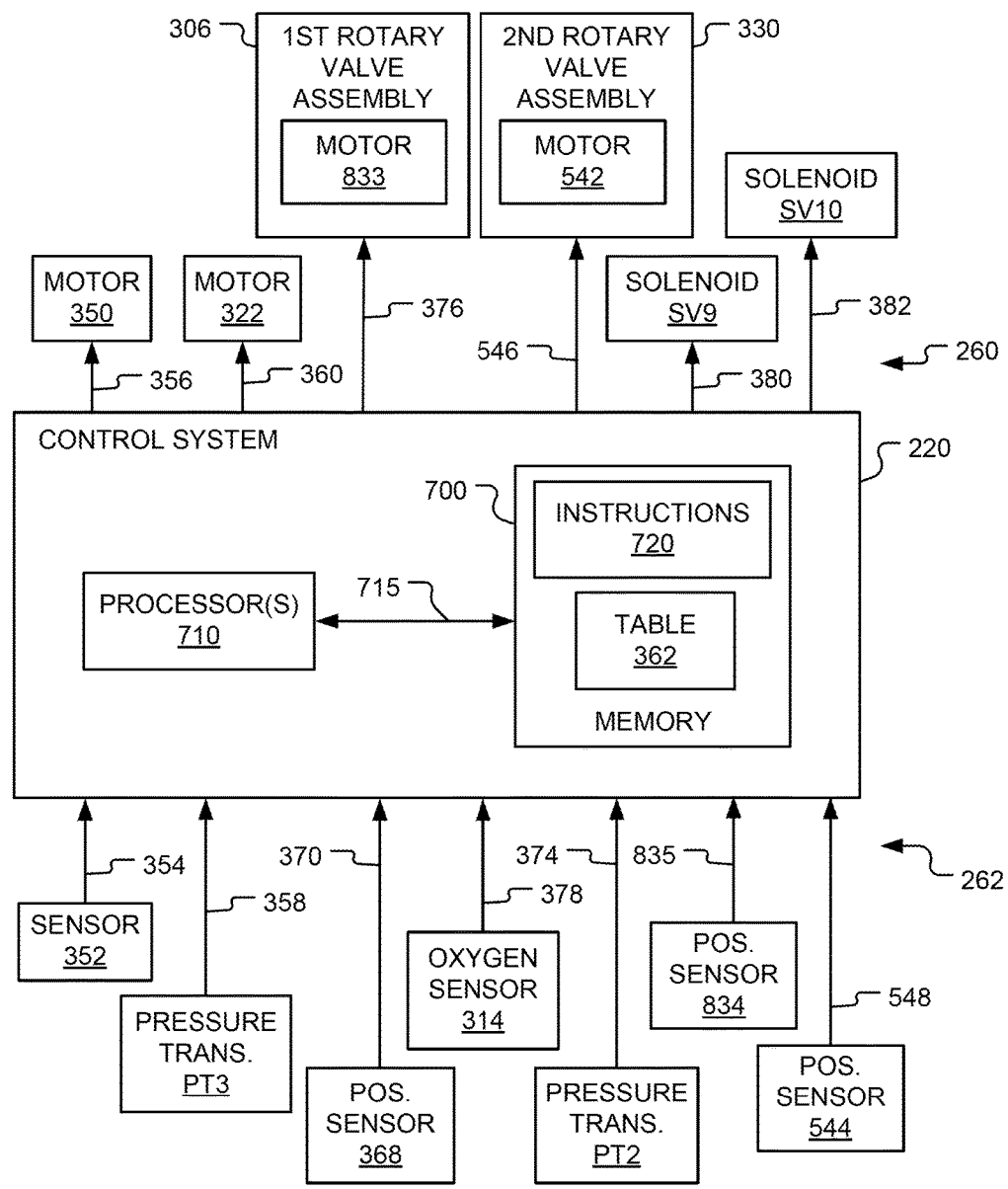
FIG. 7B is block diagram illustrating exemplary control signals sent by the control system to exemplary components of the oxygen assembly, and the data signals received by the control system from exemplary components of the oxygen assembly.

FIG. 7A is a schematic diagram illustrating some exemplary components of the oxygen assembly 210. FIG. 7B illustrates the control signals 260 sent by the control system 220 to exemplary components of the oxygen assembly 210, and the data signals 262 received by the control system 220 from exemplary components of the oxygen assembly 210.

Referring to FIG. 7A, the oxygen assembly 210 is configured to receive the high-pressure oxygen 132 and/or generate oxygen 346 (see FIG. 8B) and provide the oxygen 250 to the accumulator 202 (see FIG. 5A) of the ventilation assembly 190 and/or provide the pulses of oxygen 140 to the patient oxygen outlet 105. The oxygen assembly 210 may be configured to provide up to about two liters per minute ("LPM") of approximately 90% pure oxygen. In the embodiment illustrated, the oxygen assembly 210 includes an adsorption bed 300, the compressor 302, a first rotary valve assembly 306, two pressure transducers PT2 and PT3, two pressure regulators R1 and R2, an outlet silencer 311, optional solenoid valves SV9 and SV10, an oxygen tank 312, an oxygen sensor 314, a metering valve 320, and an optional second rotary valve assembly 330. Together the compressor 302, the first rotary valve assembly 306, the adsorption bed 300, and the pressure regulators R1 and R2 may be characterized as being an oxygen generator or oxygen concentrator. The oxygen generator illustrated in the figures and described below implements a vacuum pressure swing absorption ("VPSA") process. In alternate embodiments, the ventilator 100 may include an oxygen generator that implements at least one of a polymer membrane separation process, an ion transport separation process, a cryogenic process, and the like. Further, the VPSA process described below is a subset of Pressure Swing Adsorption (PSA) and the oxygen generator may be configured to implement a PSA process other than the VPSA process described below.

The adsorption bed 300 is configured to harvest oxygen from the air 114 received via the patient air intake 116. As will be explained below, the adsorption bed 300 may be configured to at least partially implement a VPSA process that includes a cycle with four phases (described below). The cycle alternately generates the oxygen 346 (see FIG. 8B) and the nitrogen-rich gas 122. As the ventilator 100 operates, the cycle is repeated until enough oxygen has been generated to fill the oxygen tank 312. When the oxygen tank 312 is full, the cycles are halted or slowed until a sufficient amount of the oxygen in the oxygen tank 312 has been removed. Then, the cycles are resumed again or sped up as appropriate. The nitrogen-rich gas 122 generated by each cycle is exhausted to the outside environment via the outlet vent 124.

FIGS. 8A-8D are block diagrams illustrating some exemplary components of the adsorption bed 300. Referring to FIGS. 8A-8D, in the embodiment illustrated, the adsorption bed 300 includes at least one housing 340 having a first end 341 opposite a second end 343. The housing 340 contains a bed of nitrogen adsorbent material 344 (such as zeolite)

between its first and second ends 341 and 343. The bed of nitrogen adsorbent material 344 preferentially absorbs nitrogen. For ease of illustration, the adsorption bed 300 will be described as including a single housing containing a single bed of nitrogen adsorbent material. In alternate embodiments, the adsorption bed 300 may include two or more beds like the bed of nitrogen adsorbent material 344 that are each housed inside separate housings like the housing 340.

Figure 8A:
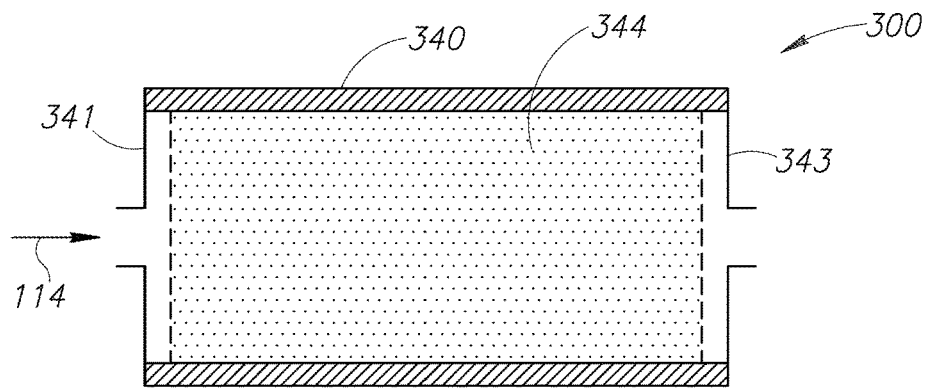
FIG. 8A is a block diagram illustrating an adsorption bed of the oxygen assembly during a first phase of a vacuum pressure swing adsorption ("VPSA") process.

As mentioned above, the VPSA process includes a cycle with four phases. FIG. 8A illustrates the adsorption bed 300 during a first phase. Referring to FIG. 8A, during the first phase, the air 114 is pumped into the housing 340 by the compressor 302 (see FIG. 7A). When the housing 340 is pressurized with the air 114 (by the compressor 302), nitrogen in the air is preferentially adsorbed by the bed of nitrogen adsorbent material 344, which leaves behind unadsorbed oxygen. The bed of nitrogen adsorbent material 344 may include interstitial spaces in which the unadsorbed oxygen is held or trapped.

Figure 8B:
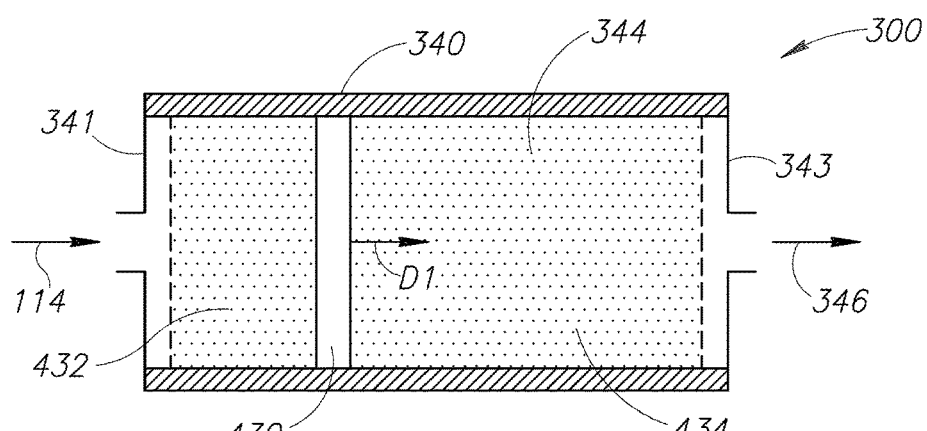
FIG. 8B is a block diagram illustrating the adsorption bed of the oxygen assembly during a second phase of the VPSA process.

FIG. 8B illustrates the adsorption bed 300 during a second phase of a cycle of the VPSA process. During the second phase, the oxygen 346 is pumped from the housing 340. The oxygen 346 flows from the interstitial spaces and into the oxygen tank 312 (see FIG. 7A).

Figure 8C:
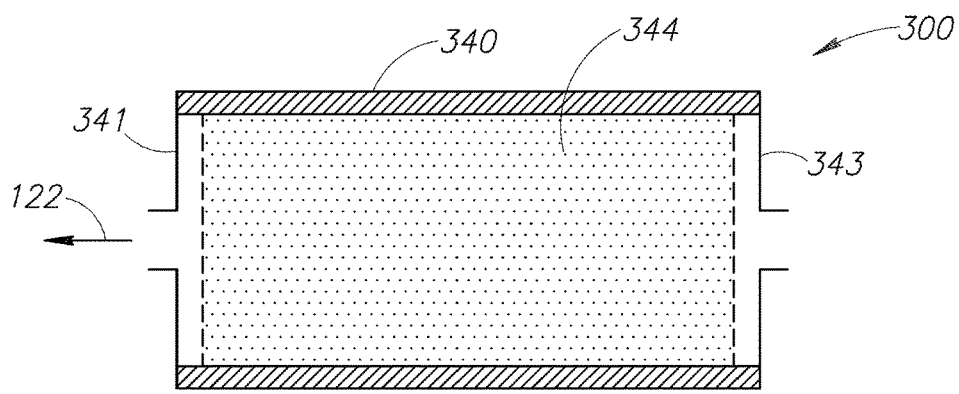
FIG. 8C is a block diagram illustrating the adsorption bed of the oxygen assembly during a third phase of the VPSA process.

FIG. 8C illustrates the adsorption bed 300 during a third phase of a cycle of the VPSA process. During the third phase, the nitrogen-rich gas 122 is pulled from the bed of nitrogen adsorbent material 344 in the housing 340 (by the compressor 302 illustrated in FIG. 7A) and vented to the outside environment via the outlet vent 124 (see FIG. 7A).

Figure 8D:
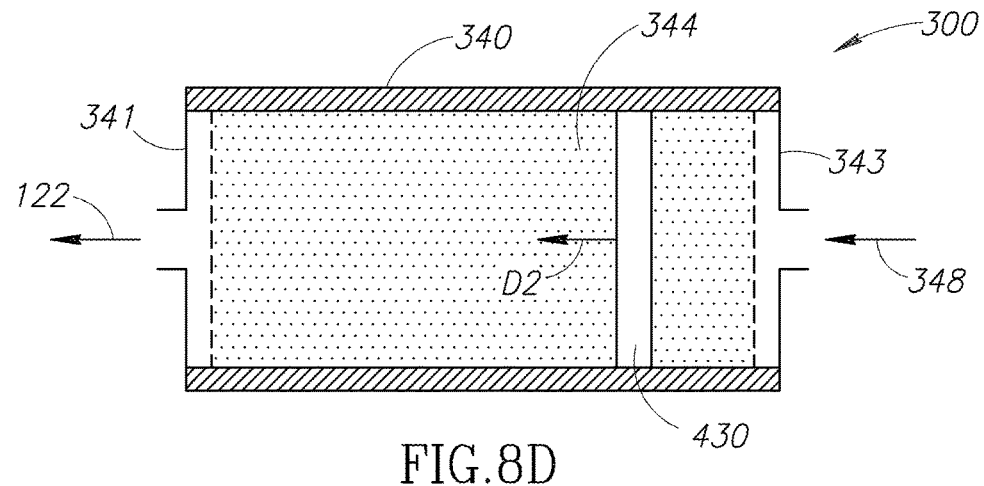
FIG. 8D is a block diagram illustrating the adsorption bed of the oxygen assembly during a fourth phase of the VPSA process.

FIG. 8D illustrates the adsorption bed 300 during a fourth phase of a cycle of the VPSA process. During the fourth phase, a flow of "purge" oxygen 348 (e.g., from the oxygen tank 312 illustrated in FIG. 7A) may be used to help draw out the nitrogen-rich gas 122 and regenerate the bed of nitrogen adsorbent material 344.

Returning to FIG. 7A, the oxygen 346 (see FIG. 8B) removed from the adsorption bed 300 flows through the pressure regulator R2, and into the oxygen tank 312 where the oxygen 346 is stored. While this is occurring, the metering valve 320 may be closed, and the pressure regulator R1 may be closed to prevent flow back into the adsorption bed 300. Alternatively, the metering valve 320 may be at least partially open to allow some of the oxygen 346 to flow to the optional second rotary valve assembly 330.

During each cycle, the compressor 302 is configured to alternately push the air 114 into the adsorption bed 300 (through the first rotary valve assembly 306) and pull the nitrogen-rich gas 122 out of the adsorption bed 300 (through the first rotary valve assembly 306). The compressor 302 may be driven by a motor 350 and may include a sensor 352 (e.g., an encoder) configured to provide a signal 354 encoding the direction and speed of rotation of the motor 350 to the control system 220. Referring to FIG. 7B, the motor 350 is configured to receive instructions from the control system 220 encoded in a control signal 356. The instructions in the control signal 356 instruct the motor 350 to switch on or off and/or indicate in which direction the motor 350 is to rotate when switched on. Further, the control signal 356 may instruct the motor 350 at which speed to run. Referring to FIG. 7A, when the motor 350 runs in a first direction, the compressor 302 pushes air into the adsorption bed 300. On the other hand, when the motor 350 runs in a second direction, the compressor 302 pulls the nitrogen-rich gas 122 (see FIGS. 8C and 8D) from the adsorption bed 300. By way of a non-limiting example, the motor 350 may be implemented as a brushless direct current motor.

Figure 9:
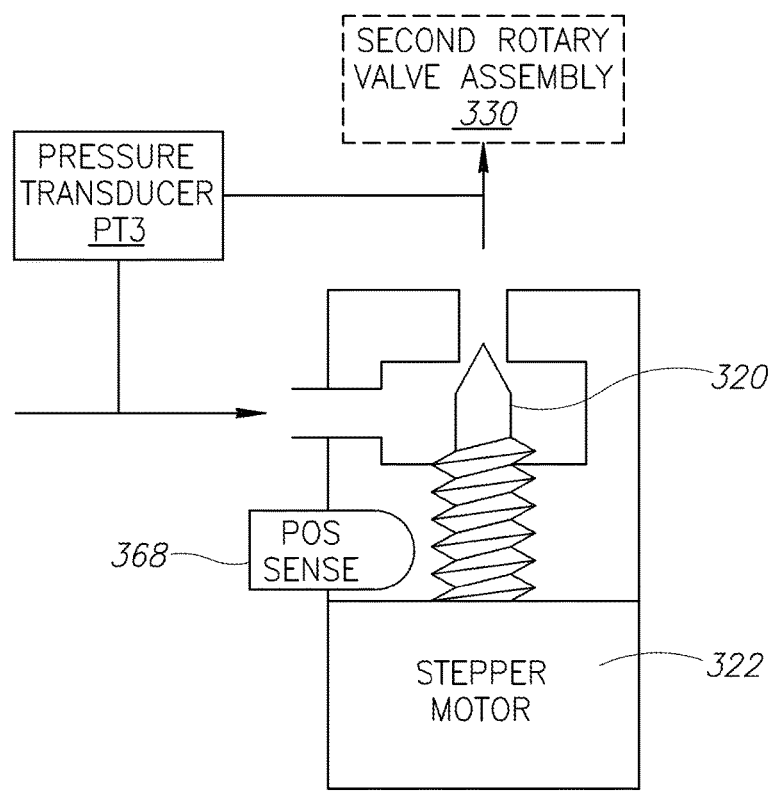
FIG. 9 is an illustration of a metering valve of the oxygen assembly.

FIG. 9 is an illustration of the metering valve 320. Referring to FIG. 9, the pressure transducer PT3 is connected across the metering valve 320. Thus, the pressure transducer PT3 may determine a pressure differential value across the metering valve 320. Referring to FIG. 7B, the pressure transducer PT3 provides a pressure differential signal 358 encoding the pressure differential value to the control system 220.

Referring to FIGS. 7B and 9, the metering valve 320 may be driven by a stepper motor 322 configured to receive a control signal 360 from the control system 220 encoding a stepper position value. The stepper motor 322 is configured to move to the stepper position value encoded in the control signal 360. In the embodiment illustrated, the metering valve 320 is a stepper driven proportioning valve characterized by three variables: (1) valve position, (2) differential pressure across the valve (as measured by the pressure transducer PT3), and (3) flow rate. When a particular flow rate is desired (e.g., entered by the user via the flow rate input 248 depicted in FIG. 6), the control system 220 uses the pressure differential signal 358 (encoding the pressure differential value) and the particular flow rate to "look up" a corresponding stepper position value in a characterization table 362. In other words, the characterization table 362 stores stepper position values each associated with a flow rate value and a pressure differential value. Thus, a particular pressure differential value and a particular flow rate value may be used by the control system 220 to determine a stepper position value. Then, the control system 220 encodes the stepper position value in the control signal 360 and sends it to the stepper motor 322. This process may be repeated occasionally (e.g., every few milliseconds) to provide an instantaneously desired oxygen flow rate.

Referring to FIG. 9, a position sensor 368 may be operatively coupled to the metering valve 320 and used to determine a home position. The position sensor 368 provides a position signal 370 to the control system 220 that encodes whether the metering valve 320 is in the home position (e.g., true or "on") or at a position other than the home position (e.g., false or "off").

Referring to FIG. 7A, the pressure regulator R2 may be characterized as being a back pressure regulator. The pressure regulator R2 may be configured to prevent the pressure inside the adsorption bed 300 from exceeding a first threshold pressure value (e.g., approximately 10 pounds per square inch ("PSIG")). For example, the pressure regulator R2 may be configured to allow oxygen to flow automatically from the adsorption bed 300 when the pressure inside the adsorption bed 300 reaches the first threshold value. The pressure regulator R2 may also be configured to prevent gases from flowing into the adsorption bed 300. This allows the pressure regulator R2 to control the pressure during the first phase (see FIG. 8A) and the second phase (see FIG. 8B).

The pressure regulator R1 may be characterized as being a vacuum regulator. The pressure regulator R1 may be configured to prevent the pressure inside the adsorption bed 300 from falling below a second threshold pressure value (e.g., approximately −7 PSIG). Thus, the pressure regulator R1 regulates the pressure in the adsorption bed 300 to the second threshold pressure during the third phase (see FIG. 8C) and the fourth phase (see FIG. 8D). For example, the pressure regulator R1 may be configured to allow oxygen to flow automatically into the adsorption bed 300 (e.g., from the oxygen tank 312) when the pressure inside the adsorption bed 300 falls below the second threshold value. The pressure regulator R1 may also be configured to prevent gases inside the adsorption bed 300 from flowing out of the adsorption bed 300 toward the metering valve 320 (see FIG. 1).

The optional solenoid valves SV9 and SV10 may be configured to maintain the pressure inside the oxygen tank 312 between a minimum threshold pressure value (e.g., approximately 4 PSIG) and a maximum threshold pressure value (e.g., approximately 10 PSIG). The solenoid valves SV9 and SV10 are connected in a parallel arrangement to a conduit or flow line (not shown) that conducts the high-pressure oxygen 132 (e.g., from the high-pressure oxygen source 120 illustrated in FIG. 1) to the oxygen tank 312. The control system 220 selectively activates and deactivates the solenoid valves SV9 and SV10 using control signals 380 and 382 (see FIG. 7B), respectively, to maintain the pressure in oxygen tank 312 between the minimum and maximum threshold pressure values. Thus, together the control system 220 and the solenoid valves SV9 and SV10 perform the functions of a digital (on/off) regulator.

The control system 220 may automatically stop the oxygen assembly 210 from performing the VPSA process when the high-pressure external oxygen source 120 is connected. For example, the control system 220 may slow or shut down the VPSA process when pressure in the oxygen tank 312 exceeds an upper threshold (e.g., 10 PSIG). In this manner, the control system 220 may slow or shut down the VPSA process when the adsorption bed 300 is operating or the high-pressure external oxygen source 120 is connected. On the other hand, when the pressure inside the oxygen tank 312 falls below a lower pressure threshold (e.g., 4 PSIG), the control system 220 may restart or accelerate the VPSA process.

The oxygen tank 312 may be implemented as a rigid chamber configured to store a predetermined amount of oxygen (e.g., about 56 cubic inches of oxygen). The outlet silencer 311 helps muffle sounds created by the compressor 302.

Referring to FIGS. 7A and 7B, the oxygen sensor 314 measures oxygen concentration in the oxygen tank 312, and encodes an oxygen concentration value in an oxygen concentration signal 378 provided to the control system 220. The control system 220 may use the oxygen concentration signal 378 to monitor the oxygen assembly 210 to ensure it is working properly. If the oxygen concentration signal 378 indicates the oxygen concentration is too low, the control system 220 may conclude that the oxygen assembly 210 is not functioning properly.

The pressure transducer PT2 monitors the pressure between the first and second rotary valve assemblies 306 and 330 (which may be characterized as being a pump pressure supplied to the second rotary valve assembly 330). Referring to FIG. 7B, the pressure transducer PT2 provides an electrical pressure signal 374 encoding that pressure value to the control system 220.

First Rotary Valve Assembly

Figure 10A:
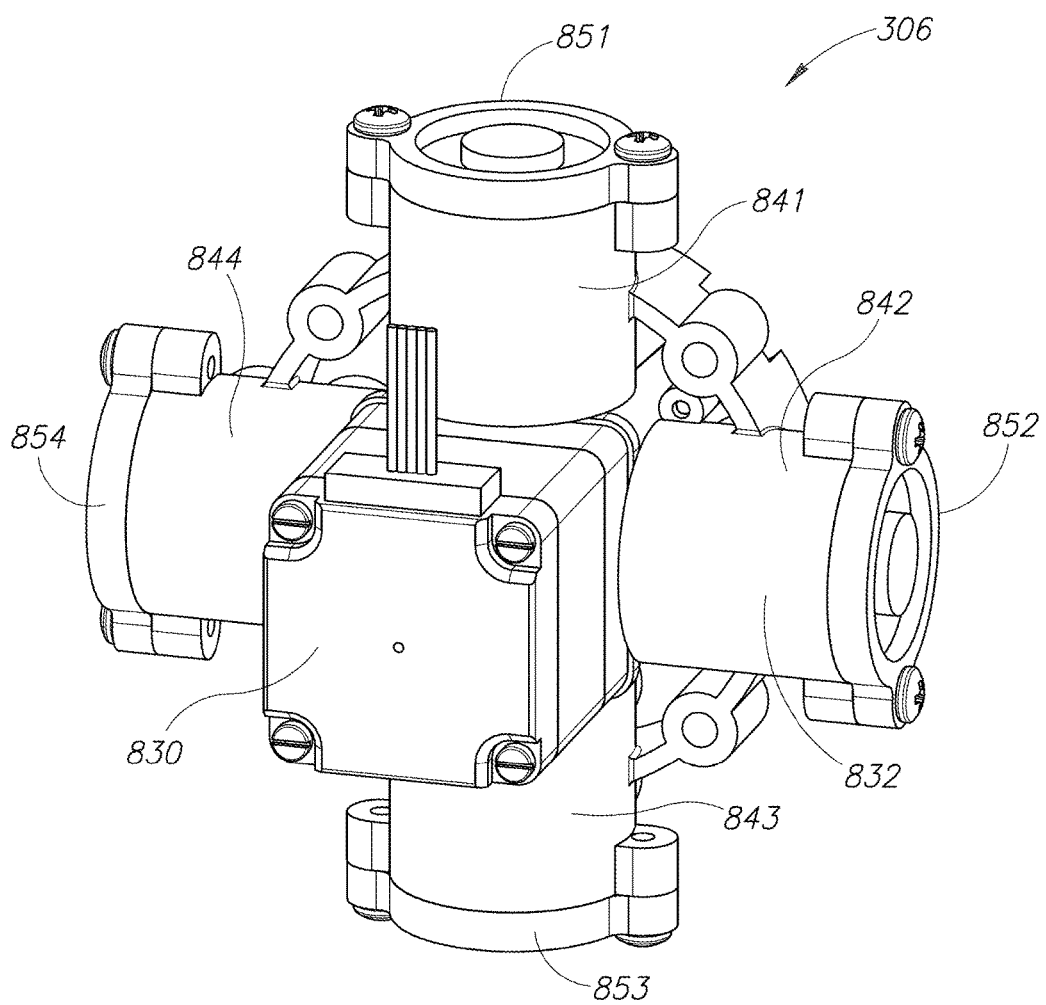
FIG. 10A is a perspective view of a first side of a first rotary valve assembly of the oxygen assembly.
Figure 10B:
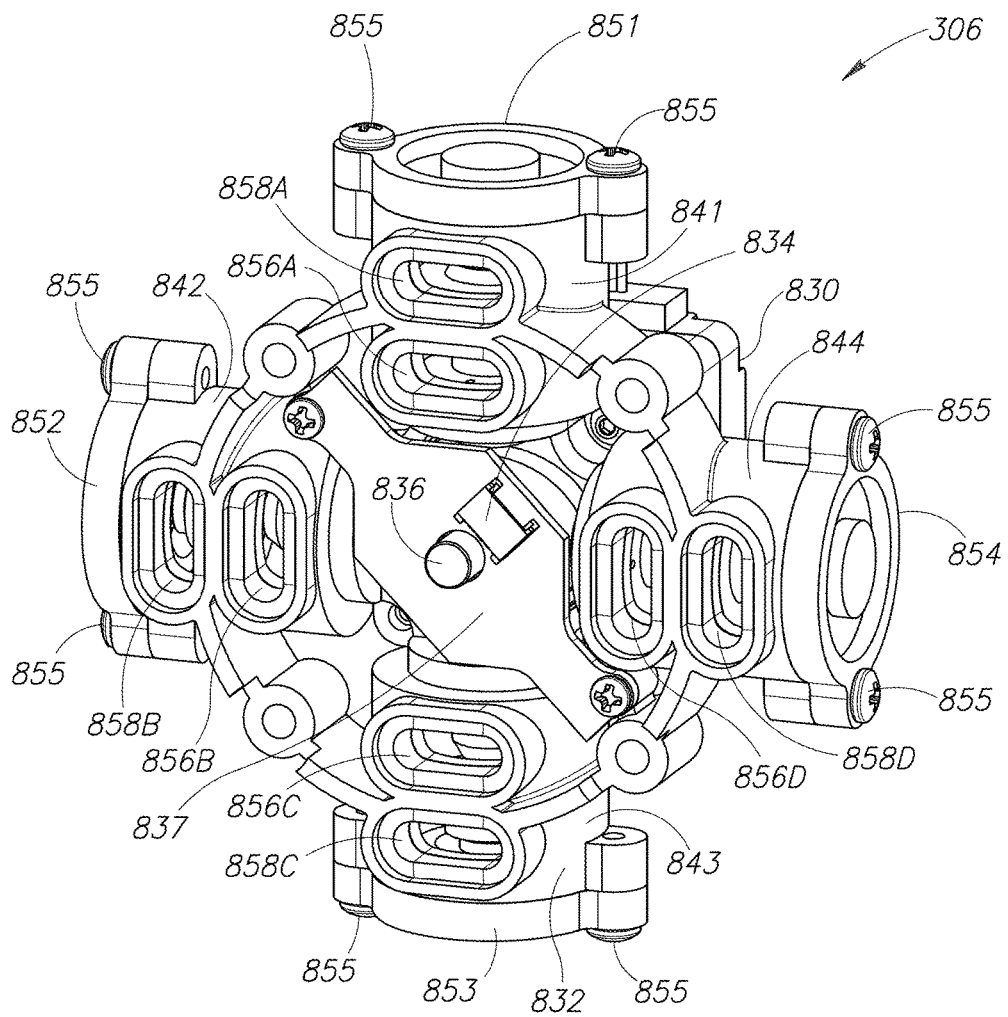
FIG. 10B is a perspective view of a second side of the first rotary valve assembly.

FIG. 10A is a perspective view of a first side of an exemplary embodiment of the first rotary valve assembly 306. FIG. 10B is a perspective view of a second side of the first rotary valve assembly 306 opposite the first side. Referring to FIG. 10A, the first rotary valve assembly 306 includes a motor assembly 830 mounted to an outer housing 832. The motor assembly 830 includes a stepper motor 833 (see FIG. 7B) and a shaft 836 (see FIGS. 10B and 10C). The stepper motor 833 is configured to rotate the shaft 836.

Referring to FIG. 10B, a position sensor 834 may be mounted on a printed circuit board ("PCB") 837 fastened to the outer housing 832 opposite the motor assembly 830. In such embodiments, the PCB 837 may include an opening through which an end of the shaft 836 opposite the motor assembly 830 may pass.

Figure 10C:
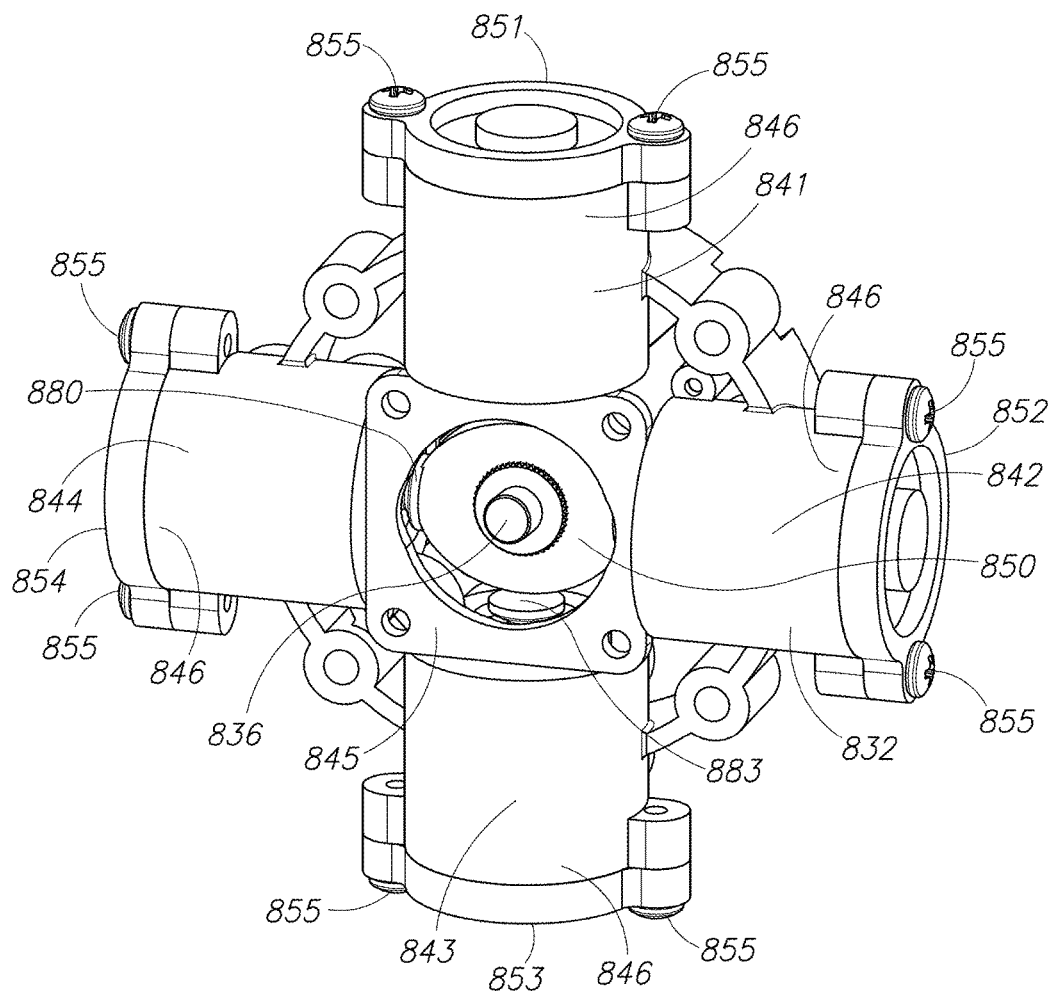
FIG. 10C is a perspective view of the first side of the first rotary valve assembly including a shaft of a motor assembly and omitting other parts of the motor assembly.

FIG. 10C depicts the first side of the first rotary valve assembly 306 and the shaft 836 of the motor assembly 830. Other parts of the motor assembly 830 have been omitted in FIG. 10C. Referring to FIG. 10C, in the embodiment illustrated, the outer housing 832 has an outer shape that is generally cross or cruciform-shaped. Thus, the outer housing 832 has four arms 841-844 that extend outwardly from a central region 845 of the outer housing 832. In the embodiment illustrated, the motor assembly 830 (see FIG. 10A) is mounted to the central region 845.

Figure 10D:
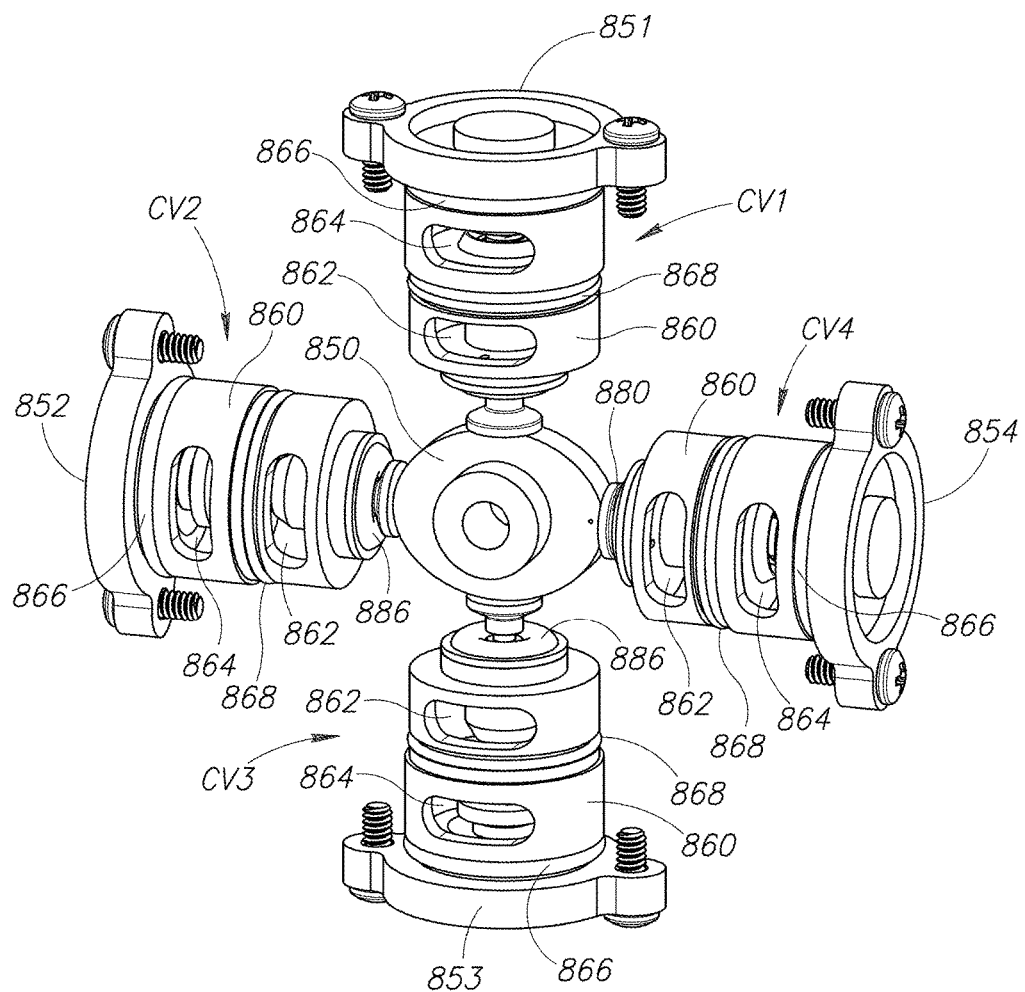
FIG. 10D is a perspective view of the second side of the first rotary valve assembly with its outer housing and printed circuit board removed.

FIG. 10D depicts the second side of the first rotary valve assembly 306 with the outer housing 832 and the PCB 837 removed. As shown in FIG. 10D, the arms 841-844 (see FIG. 10B) house poppet valves CV1-CV4, respectively. Inside the outer housing 832 (see FIG. 10B), the poppet valves CV1 and CV3 are positioned opposite one another, and the poppet valves CV2 and CV4 are positioned opposite one another. The first rotary valve assembly 306 includes a cam 850 mounted on the shaft 836 (see FIGS. 10B and 10C) and configured to selectively actuate the poppet valves CV1-CV4. The cam 850 rotates with the shaft 836 as the motor assembly 830 (see FIG. 10A) rotates the shaft 836. Referring to FIG. 7B, the position sensor 834 provides a position signal 835 to the control system 220 that encodes whether the cam 850, the stepper motor 833 (see FIGS. 10A and 10B), and/or the shaft 836 (see FIGS. 10B and 10C) is in a home position (e.g., true or "on") or at a position other than the home position (e.g., false or "off").

Referring to FIG. 10C, each of the arms 841-844 is open at its distal end 846. The open distal ends 846 of the arms 841-844 are closed by end caps 851-854, respectively. The end caps 851-854 may be fastened to the outer housing 832 by fasteners 855.

Referring to FIG. 10B, the arms 841-844 include inlet openings 856A-856D, respectively, configured to receive a gas or mixture of gases, and outlet openings 858A-858D, respectively, through which a gas or mixture of gases may exit.

Referring to FIG. 10D, each of the poppet valves CV1-CV4 includes an open ended housing 860 with a lateral inlet 862 and a lateral outlet 864. The lateral inlets 862 of the poppet valves CV1-CV4 are aligned and in fluid communication with the inlet openings 856A-856D, respectively, of the outer housing 832. Similarly, the lateral outlets 864 of the poppet valves CV1-CV4 are aligned and in fluid communication with the outlet openings 858A-858D, respectively, of the outer housing 832.

One or more seals 866 and 868 (e.g., O-ring type seals) may be positioned between the outer housing 832 and the housing 860. For example, the seal 868 may be positioned between the lateral inlet 862 and the lateral outlet 864. By way of another non-limiting example, one of the seals 866 may be positioned between each of the open distal ends 846 of the arms 841-844 and the end caps 851-854, respectively.

Figure 10E:
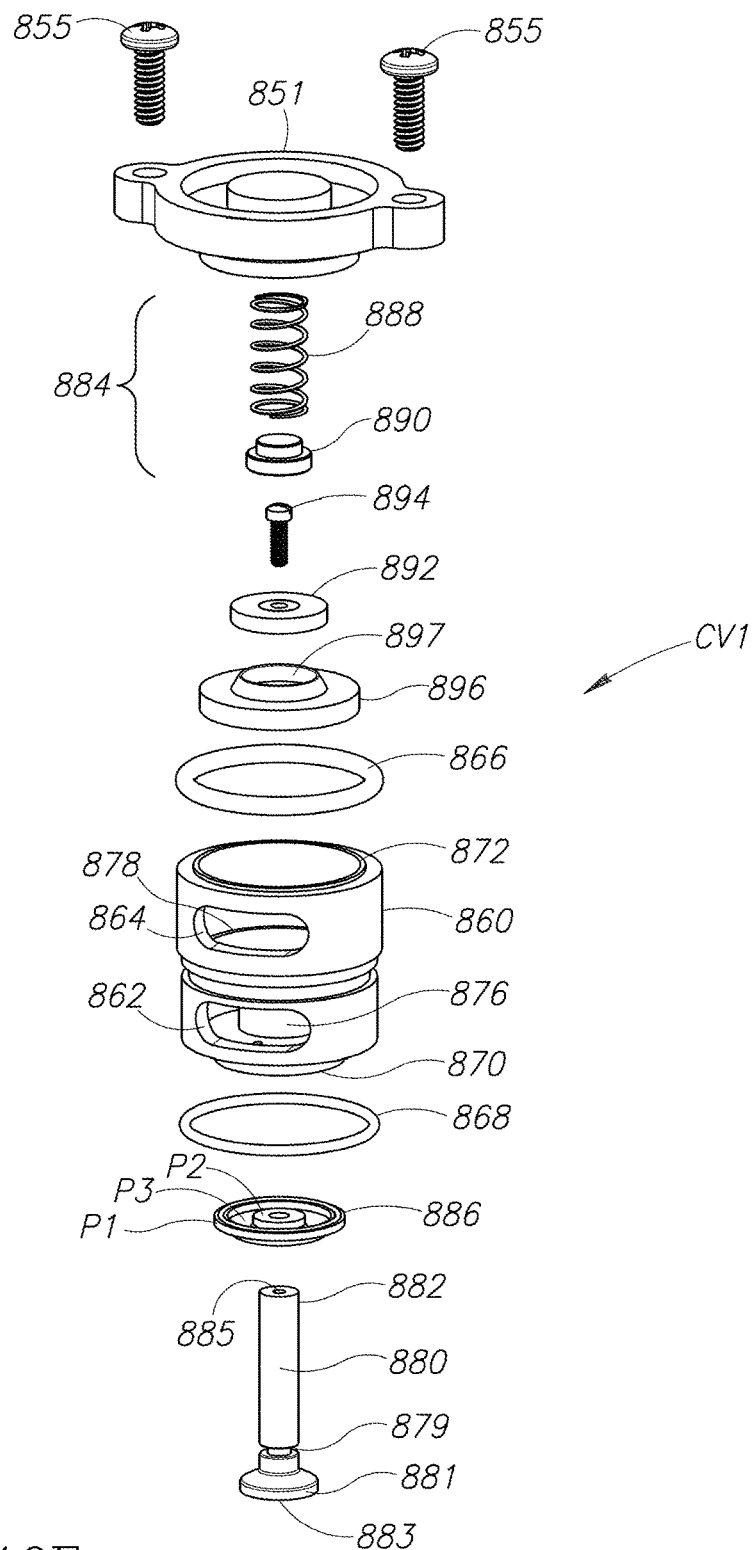
FIG. 10E is an exploded perspective view of one of four poppet valves of the first rotary valve assembly illustrated with an end cap and fasteners.

The poppet valves CV1-CV4 are substantially identical to one another. For the sake of brevity, only the poppet valve CV1 will be described in detail. FIG. 10E is an exploded perspective view of the poppet valve CV1, the end cap 851, and the fasteners 855. Referring to FIG. 10E, the housing 860 has an open proximal end portion 870 opposite an open distal end portion 872. The open distal end portion 872 is closed by the end cap 851 when the end cap 851 is fastened to the outer housing 832. Similarly, the housings 860 of the poppet valves CV2-CV4 are closed at their open distal end portions 872 by the end caps 852-853, respectively, when the end caps 852-854 are fastened to the outer housing 832

Figure 10F:
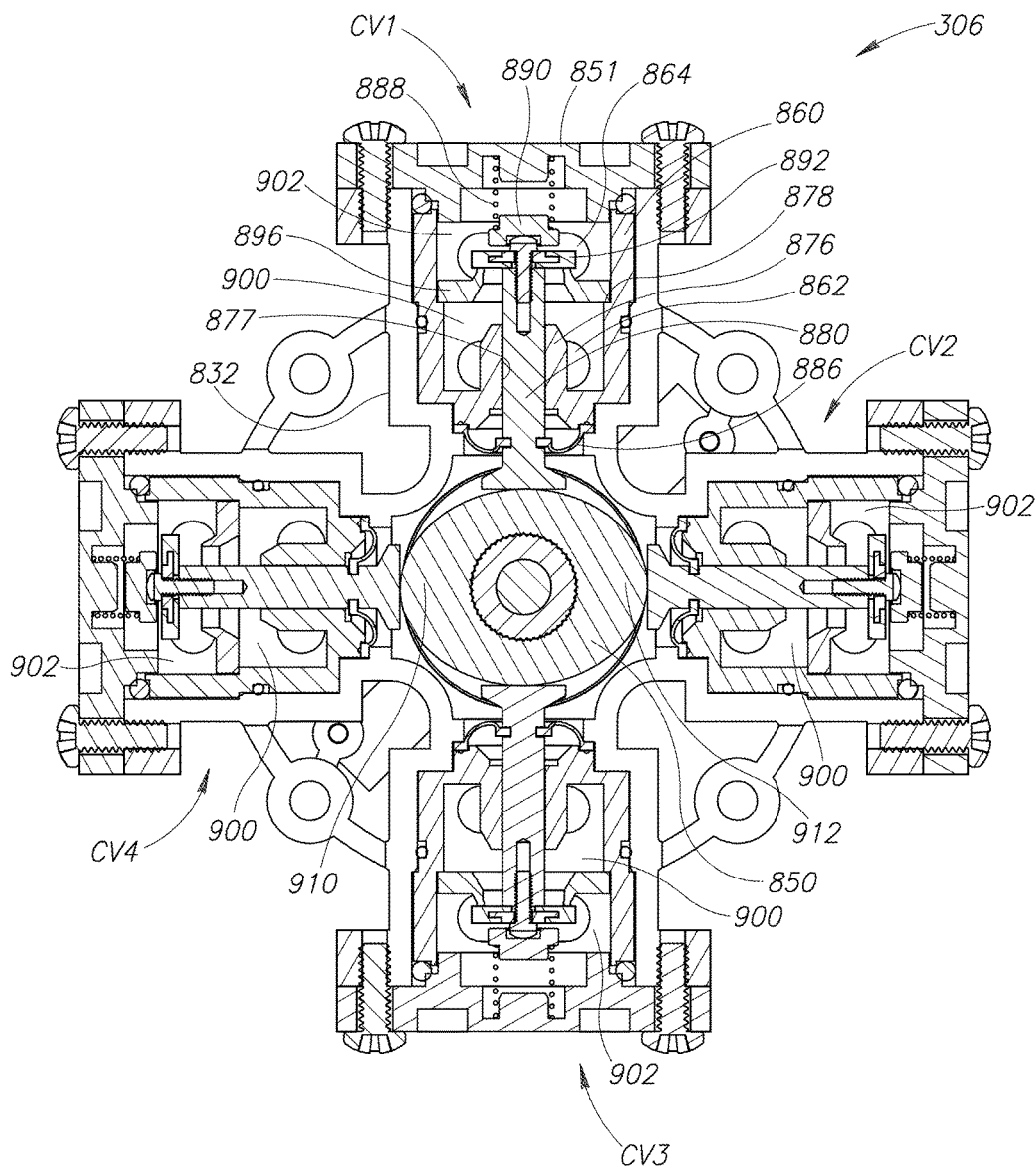
FIG. 10F is a cross-sectional view of the first rotary valve assembly with its second and fourth poppet valves open.
Figure 10G:
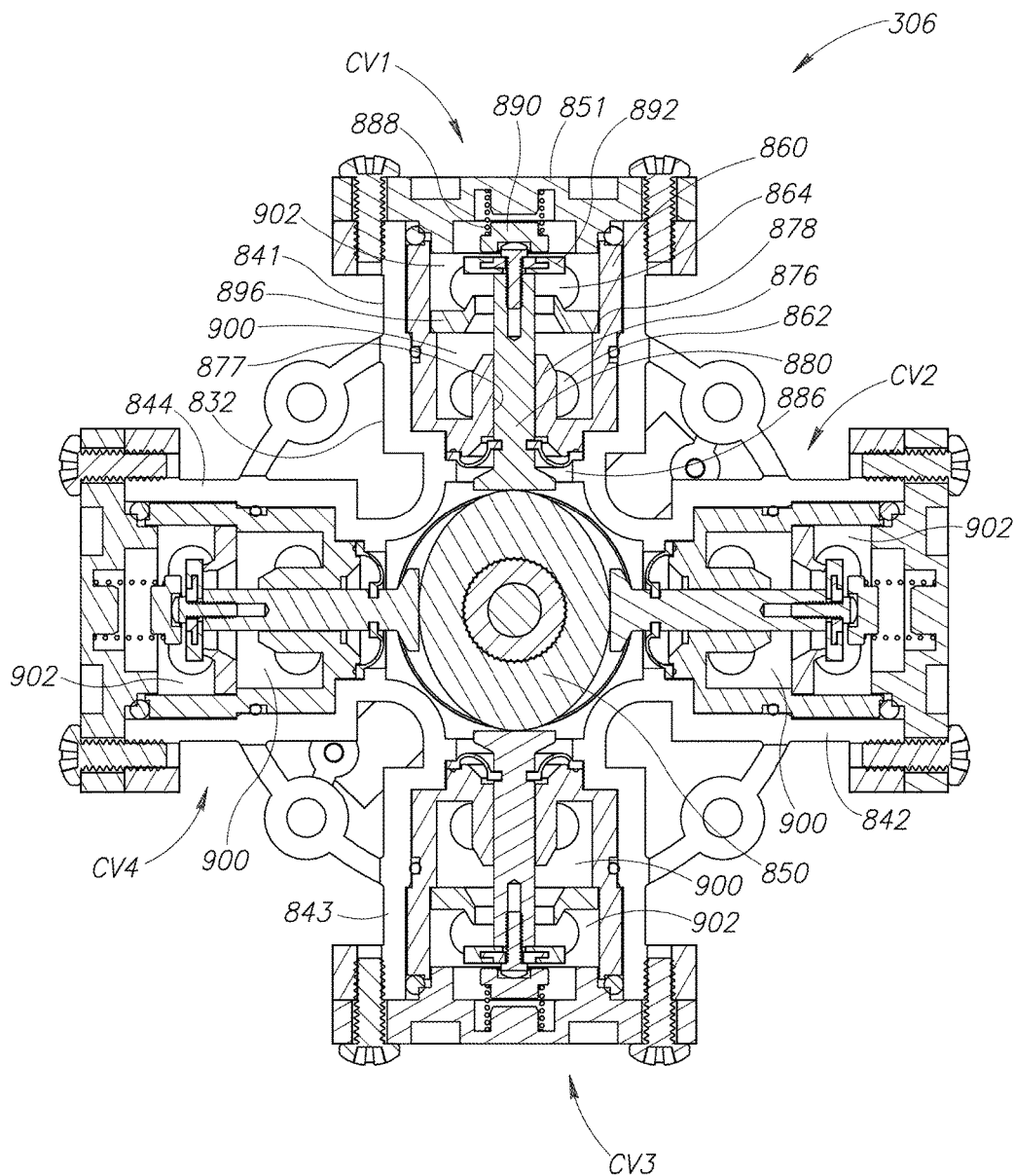
FIG. 10G is a cross-sectional view of the first rotary valve assembly with its first and third poppet valves open.

FIG. 10F is a cross sectional view of the first rotary valve assembly 306 with the cam 850 positioned to open the poppet valves CV2 and CV4. FIG. 10G is a cross sectional view of the first rotary valve assembly 306 with the cam 850 positioned to open the poppet valves CV1 and CV3.

Referring to FIG. 10F, a generally cylindrically shaped guide portion 876 extends inwardly from the open proximal end portion 870 (see FIG. 10E) of the housing 860. An open-ended channel 877 is formed in the guide portion 876. A shoulder 878 is formed on the inside the housing 860 between the lateral inlet and outlet 862 and 864.

Turning to FIG. 10E, inside the housing 860, the poppet valve CV1 has a pushrod 880 biased away from the end cap 851 by a biasing assembly 884. Referring to FIG. 10F, the pushrod 880 extends through the channel 877 and exits the housing 860 though the open proximal end portion 870 (see FIG. 10E). Turning to FIG. 10E, the pushrod 880 may have a circumferential recess 879 form near its proximal end portion 881.

A ring-shaped diaphragm 886 may extend around the pushrod 880 near the proximal end portion 881. In the embodiment illustrated, the diaphragm 886 has a circular central portion P2 having a center aperture 887 through which the pushrod 880 extends with the inner edge portion of the central portion P2 positioned within the recess 879, and thereby the central portion P2 firmly grips the pushrod 880. The diaphragm 886 may close and seal the open proximal end portion 870 of the housing 860. However, the diaphragm 886 may flex or stretch longitudinally to allow the pushrod 880 to move longitudinally with respect to the housing 860. In the embodiment illustrated in FIG. 10F, the diaphragm 886 has a circular outer peripheral portion P1 positioned between the open proximal end portion 870 of the housing 860 and the outer housing 832, and thereby the outer peripheral portion P1 is firmly clamped in place.

Referring to FIG. 10E, the circular outer peripheral portion P1 of the diaphragm 886 is connected to the circular central portion P2 by a curved or contoured intermediate portion P3. The intermediate portion P3 may be characterized as being a convolute. A circle positioned midway between the outer peripheral portion P1 and the central portion P2 may be characterized as being located at the center of the convolute. The diaphragm 886 has an effective area which extends from the circle at the center of the convolute to the central portion P2.

Turning to FIG. 10E, the pushrod 880 has a distal end portion 882 opposite the proximal end portion 881. The proximal end portion 881 has a cam follower 883 (see FIGS. 10C and 10E) formed therein. In the embodiment illustrated, the proximal end portion 881 may taper outwardly and be generally cone-shaped. The cam follower 883 (see FIG. 10C) may be implemented as a planar or contoured lower surface of the proximal end portion 881.

A ring-shaped seat 896 is fixedly attached to the shoulder 878 formed on the inside the housing 860. In the embodiment illustrated, the seat 896 has a central through-hole 897 through which the pushrod 880 extends unobstructed.

The distal end portion 882 of the pushrod 880 has a longitudinally extending channel 885 formed therein. The channel 885 is open at the distal end portion 882 of the pushrod 880. A disc-shaped poppet member 892 is fastened to the distal end portion 882 of the pushrod 880 by a fastener 894 (e.g., a bolt, screw, and the like) that extends into the open end of the channel 885. Thus, the fastener 894 couples the poppet member 892 to the distal end portion 882 of the pushrod 880, which moves therewith as a unit when the pushrod 880 moves inside the housing 860.

Referring to FIG. 10F, when the poppet member 892 is pressed against the seat 896, the poppet member 892 closes the central through-hole 897 and divides the interior of the housing 860 into a proximal chamber 900 and a distal chamber 902. Thus, the poppet member 892 may seal the proximal and distal chambers 900 and 902 from one another. The lateral inlet 862 is in communication with the proximal chamber 900, and the lateral outlet 864 is in communication with the proximal chamber 900. On the other hand, referring to FIG. 10G, when the poppet member 892 is spaced apart distally from the seat 896, the central through-hole 897 is uncovered and the proximal and distal chambers 900 and 902 are in communication with one another. Thus, in this configuration, a gas or mixture of gases may flow between the proximal and distal chambers 900 and 902. In other words, a pathway is opened between the lateral inlet and outlet 862 and 864.

The distal end portion 882 of the pushrod 880 is adjacent the biasing assembly 884. In the embodiment illustrated, the biasing assembly 884 includes a biasing member 888 (e.g., a coil spring), and an end cap 890. The biasing member 888 applies an inwardly directed force on the pushrod 880, which helps insure the pushrod 880 maintains contact with the cam 850. The end cap 890 rests upon the fastener 894 and is positioned between the disc-shaped poppet member 892 and the end cap 851. The biasing member 888 extends between the end cap 890 and the end cap 851 and applies the biasing force to the end cap 890, which translates that force to the fastener 894 and/or the poppet member 892. In turn, the fastener 894 and/or the poppet member 892 translates the biasing force to the pushrod 880.

The cam 850 may be characterized as having two lobes or high points 910 and 912 opposite one another. When one of the high points 910 and 912 is adjacent the cam follower 883 (see FIGS. 10C and 10E) of the pushrod 880 of the poppet valve CV1, the high point 910 or 912 pushes the pushrod 880 outwardly toward the end cap 851. This pushes the disc-shaped poppet member 892 away from the seat 896 (as illustrated in FIG. 10G) and opens the central through-hole 897. This opens the poppet valve CV1 and allows a gas or mixture of gases to flow though the poppet valve CV1. On the other hand, as illustrated in FIG. 10G, when neither of the high points 910 and 912 are adjacent the cam follower 883 (see FIGS. 10C and 10E) of the pushrod 880 of the poppet valve CV1, the pushrod 880 is biased inwardly away from the end cap 851 by the biasing assembly 884. The pushrod 880 thereby pulls the disc-shaped poppet member 892 toward the seat 896 causing the poppet member 892 to cover or close the central through-hole 897. This closes the poppet valve CV1 and prevents a gas or mixture of gases from flowing though the poppet valve CV1.

Because the ventilator 100 may be required to function over a long life span (e.g., more than about 30,000 hours), the first rotary valve assembly 306 may experience about 15,000,000 VPSA cycles. To satisfy this requirement, each of the poppet valves CV1-CV4 may have a "balanced" valve configuration. Whenever one of the poppet valves CV1-CV4 is closed, pressure inside the proximal chamber 900 acts upon both the effective area of the diaphragm 886 and a portion of the poppet member 892 covering (or closing) the central through-hole 897 of the seat 896. The area of the portion of the poppet member 892 covering (or closing) the central through-hole 897 of the seat 896 is approximately equal to the effective area of the diaphragm 886. When the pressure inside the proximal chamber 900 is negative (or a vacuum), an inwardly (toward the proximal chamber 900) directed force acts upon the effective area of the diaphragm 886. At the same time, an inwardly (toward the proximal chamber 900) directed force acts on the portion of the poppet member 892 covering the central through-hole 897 of the seat 896. Similarly, when the pressure inside the proximal chamber 900 is positive, an outwardly (away from the proximal chamber 900) directed force acts upon the effective area of the diaphragm 886 and an outwardly (away from the proximal chamber 900) directed force acts on the portion of the poppet member 892 covering the central through-hole 897 of the seat 896. Thus, when the proximal chamber 900 is sealed by the poppet member 892, forces directed in opposite directions act upon the effective area of the diaphragm 886 and the area of the portion of the poppet member 892 covering (or closing) the central through-hole 897 of the seat 896. Because (as mentioned above), the effective area of the diaphragm 886 and the area of the portion of the poppet member 892 covering (or closing) the central through-hole 897 of the seat 896 are approximately equal, net force on the pushrod 880 is zero. This balancing feature helps reduce the force of the pushrod 880 on the cam follower 883 and the cam 850, thereby reducing the wear and extending the life.

As explained above, each of the poppet valves CV1-CV4 is biased into a closed position by its biasing assembly 884. Each of the poppet valves CV1-CV4 includes the cam follower 883 (see FIGS. 10C and 10E) that abuts the cam 850. As the cam 850 rotates, it pushes opposing ones of the poppet valves CV1-CV4 outwardly opening them. If the poppet valves CV1 and CV3 are in open positions, the poppet valves CV2 and CV4 are in closed positions and vice versa. Referring to FIG. 7B, the first rotary valve assembly 306 (e.g., the stepper motor 833) is configured to receive a control signal 376 from the control system 220 encoding a cam position. The first rotary valve assembly 306 (e.g., the stepper motor 833) is also configured to rotate the cam 850 to the position encoded in the control signal 376.

Referring to FIG. 7A, the poppet valve CV3 (see FIG. 10G) is connected to the compressor 302 and the adsorption bed 300. The control system 220 makes the pressure inside the distal chamber 902 of the poppet valve CV3 less than the pressure inside the proximal chamber 900 of the poppet valve CV3 by configuring the compressor 302 to provide suction to the distal chamber 902.

The poppet valve CV1 (FIG. 10G) is connected to the compressor 302 and the outlet vent 124. The control system 220 makes the pressure inside the distal chamber 902 of the poppet valve CV1 less than the pressure inside the proximal chamber 900 of the poppet valve CV1 by configuring the compressor 302 to push the nitrogen-rich gas 122 (see FIGS. 8C and 8D) into the proximal chamber 900.

When the poppet valves CV1 and CV3 are open as illustrated in FIG. 10G, the poppet valve CV3 receives the nitrogen-rich gas 122 (see FIGS. 8C and 8D) from the adsorption bed 300 and provides it to the compressor 302. At the same time, the poppet valve CV1 allows the nitrogen-rich gas 122 pumped from the adsorption bed 300 (via the poppet valve CV3) by the compressor 302 to flow out of the compressor 302 and exit the ventilator 100 via the outlet vent 124. Optionally, the poppet valve CV3 may be connected to the second rotary valve assembly 330. As will be explained below, the compressor 302 may provide the suction 154 to the suction assembly 152 via the second rotary valve assembly 330.

Referring to FIG. 7A, the poppet valve CV4 (see FIG. 10F) is connected to the compressor 302 and the patient air intake 116. The control system 220 makes the pressure inside the proximal chamber 900 of the poppet valve CV4 less than the pressure inside the distal chamber 902 of the poppet valve CV4 by configuring the compressor 302 to provide suction to the proximal chamber 900.

The poppet valve CV2 (see FIG. 10F) is connected to the compressor 302 and the adsorption bed 300. The control system 220 makes the pressure inside the distal chamber 902 of the poppet valve CV2 greater than the pressure inside the proximal chamber 900 of the poppet valve CV2 by configuring the compressor 302 to provide the pressurized air 114 pumped by the compressor 302 to the distal chamber 902.

When the poppet valves CV2 and CV4 are open as illustrated in FIG. 10F, the poppet valve CV4 allows the air 114 to be pumped via the patient air intake 116 into the compressor 302. At the same time, the poppet valve CV2 provides the pressurized air 114 from the compressor 302 to the adsorption bed 300. Optionally, the poppet valve CV2 may be connected to the second rotary valve assembly 330. As will be explained below, the gases 164 provided to the second rotary valve assembly 330 may be used to implement the nebulizer assembly 162.

Figure 11:
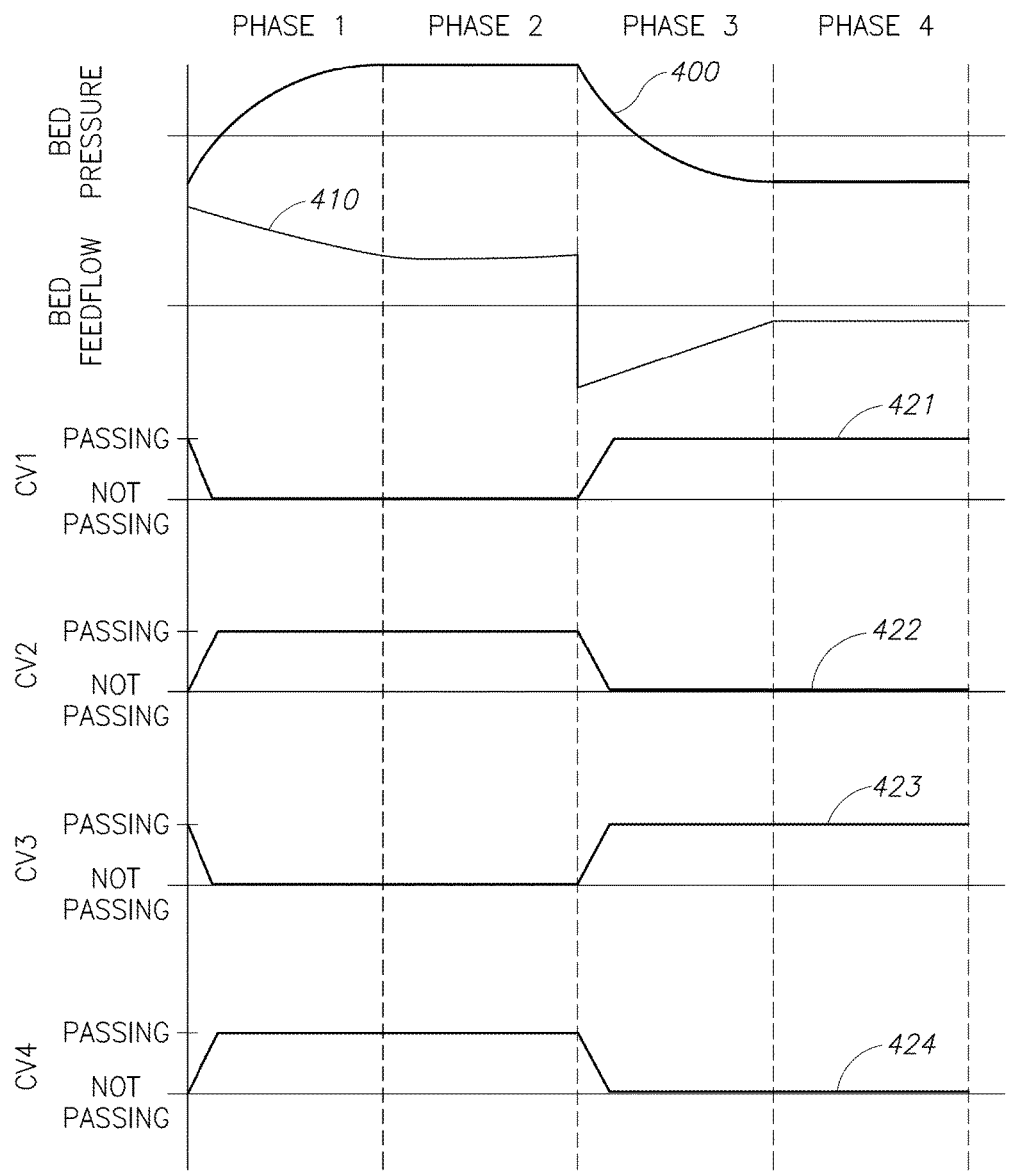
FIG. 11 is a graph showing pressure and feed flow experienced by a bed of nitrogen adsorbent material of the oxygen generator during the four phases of the VPSA process.

As mentioned above, in the embodiment illustrated, the oxygen assembly 210 generates the oxygen 364 (see FIG. 8B) using the VPSA process, which may have four phases that are labeled "PHASE 1," "PHASE 2," "PHASE 3," and "PHASE 4" across the top of FIG. 11.

In FIG. 11, an upper line 400 depicts pressure experienced by the bed of nitrogen adsorbent material 344 (see FIGS. 8A-8D) during the four phases of the VPSA process. Referring to FIG. 11, the line 400 may be determined by the control system 220 based on the electrical pressure signal 374 (see FIG. 7B) provided by the pressure transducer PT2. A lower line 410 depicts feed flow rate through the bed of nitrogen adsorbent material 344 (see FIGS. 8A-8D) during the four-phases of the VPSA process.

Lines 421 and 423 show that the poppet valves CV1 and CV3, respectively, are transitioned from open ("passing") to closed ("not passing") at the beginning of the first phase and then the poppet valves CV1 and CV3 are transitioned from closed ("not passing") to open ("passing") at the beginning of third phase. Thus, the poppet valves CV1 and CV3 are closed during most of the first phase and all of the second phase. Further, the poppet valves CV1 and CV3 are open during most of the third phase and all of the fourth phase.

Conversely, lines 422 and 424 show that the poppet valves CV2 and CV4, respectively, are transitioned from closed ("not passing") to open ("passing") at the beginning of the first phase and then the poppet valves CV2 and CV4 are transitioned from open ("passing") to closed ("not passing") at the beginning of third phase. Thus, the poppet valves CV2 and CV4 are open during most of the first phase and all of the second phase. Further, the poppet valves CV2 and CV4 are closed during most of the third phase and all of the fourth phase.

Figure 12:
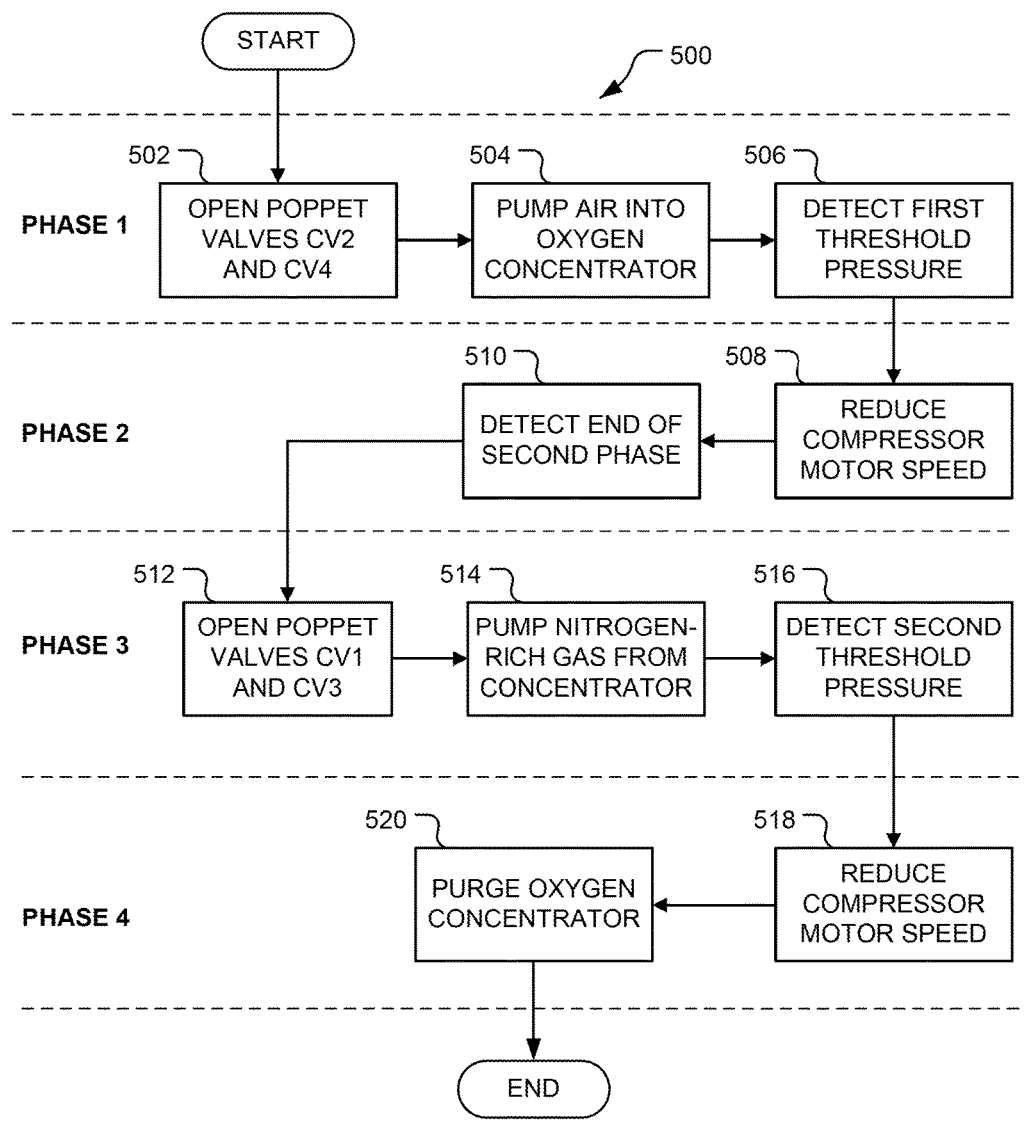
FIG. 12 is a flow diagram of a method performed by the control system of the ventilator of FIG. 1.

FIG. 12 is a flow diagram of a method 500 performed by the control system 220. The method 500 at least partially implements the VPSA process. As the method 500 is performed, the pressure transducer PT2 (see FIGS. 7A and 7B) occasionally obtains pressure values for the adsorption bed 300 and sends the electrical pressure signal 374 to the control system 220.

In first block 502, the control system 220 begins the first phase of the VPSA process by opening the poppet valves CV2 and CV4, and closing the poppet valves CV1 and CV3. At this point, the pressure regulator R2 is closed.

In next block 504, the control system 220 instructs the motor 350 of the compressor 302 to pump the air 114 from the patient air intake 116 into the adsorption bed 300. The motor 350 of the compressor 302 may run at a relatively high speed while drawing the air 114 from the patient air intake 116.

In block 506, the control system 220 determines that the pressure inside the adsorption bed 300 has reached the first threshold pressure value (e.g., approximately 10 PSIG). When the pressure inside the adsorption bed 300 reaches the first threshold pressure value, the pressure regulator R2 automatically opens. At this point, the first phase ends and the second phase begins. During the second phase, nitrogen is adsorbed by the adsorption bed 300 from the air 114 and referring to FIG. 8B, the oxygen 346 (e.g., 90% pure oxygen) flows out of the adsorption bed 300 through the pressure regulator R2. The oxygen that passes through the pressure regulator R2 during the second phase is stored in the oxygen tank 312.

Returning to FIG. 12, in next block 508, at the start of the second phase, the control system 220 reduces the speed of the motor 350. Referring to FIG. 8B, during the second phase, a mass transfer zone 430 moves away from the first end 341 (in a direction identified by an arrow "D1") through to the second end 343. Gas on a first side 432 of the mass transfer zone 430 near the first end 341 is air, and gas on a second side 434 of the mass transfer zone 430 near the second end 343 is about 90% oxygen. The compressor 302 may run relatively slowly during the second phase to facilitate effective nitrogen adsorbtion. In block 510, the control system 220 detects the end of the second phase, which ends when the mass transfer zone 430 reaches the second end 343. The control system 220 may determine the second phase has ended after a predetermined amount of time (e.g., about one second) has elapsed. In some embodiments, the control system 220 may also use a secondary means (e.g., pressure) to help determine when the second phase has ended. At this point, the adsorption bed 300 is fully saturated with nitrogen, the second phase ends, and the third phase begins.

At the start of the third phase, in block 512, the control system 220 opens the poppet valves CV1 and CV3, and closes the poppet valves CV2 and CV4. At this point, the pressure regulator R1 is closed.

In next block 514, the control system 220 instructs the motor 350 of the compressor 302 to pump the nitrogen-rich gas 122 from the adsorption bed 300 and into the external environment through the outlet vent 124. The compressor 302 may run at a relatively high speed as it draws the nitrogen-rich gas 122 out of the adsorption bed 300.

In block 516, the control system 220 determines that the pressure inside the adsorption bed 300 has reached the second threshold pressure value (e.g., approximately −7 PSIG). At this point, the third phase ends and the fourth phase begins.

At the beginning of the fourth phase, in block 518, the control system 220 may reduce the speed of the motor 350 to a relatively slow speed.

In block 520, the control system 220 purges the adsorption bed 300 with oxygen from the oxygen tank 312. In block 520, the pressure regulator R1 opens automatically to allow the flow of "purge" oxygen 348 (see FIG. 8D) from the oxygen tank 312 to flow through the adsorption bed 300 (e.g., in a direction identified by an arrow "D2"). The mass transfer zone 430 also moves away from the second end 343 (in a direction identified by an arrow "D2") through to the first end 341. The low pressure inside the adsorption bed 300 combined with the flow of purge oxygen 348 draws the nitrogen out and regenerates the adsorption bed 300. When the purge is completed, the fourth phase ends, which completes one four-phase cycle, and the method 500 terminates. The control system 220 may begin another cycle by returning to block 502 of the method 500.

FIGS. 13A-13D are schematic diagrams of the second rotary valve assembly 330. The second rotary valve assembly 330 may be substantially similar to the first rotary valve assembly 306 (see FIGS. 10A and 10B). However, the second rotary valve assembly 330 includes a cam 530 with a single lobe or high point 532, which is unlike the cam 850 of the first rotary valve assembly 306, which has two high points 910 and 912 (see FIG. 10F) opposite one another.

Referring to FIGS. 13A-13D, the cam 530 of the second rotary valve assembly 330 is configured to selectively actuate four poppet valves CV5-CV8 one at a time. Each of the poppet valves CV5-CV8 may be substantially similar to the poppet valve CV1 illustrated in FIG. 10E.

In the second rotary valve assembly 330, the poppet valves CV5 and CV7 are positioned opposite one another. Similarly, the poppet valves CV6 and CV8 are positioned opposite one another. The poppet valves CV5-CV8 are biased into a closed position. Each of the poppet valves CV5-CV8 has a pushrod 538 (substantially similar to the pushrod 880 depicted in FIG. 10E) with a cam follower 540 (substantially similar to the cam follower 883 depicted in FIG. 10C) that abuts the cam 530. As the cam 530 rotates, it pushes only one of the pushrods 538 of the poppet valves CV5-CV8 at a time outwardly and into an open position.

Further, as explained above with respect to the first rotary valve assembly 306, each of the poppet valves CV5-CV8 may include a poppet member (substantially identical to the poppet member 892) configured to move with respect to a seat (substantially identical to the seat 896) to selectively connect a proximal chamber (like the proximal chamber 900) with a distal chamber (like the distal chamber 902). In such embodiments, after the cam 530 pushes the pushrod 538 of a selected one of the poppet valves CV5-CV8 outwardly, the selected poppet valve opens.

Referring to FIG. 7B, the second rotary valve assembly 330 includes a stepper motor 542 and a position sensor 544 substantially similar to the stepper motor 833 and the position sensor 834 of the first rotary valve assembly 306. The second rotary valve assembly 330 (e.g., the stepper motor 542) is configured to receive a control signal 546 from the control system 220 encoding a cam position. The second rotary valve assembly 330 (e.g., the stepper motor 542) is also configured to rotate the cam 530 to the position encoded in the control signal 546. The position sensor 544 provides a position signal 548 to the control system 220 that encodes whether the stepper motor 542 and/or the cam 530 is in a home position (e.g., true or "on") or at a position other than the home position (e.g., false or "off").

Figure 13A:
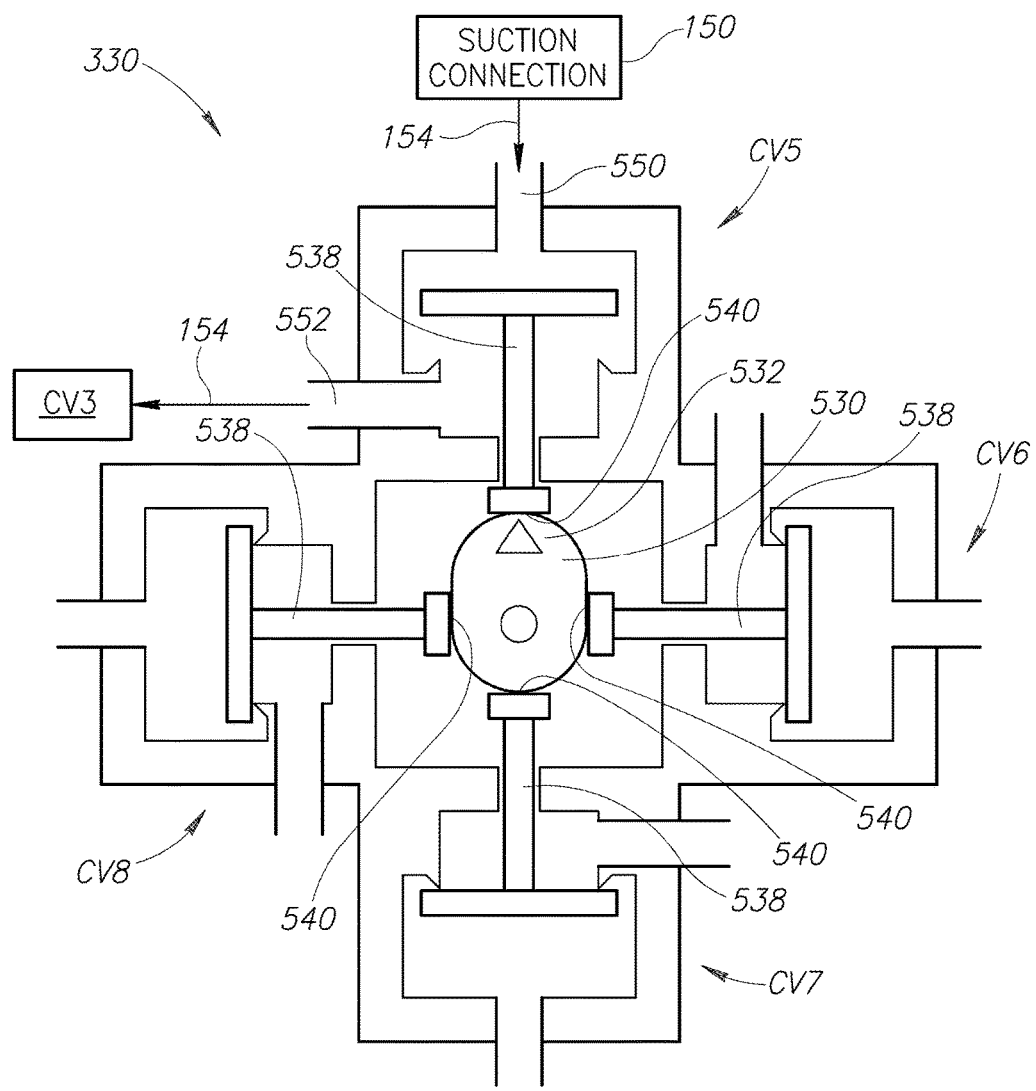
FIG. 13A is an illustration of an optional second rotary valve assembly of the oxygen assembly depicted with a first one of its four poppet valves open.

Referring to FIG. 13A, the poppet valve CV5 has an inlet 550 connected to the suction connection 150 and an outlet 552 connected to the poppet valve CV3 (see FIGS. 10D, 10F, and 10G). When the poppet valves CV1 and CV3 are open, the poppet valve CV5 may be opened (as shown in FIG. 13A) to receive the suction 154 from the compressor 302 and provide the suction 154 to the suction connection 150. Any gases received from the suction assembly 152 (see FIG. 1) via the suction connection 150, may be pumped by the compressor 302 out the outlet vent 124 via the poppet valve CV1. The nitrogen-rich gas 122 may be pumped by the compressor 302 at the same time the suction 154 is provided.

Figure 13B:
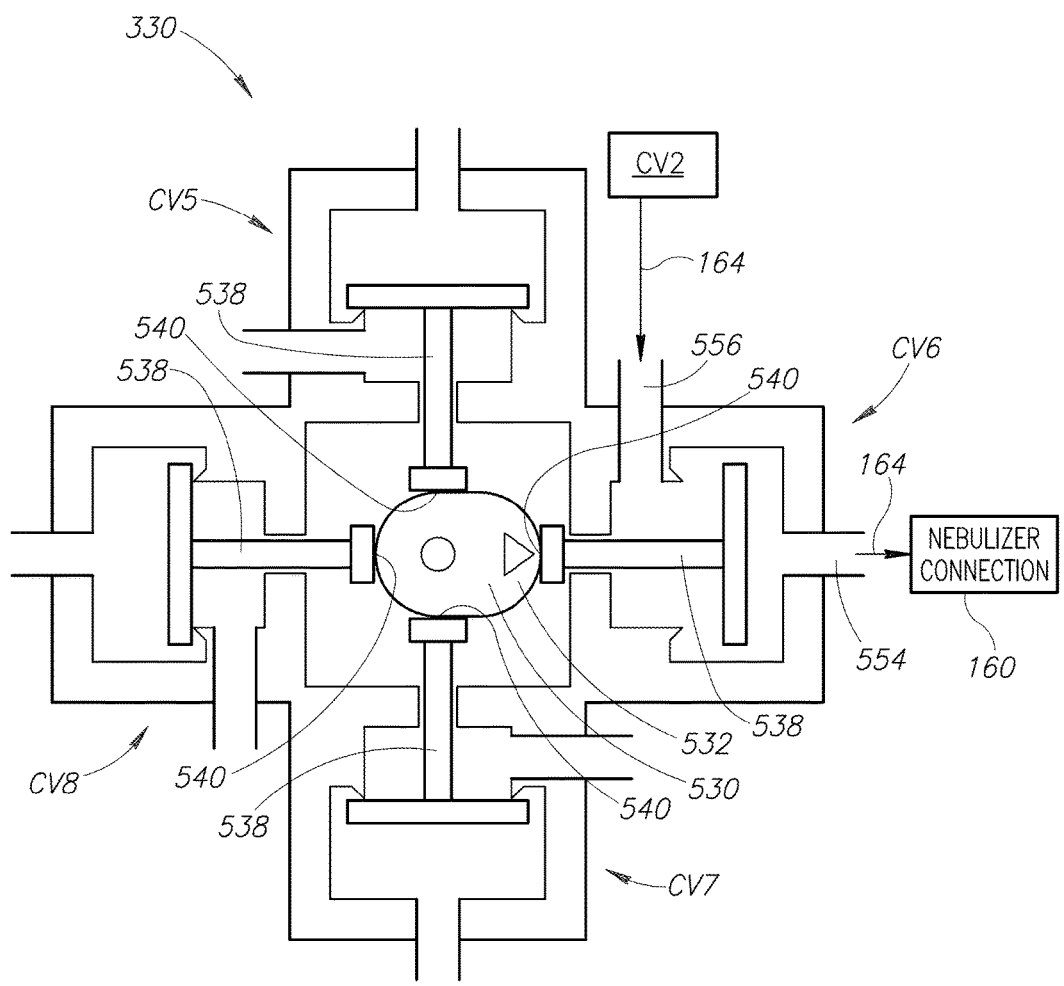
FIG. 13B is an illustration of the optional second rotary valve assembly of the oxygen assembly depicted with a second one of its four poppet valves open.

Referring to FIG. 13B, the poppet valve CV6 has an inlet 554 connected to the nebulizer assembly 162 and an outlet 556 connected to the poppet valve CV2. When the poppet valves CV2 and CV4 are open, the poppet valve CV6 may be opened (as shown in FIG. 13B) to provide the gases 164 to the nebulizer connection 160 instead of providing the air 114 to the adsorption bed 300. Thus, the compressor 302 may power the nebulizer assembly 162 (see FIG. 1).

Figure 13C:
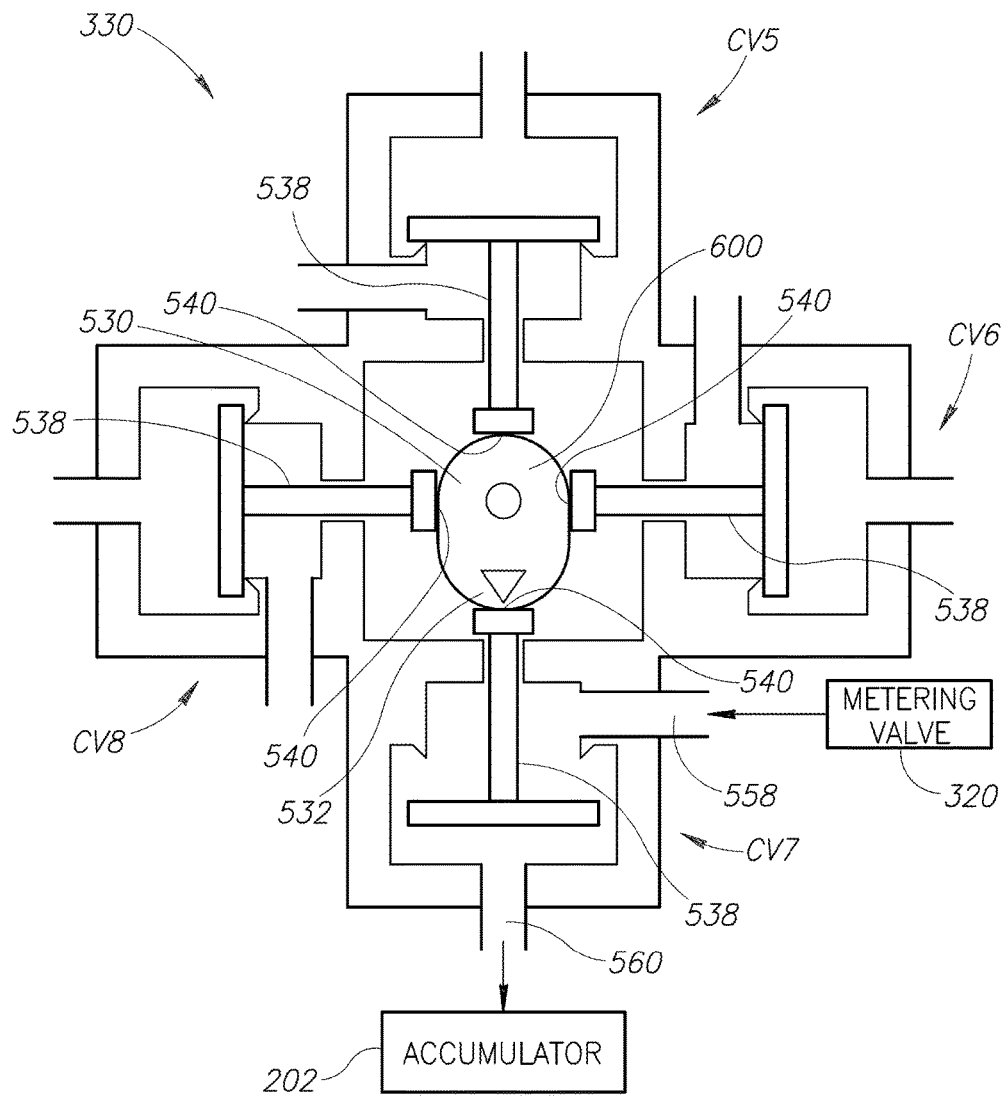
FIG. 13C is an illustration of the optional second rotary valve assembly of the oxygen assembly depicted with a third one of its four poppet valves open.

Referring to FIG. 13C, the poppet valve CV7 has an inlet 558 connected to the metering valve 320 and an outlet 560 connected to the accumulator 202. When the poppet valve CV7 is open as shown in FIG. 13C, oxygen output from the metering valve 320 is provided to the accumulator 202.

Figure 13D:
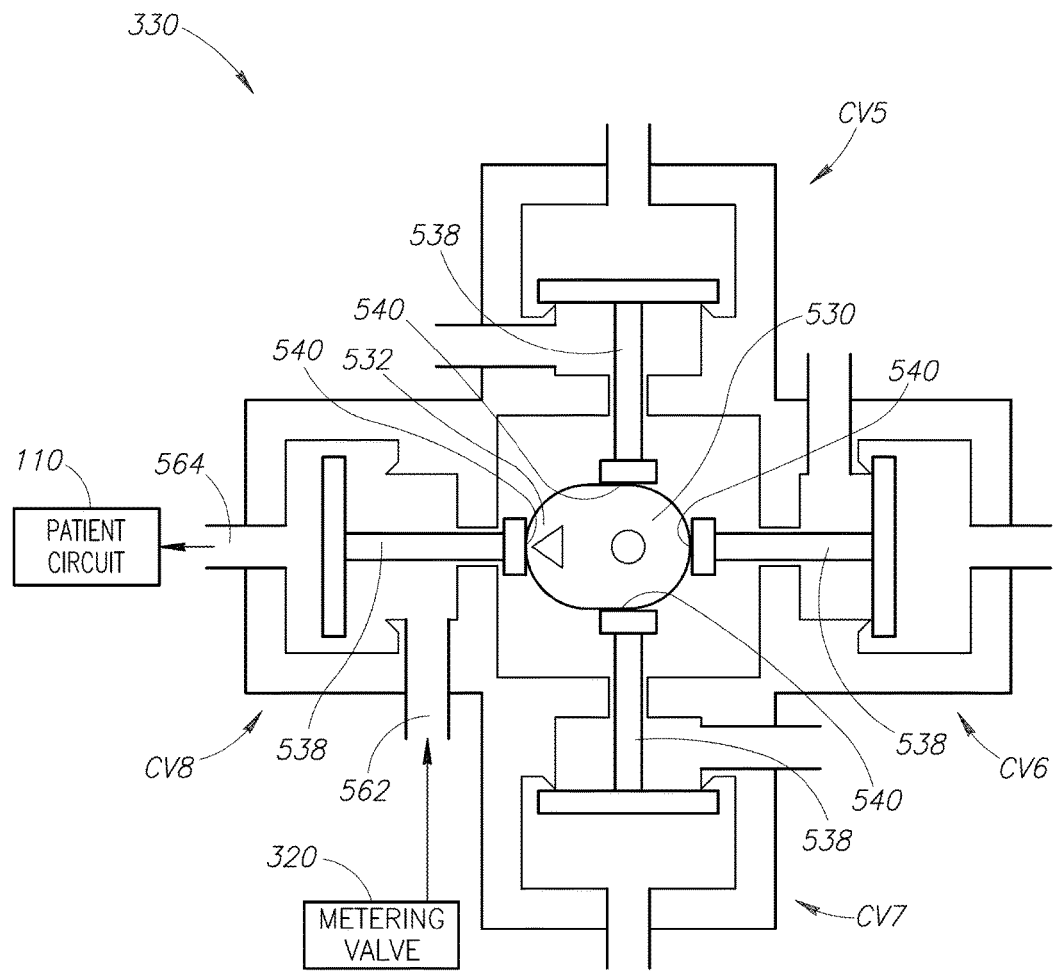
FIG. 13D is an illustration of the optional second rotary valve assembly of the oxygen assembly depicted with a fourth one of its four poppet valves open.

Referring to FIG. 13D, the poppet valve CV8 has an inlet 562 connected to the metering valve 320 and an outlet 564 connected to the patient circuit 110. When the poppet valve CV8 is open as shown in FIG. 13D, the oxygen 364 (from the adsorption bed 300) and/or the oxygen from the oxygen tank 312 is provided directly to the patient circuit 110.

Control System

Referring to FIGS. 5B and 7B, the control system 220 includes a memory 700 connected to one or more processors 710. The memory stores the table 362 and instructions 720 executable by the processor(s) 710.

The processor(s) 710 may be implemented by one or more microprocessors, microcontrollers, application-specific integrated circuits ("ASIC"), digital signal processors ("DSP"), combinations or sub-combinations thereof, or the like. The processor(s) 710 may be integrated into an electrical circuit, such as a conventional circuit board, that supplies power to the processor(s) 710. The processor(s) 710 may include internal memory and/or the memory 700 may be coupled thereto. The present invention is not limited by the specific hardware component(s) used to implement the processor(s) 710 and/or the memory 700.

The memory 700 is a computer readable medium that includes instructions or computer executable components that are executed by the processor(s) 710. The memory 700 may be implemented using transitory and/or non-transitory memory components. The memory 700 may be coupled to the processor(s) 710 by an internal bus 715.

The memory 700 may include random access memory ("RAM") and read-only memory ("ROM"). The memory 700 contains instructions and data that control the operation of the processor(s) 710. The memory 700 may also include a basic input/output system ("BIOS"), which contains the basic routines that help transfer information between elements within the ventilator 100.

Optionally, the memory 700 may include internal and/or external memory devices such as hard disk drives, floppy disk drives, and optical storage devices (e.g., CD-ROM, R/W CD-ROM, DVD, and the like). The ventilator 100 may also include one or more I/O interfaces (not shown) such as a serial interface (e.g., RS-232, RS-432, and the like), an IEEE-488 interface, a universal serial bus ("USB") interface, a parallel interface, and the like, for the communication with removable memory devices such as flash memory drives, external floppy disk drives, and the like.

The processor(s) 710 is configured to execute software implementing the VPSA process (which may include performing the method 500 illustrated in FIG. 12) and/or delivering oxygen in accordance with oxygen delivery methods described below. Such software may be implemented by the instructions 720 stored in memory 700.

Oxygen Delivery

Referring to FIG. 1, as mentioned above, the ventilator 100 delivers the inspiratory gases 108 directly to the patient connection 106 (via the patient circuit 110). Oxygen may be delivered to the patient 102 in one of two ways: (1) as pulses of oxygen 140 delivered directly to the patient connection 106, or (2) in the gases 112 that contain the air 114 optionally blended with the oxygen 250 and/or the low pressure oxygen 128 in the accumulator 202.

Figure 14A:
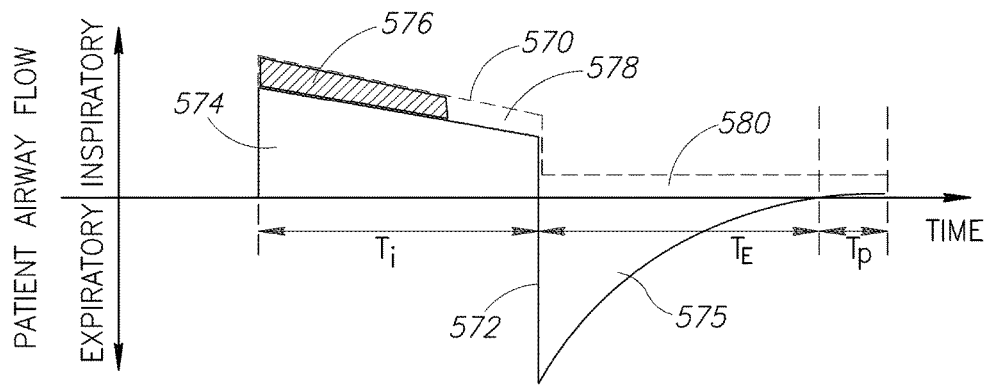
FIG. 14A is a graph showing patient airway flow using a prior art ventilator during both inspiratory and expiratory phases.
Figure 14B:
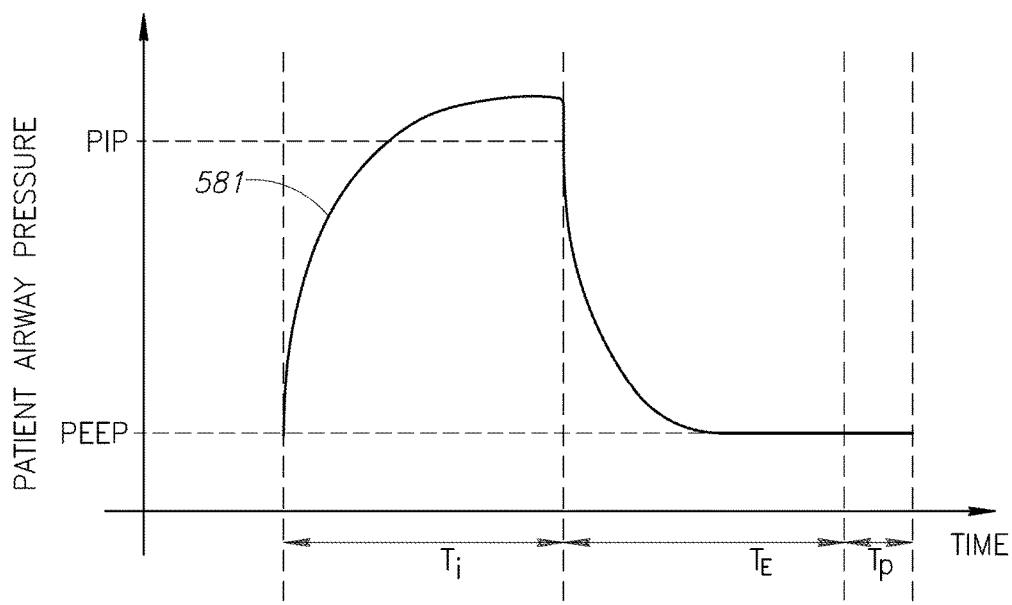
FIG. 14B is a graph showing patient airway pressure using the prior art ventilator during both the inspiratory and expiratory phases.

FIGS. 14A and 14B are graphs illustrating traditional delivery of oxygen by a conventional portable ventilator connected to an external low pressure continuous flow source, such as a stand-alone oxygen concentrator. In FIG. 14A, the conventional portable ventilator is using traditional volume controlled ventilation to deliver breaths. In both FIGS. 14A and 14B, the x-axis is time. The inspiratory phase occurs during the duration $T_I$. The exhalation phase occurs during a duration $T_E$. The pause occurs during a duration $T_P$.

In FIG. 14A, the y-axis is flow rate within the patient's airway. Referring to FIG. 14A, a dashed line 570 illustrates a continuous flow of oxygen delivered during both the inspiratory and expiratory phases. A solid line 572 illustrates a flow of air provided by the conventional portable ventilator during both the inspiratory and expiratory phases. The solid line 572 is determined by a set of desired ventilator settings.

An area 574 illustrates an inspiratory volume of air received by the patient, and an area 575 illustrates an expiratory volume of air expelled by the patient. The area 574 represents the desired total tidal volume selected by the user.

A shaded area 576 illustrates a volume of effective oxygen provided to the patient during the inspiratory phase. An area 578 illustrates a volume of oxygen that is delivered by the conventional portable ventilator during the inspiratory phase but is unusable (e.g., trapped in one or more anatomical dead spaces). Together the areas 576 and 578 form a volume of gases that exceed the desired ventilator settings (e.g., a desired total tidal volume). Specifically, together the areas 574, 576, and 578 form a total inspiratory volume (of oxygen and air) delivered by the conventional portable ventilator that exceeds the desired total tidal volume. An area 580 illustrates a volume of oxygen delivered by the conventional portable ventilator during the exhalation phase that is wasted by the conventional portable ventilator.

In FIG. 14B, the conventional portable ventilator is using traditional pressure controlled ventilation to deliver breaths. Referring to FIG. 14B, the y-axis is pressure within the patient's airway. A pressure value "PIP" identifies the peak inspiratory pressure input or desired by the user. A solid line 581 illustrates patient airway pressure during both the inspiratory and expiratory phases. Unfortunately, as FIG. 14B illustrates, the continuous flow of oxygen (illustrated in FIG. 14A by the dashed line 570) causes the pressure within the patient's airway to exceed the peak inspiratory pressure input by the user (the pressure value "PIP").

As shown in FIGS. 14A and 14B, the conventional portable ventilator is inefficient. For example, the conventional portable ventilator wastes all of the continuous flow of oxygen (illustrated in FIG. 14A by the dashed line 570) delivered during non-inspiratory time. Further, because the continuous flow of oxygen delivered to the patient is not controlled (e.g., by ventilator volume or inspiratory pressure settings), only a portion of the oxygen (illustrated by the shaded area 576) delivered is actually effective. Further, the continuous flow of oxygen causes the peak inspiratory pressure input by the user to be exceeded when pressure controlled ventilation is used. One reason for this problem is that the conventional ventilator does not know how much oxygen (e.g., volume or rate) is being delivered to the patient.

While FIGS. 14A and 14B depict the conventional portable ventilator using traditional volume controlled ventilation and traditional pressure controlled ventilation, respectively, to deliver breaths, a similar result occurs when the conventional portable ventilator uses other types of ventilation because the ventilator does not know how much oxygen (e.g., volume or rate) is being delivered to the patient. Thus, the ventilator cannot accurately configure the breaths delivered (e.g., to achieve either a desired flow rate or pressure in the patient's airway).

Figure 15B:
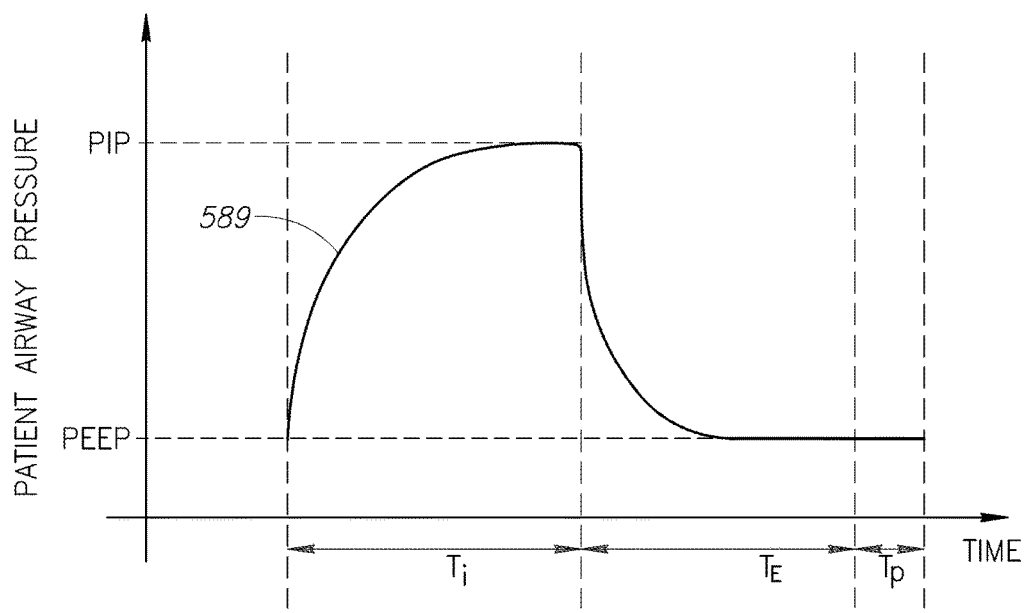
FIG. 15B is a graph showing patient airway pressure using the ventilator of FIG. 1 during both the inspiratory and expiratory phases.

FIGS. 15A and 15B are graphs illustrating oxygen delivery provided by the ventilator 100 illustrated in FIGS. 1 and 4. In FIG. 15A, the ventilator 100 is using volume controlled ventilation to deliver breaths. In both FIGS. 15A and 15B, the x-axis is time. The inspiratory phase occurs during the duration $T_I$. The exhalation phase occurs during the duration $T_E$. The pause occurs during the duration $T_P$.

Referring to FIG. 15A, a solid line 582 illustrates a flow of air provided by the ventilator 100 during both the inspiratory and expiratory phases. The solid line 582 is determined by a set of desired ventilator settings (e.g., values entered via the user interface 200 illustrated in FIG. 6). A shaded area 584 illustrates a volume of effective oxygen provided to the patient 102 at the beginning of the inspiratory phase. An area 586 illustrates a volume of air provided to the patient 102 during the inspiratory phase. Together the areas 584 and 586 form a total inspiratory volume (of oxygen and air) delivered by the ventilator 100. As mentioned above, this volume is also referred to as the total tidal volume. An area 588 illustrates an expiratory volume of air expelled by the patient 102.

FIG. 15A illustrates delivering one of the pulses of oxygen 140 (see FIG. 1) at the start of the inspiration phase before the gases 112 (see FIG. 1) are provided. For example, the ventilator 100 may wait until after the pulse of oxygen has been delivered before delivering the gases 112. Thus, at the start of each inspiration phase of each breath, the patient 102 (see FIG. 1) may be receiving only the pulse (or bolus) of oxygen from the ventilator 100. However, this is not a requirement. In alternate embodiments, the flow of the gases 112 may begin before the delivery of the bolus of oxygen has completed. In any event, the flow of the gases 112 are started before the end of the inspiration phase.

In FIG. 15B, the ventilator 100 is using pressure controlled ventilation to deliver breaths. Referring to FIG. 15B, the y-axis is pressure within the patient's airway. A solid line 589 illustrates patient airway pressure during both the inspiratory and expiratory phases. As FIG. 15B illustrates, the pressure within the patient's airway does not exceed the peak inspiratory pressure value input by the user (the pressure value "PIP") using the pressure control input 237 (see FIG. 6).

As shown in FIGS. 15A and 15B, the ventilator 100 is more efficient than the conventional portable ventilator. For example, the ventilator 100 does not provide a continuous flow of oxygen and therefore, avoids wasting oxygen during non-inspiratory times. Further, the total inspiratory volume is in accordance with (and does not exceed) the desired ventilator settings. And furthermore, the oxygen is delivered in the first part of the breath where the oxygen provides better oxygenation, as opposed to during the last part of the breath when the oxygen becomes trapped in the anatomical dead spaces. Further, because the ventilator 100 knows the total tidal volume delivered, the ventilator 100 may configure the breaths not to exceed a user supplied peak inspiratory pressure value (e.g., when pressure ventilation is used). Thus, one of ordinary skill in the art through application of the present teachings could configure the ventilator 100 to deliver any desired type of ventilation in which oxygen is delivered in the first part of the breath. Further, the delivery of the pulses of oxygen 140 (see FIG. 1) may begin before the initiation of each breath.

Referring to FIG. 13D, for pulse dose delivery, the control system 220 instructs the second rotary valve assembly 330 (via the control signal 546 depicted in FIG. 7B) to rotate the cam 530 to open the poppet valve CV8. The inspiratory phase may be initiated by either the control system 220 or the patient 102. After detecting the beginning of an inspiratory phase, the control system 220 instructs the stepper motor 322 of the metering valve 320 to deliver a desired dose or pulse of oxygen to the patient circuit 110, referred to as a "bolus." Thus, the ventilator 100 is configured to synchronize a bolus of oxygen with the patient's breathing. For example, the ventilator 100 may be configured to provide the volume (or bolus) of oxygen depicted by the area 584 of FIG. 15A.

The user interface 200 may be used to determine parameter values for the bolus. For example, if the oxygen flow equivalent input 244 (see FIG. 6) allows the user to select a numerical value (e.g., from 1 to 10), each successive number may represent an amount of "equivalent oxygenation" relative to a continuous flow of oxygen. For example, the number "2" may provide a bolus of oxygen at the beginning of a breath that would provide oxygenation equivalent to a bleed-in flow of oxygen at two liters per minute from an external source (e.g., the low pressure oxygen source 118 depicted in FIG. 1). By way of another non-limiting example, the user may select a numerical value within a predetermined range that represents from about 0.2 liters per minute to about 9 liters per minute in increments of about 0.1 liters per minute.

Because at least some of the oxygen delivered using a hypothetical continuous flow of oxygen is wasted, the control system 220 is configured to deliver an amount of oxygen in the bolus that is less than an amount of oxygen that would be delivered by the continuous flow of oxygen during the inspiration phase.

In alternate embodiments, the user may enter a pulse volume value using the oxygen pulse volume input 251 (see FIG. 6) that specifies the size of the bolus. The pulse volume value may be expressed in milliliters or a dimensionless value within a predetermined numerical range (e.g., from 1 to 10). In such embodiments, each successive number may represent a greater amount of oxygen.

The control system 220 adjusts the delivery of the breath to account for the bolus, and ensures that the breath is delivered in accordance with the user setting of tidal volume (entered via the tidal volume input 242 depicted in FIG. 6) or the peak inspiratory pressure value (e.g., entered via the pressure control input 237 depicted in FIG. 6). By way of a non-limiting example, the control system 220 may configure the bolus to have a volume that is less than about 75% of the total tidal volume delivered. By way of another non-limiting example, the control system 220 may configure the bolus to have a volume that is between about 50% and about 75% of the total tidal volume delivered.

Further, the ventilator 100 is configured to adjust the parameter values (e.g., volume, pressure, etc.) of the inspiratory gases 108 to assure the inspiratory gases 108 are delivered correctly. For example, if the user (e.g., a clinician) uses the tidal volume input 242 (see FIG. 6) to set the total tidal volume value to 500 ml, and the oxygen pulse volume input 251 (see FIG. 6) to set the pulse volume value to 100 ml, the control system 220 will set the air delivery from the accumulator 202 to 400 ml, thus providing the correct total volume (500 ml=400 ml+100 ml) to the patient circuit 110.

The control system 220 may deliver a user-set bolus of oxygen (e.g., in the gases 112 and/or the pulses of oxygen 140) to the patient connection 106. The size of the bolus is controlled by the metering valve 320. The control system 220 reduces the flow of the gases 252 (see FIG. 5A) as measured by the internal flow transducer 212 (and encoded in the flow signal 270 illustrated in FIG. 5B) to satisfy a user set tidal volume value (when volume ventilation is used) or a user set peak inspiratory pressure value (when pressure ventilation is used).

The total inspiratory flow rate and volume of the gases 112 (see FIG. 1) may be determined using the flow signal 270 (see FIG. 5B), and the pulse volume may be determined using the signal 358 (see FIG. 7B) and the stepper position value (described above) of the metering valve 320. Further, the control system 220 controls the pulse (or bolus) volume using the control signal 360 (see FIG. 7B) sent to the stepper motor 322 (see FIG. 7B) of the metering valve 320. The control system 220 sets the air delivery from the accumulator 202 using the control signal 278 (see FIG. 5B) sent to the motor 272 of the blower 222.

Referring to FIG. 13C, for mixed oxygen delivery, the cam 530 of the second rotary valve assembly 330 is positioned so that the poppet valve CV7 is in the open position. The control system 220 determines the oxygen flow required at a given time to achieve a FI02 input by the user (e.g., via the FI02 input 246 depicted in FIG. 6). The FI02 may be expressed within a range (e.g., about 21% to about 100%). The control system 220 may use the control signal 360 (see FIG. 7B) to position the metering valve 320 to achieve the desired oxygen flow. The control system 220 may use the oxygen concentration signal 276 (see FIG. 5B) from the oxygen sensor 227 to monitor the gases 252 that pass through the internal bacterial filter 230 and emerge as the gases 112.

Suction Assembly

Figure 16:
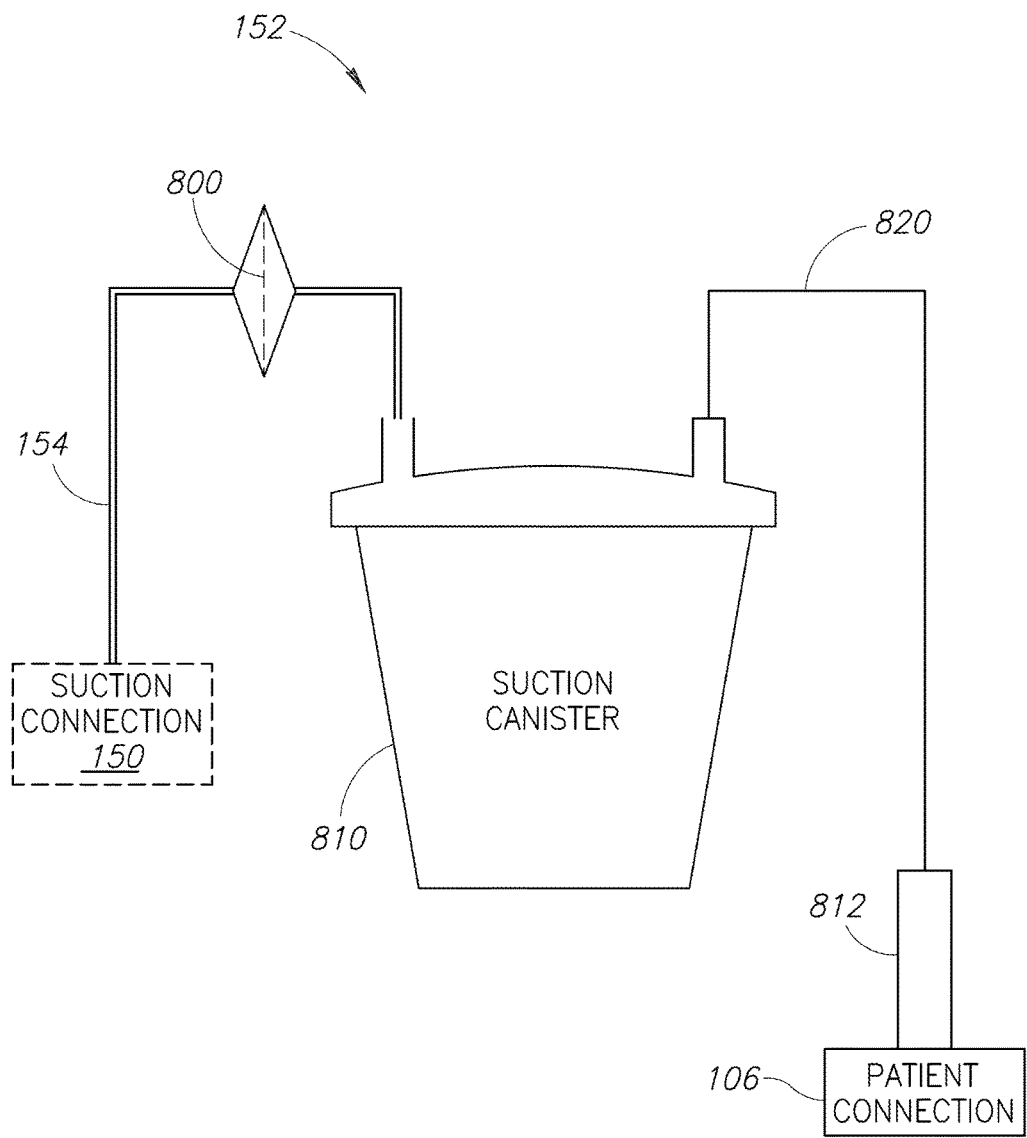
FIG. 16 is a block diagram illustrating an exemplary suction assembly for use with the ventilator of FIG. 1.

Referring to FIG. 16, the suction assembly 152 may include a filter 800, a conventional suction canister 810, a conventional suction catheter 812, and tubing 820 configured to be connected to the suction catheter 812. The suction catheter 812 may be configured to be inserted inside the patient connection 106.

Referring to FIG. 1, the suction assembly 152 provides a means to use the suction 154 provided by the ventilator 100 to "vacuum" secretions from the patient's airway. Referring to FIG. 10G, the control system 220 positions the cam 850 of the first rotary valve assembly 306 to open the poppet valves CV1 and CV3, and, referring to FIG. 13A, the control system 220 positions the cam 530 of the second rotary valve assembly 330 to open the poppet valve CV5. In this configuration, the compressor 302 pulls gas and secretions from the suction catheter 812 (see FIG. 16), through the tubing 820 and into the suction canister 810 (see FIG. 16) where the liquid secretions are trapped. The filter 800 (e.g., a hydrophobic filter) may be used to further prevent patient secretions from entering the ventilator 100 through the suction connection 150. However, gas pulled into the ventilator 100 continues through the first and second rotary valve assemblies 306 and 330, and enters the compressor 302. The control system 220 controls the speed of the motor 350 of the compressor 302 to achieve the user set suction pressure, as measured by the pressure transducer PT2.

Nebulizer Assembly

Referring to FIG. 1, the nebulizer assembly 162 provides a means to use the gases 164 provided by the ventilator 100 for delivering aerosolized medications to the patient's lung(s) 142. Referring to FIG. 10F, the control system 220 positions the cam 850 of the first rotary valve assembly 306 to open the poppet valves CV2 and CV4, and, referring to FIG. 13B, the control system 220 positions the cam 530 of the second rotary valve assembly 330 to open the poppet valve CV6. In this configuration, gas flows from the compressor 302, through the first and second rotary valve assemblies 306 and 330, and on to the nebulizer assembly 162. The control system 220 controls the speed of the motor 350 of the compressor 302 to maintain a desired pressure (e.g., about 12 PSIG) as measured by the pressure transducer PT2. The first rotary valve assembly 306 may be cycled to synchronize medication delivery with the inspiratory phase as desired. In a manner similar to that used for pulse dose oxygen delivery, the control system 220 may compensate (or adjust) the breaths delivered to account for the additional volume delivered by the nebulizer assembly 162.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method of providing a breath to a human patient having a patient connection connected by a patient circuit to a ventilator having a first ventilator connection and a different second ventilator connection, each of the first and second ventilator connections being in fluid communication with the patient circuit, the method comprising:
    identifying, with the ventilator, initiation of an inspiratory phase of the breath;
    delivering a bolus of oxygen to the first ventilator connection before or during the inspiratory phase; and
    delivering breathing gases comprising air to the second ventilator connection during the inspiratory phase, the ventilator isolating the bolus of oxygen delivered to the first ventilator connection from the breathing gases delivered to the second ventilator connection, wherein the delivery of the bolus of oxygen is terminated before commencing the delivery of the breathing gases.

2. The method of claim 1, wherein the bolus of oxygen is delivered at the initiation of the inspiratory phase of the breath.

3. The method of claim 1, further comprising:
    determining, with the ventilator, a volume of the bolus of oxygen delivered for the breath.

4. The method of claim 1 for use with a user specified total tidal volume, wherein the breathing gases delivered for the breath have a first volume, the bolus of oxygen delivered for the breath has a second volume, and combined the first and second volumes are substantially equal to the user specified total tidal volume.

5. The method of claim 1 for use with a user specified peak inspiratory pressure value, wherein a combined pressure of the breathing gases and the bolus of oxygen delivered for the breath does not exceed the user specified peak inspiratory pressure value.

6. A method of providing a breath to a human patient having a patient connection connected by a patient circuit to a ventilator having a first ventilator connection and a different second ventilator connection, each of the first and second ventilator connections being in fluid communication with the patient circuit, the method comprising:
    identifying, with the ventilator, initiation of an inspiratory phase of the breath;
    identifying, with the ventilator, an end of the inspiratory phase of the breath;
    delivering a bolus of oxygen to the first ventilator connection before or during the inspiratory phase;
    terminating the delivery of the bolus of oxygen before the end of the inspiratory phase;
    delivering breathing gases comprising air to the second ventilator connection during the inspiratory phase, the ventilator isolating the bolus of oxygen delivered to the first ventilator connection from the breathing gases delivered to the second ventilator connection, wherein the breathing gasses are delivered after the delivery of the bolus of oxygen has been terminated; and
    measuring an inspiratory pressure value at a location downstream of a merger of the first ventilator connection and the second ventilator connection.

7. The method of claim 6, wherein the bolus of oxygen is delivered at the initiation of the inspiratory phase of the breath.

8. The method of claim 6, further comprising:
    determining, with the ventilator, a volume of the bolus of oxygen delivered for the breath.

9. The method of claim 6 for use with a user specified total tidal volume, wherein the breathing gases delivered for the breath have a first volume, the bolus of oxygen delivered for the breath has a second volume, and combined the first and second volumes are substantially equal to the user specified total tidal volume.

10. The method of claim 6 for use with a user specified peak inspiratory pressure value, wherein a combined pressure of the breathing gases and the bolus of oxygen delivered for the breath does not exceed the user specified peak inspiratory pressure value.

* * * * *

UNITED STATES PATENT AND TRADEMARK OFFICE
CERTIFICATE OF CORRECTION

PATENT NO. : 10,315,002 B2
APPLICATION NO. : 14/667480
DATED : June 11, 2019
INVENTOR(S) : Douglas F. DeVries et al.

It is certified that error appears in the above-identified patent and that said Letters Patent is hereby corrected as shown below:

In the Claims

In Column 40, Line 27, in Claim 6, delete "gasses" and insert -- gases --, therefor.

Signed and Sealed this
Nineteenth Day of May, 2020

Andrei Iancu
*Director of the United States Patent and Trademark Office*